US011845727B2

(12) United States Patent
Hagel et al.

(10) Patent No.: US 11,845,727 B2
(45) Date of Patent: Dec. 19, 2023

(54) ALDEHYDE AND KETONE DERIVATIVES OF PSILOCYBIN AND METHODS OF USING

(71) Applicant: Enveric Biosciences Canada Inc., Calgary (CA)

(72) Inventors: Jillian M. Hagel, Calgary (CA); Peter J. Facchini, Calgary (CA); Chang-Chun Ling, Calgary (CA)

(73) Assignee: ENVERIC BIOSCIENCES CANADA INC., Calgary (CA)

( * ) Notice: Subject to any disclaimer, the term of this patent is extended or adjusted under 35 U.S.C. 154(b) by 0 days.

(21) Appl. No.: 17/951,594

(22) Filed: Sep. 23, 2022

(65) Prior Publication Data

US 2023/0044216 A1 Feb. 9, 2023

Related U.S. Application Data

(63) Continuation of application No. PCT/CA2021/051729, filed on Dec. 3, 2021.

(60) Provisional application No. 63/247,944, filed on Sep. 24, 2021, provisional application No. 63/121,425, filed on Dec. 4, 2020.

(51) Int. Cl.
C07D 209/16 (2006.01)

(52) U.S. Cl.
CPC .................................. *C07D 209/16* (2013.01)

(58) Field of Classification Search
CPC ...................................................... C07D 209/16
See application file for complete search history.

(56) References Cited

U.S. PATENT DOCUMENTS 6,004,991 A * 12/1999 Fourtillan ................ A61P 35/00
514/415

FOREIGN PATENT DOCUMENTS

EP 851855 7/1998

OTHER PUBLICATIONS

Daniel, J. et al. Clinical potential of psilocybin as a treatment for mental health conditions. Mental Health Clin/, 2017;7(1): 24-28.
Grob, C. et al. Pilot study of psilocybin treatment for anxiety in patients with advanced-stage cancerArch. Gen. Psychiatry, 2011, 68(1) 71-78.
Cathart-Harris, R.L. et al. Psilocybin with psychological support for treatment-resistant depression: an open-label feasibility study. Lancet Psychiatry, 2016, 3: 619-627.
Inserra et al., Psychedelics in Psychiatry: Neuroplastic, Immunomodulatory, and Neurotransmitter Mechanisms. 2020, Pharmacol Rev 73: 202.
Terrasso et al., Human neuron-astrocyte 3D co-culture-based assay for evaluation of neuroprotective compounds. 2017, J Pharmacol Toxicol Methods 83: 72.
Pyrgiotakis G. et al., Cell death discrimination with Raman spectroscopy and support vector machines. 2009, Ann. Biomed. Eng. 37: 1464-1473.
Weaver et al., Test systems in drug discovery for hazard identification and risk assessment of human drug-induced liver injury. 2017, Expert Opin Drug Metab Toxicol 13: 767.
Donato et al., Culture and Functional Characterization of Human Hepatoma HepG2 Cells. 2015, Methods Mol Biol 1250: 77.
Núñez et al., Target-drug interactions: first principles and their application to drug discovery. 2012, Drug Disc Today 17:10.
Maguire et al.,Radioligand binding assays and their analysis. 2012, Methods Mol Biol 897: 31.
Kim K. et al.,Structure of a Hallucinogen-Activated Gq-Coupled 5-HT 2A Serotonin Receptor. 2020, Cell 182:1574-1588.
Yamada et al., Chemical & Pharmaceutical Bulletin, 50(1) (2002), pp. 92-99.
Henikoff S & Henikoff, J G, Amino acid substitution matrices from protein blocks. Proc Natl Acad Sci U S A. Nov. 15, 1992;89(22):10915-9.
Horita A. et al. Dephosphorylation of Psilocybin to Psilocin by Alkaline Phosphatse. Proceedings of the Society of Experimental Biology and Medicine, 106(1):32-34, 1961.
Chemical Abstracts—Registry Nos. STN 2501304-93-2 (Nov. 2, 2020).
Cregg et al., Recombinant protein expression in Pichia pastoris. Mol Biotechnol. (2000) 16(1): 23-52.
Glennon et al. Journal of Medicinal Chemistry, 39(1) (1996), pp. 314-322.
Rojas and Fiedler 2016, Front Cell Neurosci 10: 272.
Schnepel C. et al. Enzymatic Halogenation: A Timely Strategy for Regioselective C—H Activation. Chemistry. Sep. 7, 2017;23(50):12064-12086.
Durak L.J. et al. Late-Stage Diversification of Biologically Active Molecules via Chemoenzymatic C—H Functionalization ACS Catal. Mar. 4, 2016; 6(3): 1451-1454.
Corr M.J. et al. Sonogashira diversification of unprotected halotryptophans, halotryptophan containing tripeptides; and generation of a new to nature bromo-natural product and its diversification in water Chem Sci. Mar. 1, 2017;8 (3):2039-2046.
ISR & Written Opinion—dated Feb. 2, 2022.
Cameron and Olson 2018, ACS Chem Neurosci 9: 2344.
Finnin, B. and Morgan, T.M., Transdermal penetration enhancers: applications, limitations, and potential J Pharm Sci. Oct. 1999;88(10):955-8.
Kerschgens, I.; Claveau, E.; Wanner, M.; Ingemann, S.; Maarseveen, J. H.; Hiemstra, H. Chem. Commun. 2012, 48, 12243-12245.
Mattanovich et al., Recombinant protein production in yeasts. Methods Mol. Biol., 2012, 824:329-58.
Romanos et al., Foreign gene expression in yeast: a review. Yeast. Jun. 1992;8(6):423-88.

(Continued)

*Primary Examiner* — Shawquia Jackson
(74) *Attorney, Agent, or Firm* — BERESKIN & PARR LLP/S.E.N.C.R.L., s.r.l.; Michael Fenwick

(57) ABSTRACT

Disclosed are novel aldehyde and ketone psilocybin derivative compounds and pharmaceutical and recreational drug formulations containing the same. The compounds may be produced by reacting a reactant psilocybin derivative with an aldehyde or ketone group containing compound.

18 Claims, 49 Drawing Sheets

(56) References Cited

OTHER PUBLICATIONS

Roy A.D. et al. Development of fluorescent aryltryptophans by Pd mediated cross-coupling of unprotected halotryptophans in water. Chem Commun (Camb). Oct. 21, 2008;(39):4831-3.

Runguphan W. et al. Diversification of monoterpene indole alkaloid analogs through cross-coupling. Org Lett. Jun. 7, 2013;15(11):2850-3.

Kozell, L.B. et al. Pharmacologic Activity of Substituted Tryptamines at 5-Hydroxytryptamine (5-HT)2A Receptor (5-HT2AR), 5-HT2CR, 5-HT1AR, and Serotonin Transporter. J Pharmacol Exp Ther 385:62-75, Apr. 2023.

* cited by examiner

ALDEHYDE AND KETONE DERIVATIVES OF PSILOCYBIN AND METHODS OF USING

RELATED APPLICATIONS

This application is a continuation of PCT Application No. PCT/CA2021/051729 filed Dec. 3, 2021, which claims the benefit of U.S. Provisional Application No. 63/121,425 filed Dec. 4, 2020 and U.S. Provisional Application No. 63/247,944 filed Sep. 24, 2021; the entire contents of Patent Application Nos. PCT/CA2021/051729, 63/121,425 and 63/247,944 are hereby incorporated by reference.

FIELD OF THE DISCLOSURE

The compositions and methods disclosed herein relate to a chemical compound known as psilocybin. Furthermore, the compositions and methods disclosed herein relate in particular to aldehyde and ketone derivatives of psilocybin.

BACKGROUND OF THE DISCLOSURE

The following paragraphs are provided by way of background to the present disclosure. They are not however an admission that anything discussed therein is prior art or part of the knowledge of a person of skill in the art.

The biochemical pathways in the cells of living organisms may be classified as being part of primary metabolism, or as being part of secondary metabolism. Pathways that are part of a cell's primary metabolism are involved in catabolism for energy production or in anabolism for building block production for the cell. Secondary metabolites, on the other hand, are produced by the cell without having an obvious anabolic or catabolic function. It has long been recognized that secondary metabolites can be useful in many respects, including as therapeutic compounds.

Psilocybin, for example, is a secondary metabolite that is naturally produced by certain mushrooms which taxonomically can be classified as belonging the Basidiomycota division of the fungi kingdom. Mushroom species which can produce psilocybin include species belonging to the genus *Psilocybe*, such as *Psilocybe azurescens, Psilocybe semilanceata, Psilocybe serbica, Psilocybe mexicana*, and *Psilocybe cyanescens*, for example. The interest of the art in psilocybin is well established. Thus, for example, psilocybin is a psychoactive compound and is therefore used as a recreational drug. Furthermore, psilocybin is used as a research tool in behavioral and neuro-imaging studies in psychotic disorders, and has been evaluated for its clinical potential in the treatment of mental health conditions (Daniel, J. et al., Mental Health Clin/, 2017; 7(1): 24-28), including to treat anxiety in terminal cancer patients (Grob, C. et al., Arch. Gen. Psychiatry, 2011, 68(1) 71-78) and to alleviate symptoms of treatment-resistant depression (Cathart-Harris, R. L. et al., Lancet Psychiatry, 2016, 3: 619-627).

Although the toxicity of psilocybin is low, adverse side effects, including, for example, panic attacks, paranoia, and psychotic states, sometimes together or individually referred to as "a bad trip", are not infrequently experienced by recreational psilocybin users.

There exists therefore a need in the art for improved psilocybin compounds.

SUMMARY OF THE DISCLOSURE

The following paragraphs are intended to introduce the reader to the more detailed description, not to define or limit the claimed subject matter of the present disclosure.

In one aspect, the present disclosure relates to psilocybin and derivative compounds.

In another aspect, the present disclosure relates to aldehyde and ketone derivatives of psilocybin and methods of making and using these compounds.

Accordingly, in one aspect, the present disclosure provides, in at least one embodiment, in accordance with the teachings herein, a chemical compound having the chemical formula (I):

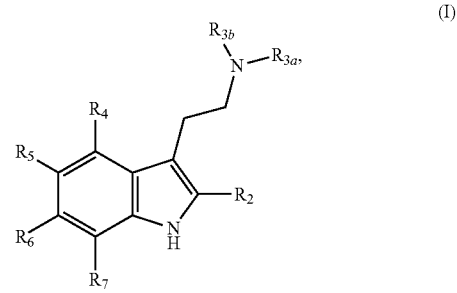

wherein, at least one of $R_2$, $R_5$, $R_6$, or $R_7$ is an aldehyde or a ketone group, and wherein each of $R_2$, $R_5$, $R_6$, or $R_7$ which is not an aldehyde group or a ketone group, is a hydrogen atom, an alkyl group, or O-alkyl group, wherein $R_4$ is an O-alkyl group, an O-acyl group, an O-aryl group, an O-alkaryl group, a hydroxy group, a phosphate group, a glycosyloxy group, or a hydrogen atom and wherein $R_{3A}$ and $R_{3B}$ each independently are a hydrogen atom, an alkyl group, acyl group or an aryl group.

In at least one embodiment, in an aspect, the ketone group can have the chemical formula (II):

wherein R is an alkyl group, a halogenated alkyl group or an aryl group.

In at least one embodiment, in an aspect, the ketone group can have the chemical formula (III):

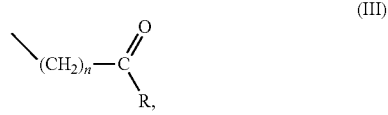

wherein R is an alkyl group, a halogenated alkyl group, or an aryl group, and n is an integer from 1-10, when R is an alkyl group, or an aryl group, or wherein n is an integer from 0-10 when R is a halogenated alkyl group.

In at least one embodiment, in an aspect, the aldehyde group can have the chemical formula (IV):

In at least one embodiment, in an aspect, the aldehyde group can have the chemical formula (V):

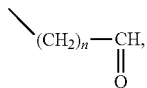
(V)

wherein n is an integer from 1-10.

In at least one embodiment, in an aspect, at least two of $R_2$, $R_5$, $R_6$, or $R_7$ can be an aldehyde group or a ketone group.

In at least one embodiment, in an aspect, at least three of $R_2$, $R_5$, $R_6$, or $R_7$ can be an aldehyde group or a ketone group.

In at least one embodiment, in an aspect, all four of $R_2$, $R_5$, $R_6$, or $R_7$ can be an aldehyde group or a ketone group.

In at least one embodiment, in an aspect, $R_5$ or $R_7$ can be an aldehyde group or a ketone group and $R_4$ can be an O-alkyl group.

In at least one embodiment, in an aspect, $R_5$ or $R_7$ can be an aldehyde group or a ketone group and $R_4$ can be an O-acyl group.

In at least one embodiment, in an aspect, $R_5$ or $R_7$ can be an aldehyde group or a ketone group and $R_4$ can be an O-aryl group.

In at least one embodiment, in an aspect, $R_5$ or $R_7$ can be an aldehyde group or a ketone group and $R_4$ can be a phosphate group.

In at least one embodiment, in an aspect, $R_5$ or $R_7$ can be an aldehyde group or a ketone group and $R_4$ can be a glycosyloxy group.

In at least one embodiment, in an aspect, $R_5$ or $R_7$ can be an aldehyde group or a ketone group and $R_4$ can be a hydroxy group.

In at least one embodiment, in an aspect, $R_5$ or $R_7$ can be an aldehyde group or a ketone group and $R_4$ can be a hydrogen atom.

In at least one embodiment, in an aspect, $R_5$ and $R_7$ can be an aldehyde group or a ketone group and $R_4$ can be an O-alkyl group.

In at least one embodiment, in an aspect, $R_5$ and $R_7$ can be an aldehyde group or a ketone group and $R_4$ can be an O-acyl group.

In at least one embodiment, in an aspect, $R_5$ and $R_7$ can be an aldehyde group or a ketone group and $R_4$ can be an O-aryl group.

In at least one embodiment, in an aspect, $R_5$ and $R_7$ can be an aldehyde group or a ketone group and $R_4$ can be an O-alkaryl group.

In at least one embodiment, in an aspect, $R_5$ and $R_7$ can be an aldehyde group or a ketone group and $R_4$ can be a phosphate group.

In at least one embodiment, in an aspect, $R_5$ and $R_7$ can be an aldehyde group or a ketone group and $R_4$ can be a glycosyloxy group.

In at least one embodiment, in an aspect, $R_5$ and $R_7$ can be an aldehyde group or a ketone group and $R_4$ can be a hydroxy group.

In at least one embodiment, in an aspect, $R_5$ and $R_7$ can be an aldehyde group or a ketone group and $R_4$ can be a hydrogen atom.

In at least one embodiment, in an aspect, the chemical compound can be selected from the group consisting of compounds having formulas (VIII), (IX), (X), (XI), (XII), (XIII), (XIV) and (XV):

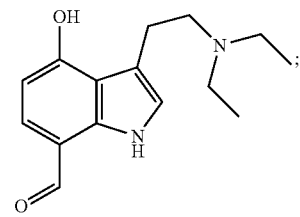
(VIII)

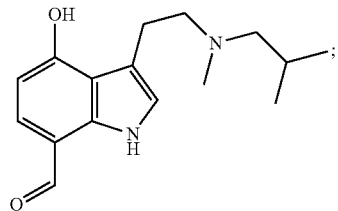
(IX)

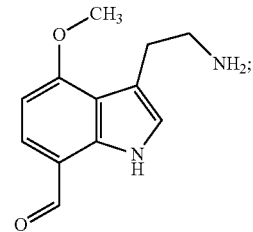
(X)

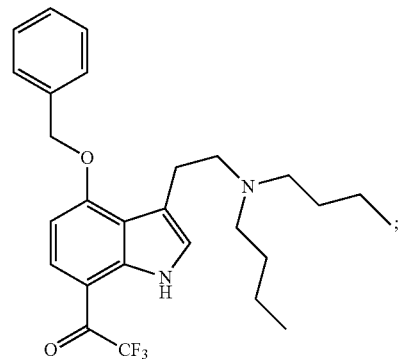
(XI)

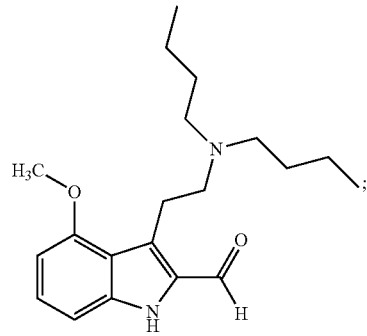
(XII)

-continued

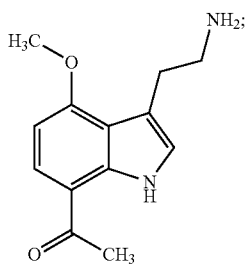
(XIII)

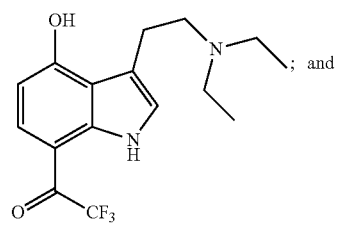
(XIV)

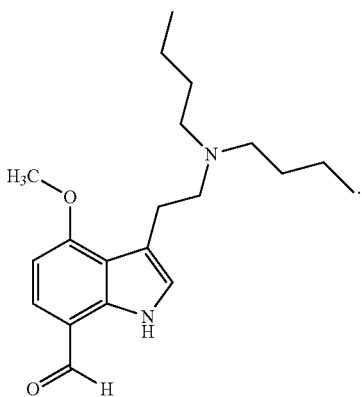
(XV)

In another aspect, the present disclosure relates to pharmaceutical and recreational drug formulations comprising psilocybin derivatives. Accordingly, in one aspect, the present disclosure provides, in at least one embodiment, a pharmaceutical or recreational drug formulation comprising an effective amount of a chemical compound having the chemical formula (I):

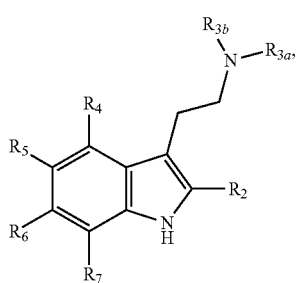
(I)

wherein, at least one of $R_2$, $R_5$, $R_6$, or $R_7$ is an aldehyde group or a ketone group, and wherein each $R_2$, $R_5$, $R_6$, or $R_7$ which is not an aldehyde group or a ketone group, is a hydrogen atom, an alkyl group, or O-alkyl group, wherein $R_4$ is an O-alkyl group, an O-acyl group, an O-aryl group, an O-alkaryl group, a hydroxy group, a phosphate group, a glycosyloxy group, or a hydrogen atom and wherein $R_{3A}$ and $R_{3B}$ each independently are a hydrogen atom, an alkyl group, acyl group or an aryl group, together with a pharmaceutically acceptable excipient, diluent or carrier.

In another aspect, the present disclosure relates to methods of treatment of psychiatric disorders. Accordingly, the present disclosure further provides, in one embodiment, a method for treating a psychiatric disorder, the method comprising administering to a subject in need thereof a pharmaceutical formulation comprising a chemical compound having the chemical formula (I):

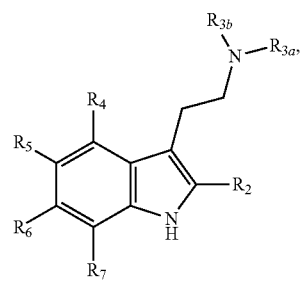
(I)

wherein, at least one of $R_2$, $R_5$, $R_6$, or $R_7$ is an aldehyde group or a ketone group, and wherein each of $R_2$, $R_5$, $R_6$, or $R_7$ which is not an aldehyde group or a ketone group, is a hydrogen atom, an alkyl group, or O-alkyl group, wherein $R_4$ is an O-alkyl group, an O-acyl group, an O-aryl group, an O-alkaryl group, a hydroxy group, a phosphate group, a glycosyloxy group, or a hydrogen atom and wherein $R_{3A}$ and $R_{3B}$ each independently are a hydrogen atom, an alkyl group, acyl group or an aryl group, wherein the pharmaceutical formulation is administered in an effective amount to treat the psychiatric disorder in the subject.

In at least one embodiment, in an aspect, the disorder can be a 5-$HT_{2A}$ receptor mediated disorder or a 5-$HT_{1A}$ receptor mediated disorder.

In at least one embodiment, in an aspect, a dose can be administered of about 0.001 mg to about 5,000 mg.

In another aspect, the present disclosure relates to methods of making aldehyde and ketone derivatives of psilocybin. Accordingly, in one aspect, the present disclosure provides, in at least one embodiment, a method of making an aldehyde or ketone derivative of psilocybin, the method comprising reacting a reactant psilocybin derivative compound with an aldehyde or ketone-group containing compound under conditions sufficient to form an aldehyde or ketone derivative of psilocybin.

In at least one embodiment, the reactant psilocybin derivative can be a chemical compound having the chemical formula (VI):

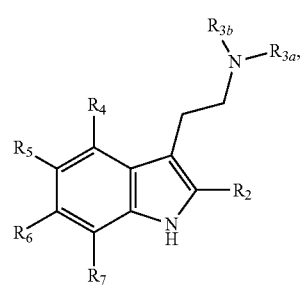
(VI)

wherein, at least one of $R_2$, $R_5$, $R_6$, or $R_7$ is a hydrogen atom, wherein $R_4$ is an O-alkyl group, an O-acyl group, an O-aryl group, an O-alkaryl group, a hydroxy group, a phosphate group, a glycosyloxy group, or a hydrogen atom and wherein $R_{3A}$ and $R_{3B}$ each independently are a hydrogen atom, an oxygen atom, an alkyl group, acyl group or an aryl group.

In at least one embodiment, in an aspect, all of $R_2$, $R_5$, $R_6$, or $R_7$ of chemical compound having chemical formula (VI) can be a hydrogen atom.

In at least one embodiment, in an aspect, at least one of $R_2$, $R_5$, $R_6$, or $R_7$ of chemical compound having chemical formula (VI) can be an aldehyde group or a ketone group, and wherein $R_2$, $R_5$, $R_6$, or $R_7$ which are not an aldehyde or a ketone group, can be a hydrogen atom.

In at least one embodiment, in an aspect, at least two of $R_2$, $R_5$, $R_6$, or $R_7$ of chemical compound having chemical formula (VI) can be an aldehyde group or a ketone group, and wherein $R_2$, $R_5$, $R_6$, or $R_7$ which are not an aldehyde or a ketone group, can be a hydrogen atom.

In at least one embodiment, in an aspect, at least three of $R_2$, $R_5$, $R_6$, or $R_7$ of chemical compound having chemical formula (VI) can be an aldehyde group or a ketone group, and wherein $R_2$, $R_5$, $R_6$, or $R_7$ which are not an aldehyde or a ketone group, can be a hydrogen atom.

In at least one embodiment, in an aspect, in the formed aldehyde and ketone psilocybin derivative at least one of $R_5$ or $R_7$ can be an aldehyde group or a ketone group, and wherein $R_5$, or $R_7$ which are not an aldehyde group or a ketone group, and $R_2$ and $R_6$ are each a hydrogen atom.

In at least one embodiment, in an aspect, in the formed aldehyde and ketone psilocybin derivative $R_5$ and $R_7$ can be an aldehyde group or a ketone group, and $R_2$ and $R_6$ are a hydrogen atom.

In at least one embodiment, in an aspect, in chemical compound having chemical formula (VI) $R_4$ can be an O-alkyl group, and in the formed aldehyde and ketone psilocybin derivative at least one of $R_5$ or $R_7$ can be an aldehyde group or a ketone group, and wherein $R_5$, or $R_7$ which are not an aldehyde group or ketone group, and $R_2$ and $R_6$ are each a hydrogen atom.

In at least one embodiment, in an aspect, in chemical compound having chemical formula (VI) $R_4$ can be an O-acyl group, and in the formed aldehyde and ketone psilocybin derivative at least one of $R_5$ or $R_7$ can be an aldehyde group or ketone group, and wherein $R_5$, or $R_7$ which are not an aldehyde group or ketone group and $R_2$ and $R_6$ are each a hydrogen atom.

In at least one embodiment, in an aspect, in chemical compound having chemical formula (VI) $R_4$ can be an O-aryl group, and in the formed aldehyde and ketone psilocybin derivative at least one of $R_5$ or $R_7$ can be an aldehyde group or ketone group, and wherein $R_5$, or $R_7$ which are not an aldehyde group or ketone group and $R_2$ and $R_6$ are each a hydrogen atom.

In at least one embodiment, in an aspect, in chemical compound having chemical formula (VI) $R_4$ can be an O-alkaryl group, and in the formed aldehyde and ketone psilocybin derivative at least one of $R_5$ or $R_7$ can be an aldehyde group or ketone group, and wherein $R_5$, or $R_7$ which are not an aldehyde group or ketone group and $R_2$ and $R_6$ are each a hydrogen atom.

In at least one embodiment, in an aspect, in chemical compound having chemical formula (VI) $R_4$ can be a hydroxy group, and in the formed aldehyde and ketone psilocybin derivative at least one of $R_5$ or $R_7$ can be an aldehyde group or ketone group, and wherein $R_5$ or $R_7$ which are not an aldehyde group or ketone group, and $R_2$ and $R_6$ are each a hydrogen atom.

In at least one embodiment, in an aspect, in chemical compound having chemical formula (VI) $R_4$ can be a phosphate group, and in the formed aldehyde and ketone psilocybin derivative at least one of $R_5$ or $R_7$ can be an aldehyde group or ketone group, and wherein $R_5$ or $R_7$ which are not an aldehyde group or ketone group and $R_2$ and $R_6$ are each a hydrogen atom.

In at least one embodiment, in an aspect, in chemical compound having chemical formula (VI) $R_4$ can be a glycosyloxy group, and the formed aldehyde and ketone psilocybin derivative at least one of $R_5$ or $R_7$ can be an aldehyde group or ketone group, and wherein $R_5$, or $R_7$ which are not an aldehyde group or ketone group and $R_2$ and $R_6$ are each a hydrogen atom.

In at least one embodiment, in an aspect, in chemical compound having chemical formula (VI) $R_4$ can be a hydrogen atom, and in the formed aldehyde and ketone psilocybin derivative at least one of $R_5$ or $R_7$ can be an aldehyde group or ketone group, and wherein $R_5$, or $R_7$ which are not an aldehyde group or ketone group and $R_2$ and $R_6$ are each a hydrogen atom.

In at least one embodiment, in an aspect, in chemical compound having chemical formula (VI) $R_4$ can be an O-alkyl group, and in the formed aldehyde and ketone psilocybin derivative $R_5$ and $R_7$ can be an aldehyde group or ketone group, and $R_2$ and $R_6$ are a hydrogen atom.

In at least one embodiment, in an aspect, in chemical compound having chemical formula (VI) $R_4$ can be an O-acyl group, and in the formed aldehyde and ketone psilocybin derivative $R_5$ and $R_7$ can be an aldehyde group or ketone group, and $R_2$ and $R_6$ are a hydrogen atom.

In at least one embodiment, in an aspect, in chemical compound having chemical formula (VI) $R_4$ can be an O-aryl group, and in the formed aldehyde and ketone psilocybin derivative $R_5$ and $R_7$ can be an aldehyde group or ketone group, and $R_2$ and $R_6$ are a hydrogen atom.

In at least one embodiment, in an aspect, in chemical compound having chemical formula (VI) $R_4$ can be an O-alkaryl group, and in the formed aldehyde and ketone psilocybin derivative $R_5$ and $R_7$ can be an aldehyde group or ketone group, and $R_2$ and $R_6$ are a hydrogen atom.

In at least one embodiment, in an aspect, in chemical compound having chemical formula (VI) $R_4$ can be a hydroxy group, and in the formed aldehyde and ketone psilocybin derivative at $R_5$ and $R_7$ can be an aldehyde group or ketone group, and $R_2$ and $R_6$ are a hydrogen atom.

In at least one embodiment, in an aspect, in chemical compound having chemical formula (VI) $R_4$ can be a phosphate group, and in the formed aldehyde and ketone psilocybin derivative at $R_5$ and $R_7$ can be an aldehyde group or ketone group, and $R_2$ and $R_6$ are a hydrogen atom.

In at least one embodiment, in an aspect, in chemical compound having chemical formula (VI) $R_4$ can be a glycosyloxy group, and in the formed aldehyde and ketone psilocybin derivative at $R_5$ and $R_7$ can be an aldehyde group or ketone group, and $R_2$ and $R_6$ are a hydrogen atom.

In at least one embodiment, in an aspect, in chemical compound having chemical formula (VI) $R_4$ can be a hydrogen atom, and in the formed aldehyde and ketone psilocybin derivative at $R_5$ and $R_7$ can be an aldehyde group or ketone group, and $R_2$ and $R_6$ are a hydrogen atom.

In at least one embodiment, in an aspect, the method comprises a method for forming an aldehyde or ketone psilocybin derivative having a formula (XVI):

(XVI)

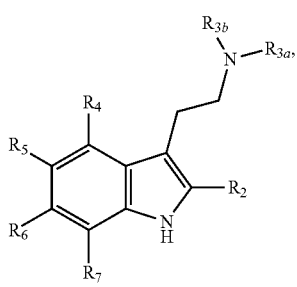

wherein, at least one of $R_2$, $R_5$, $R_6$, or $R_7$ is an aldehyde or a ketone group, and wherein each of $R_2$, $R_5$, $R_6$, or $R_7$ which is not an aldehyde group or a ketone group, is a hydrogen atom, an alkyl group, or O-alkyl group, wherein $R_4$ is an O-alkyl group, an O-acyl group, an O-aryl group, an O-alkaryl group, a phosphate group, a glycosyloxy group, or a hydrogen atom, and wherein $R_{3A}$ and $R_{3B}$ each independently are alkyl group, acyl group or an aryl group, or a hydrogen atom, provided however, that $R_{3b}$ and $R_{3a}$ are not both simultaneously a hydrogen atom, the method further comprising:

(a) providing an indole derivative compound having formula (XVII):

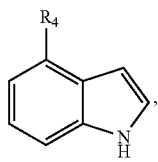
(XVII)

wherein $R_4$ is an O-alkyl group, an O-acyl group, an O-aryl group, an O-alkaryl group, a phosphate group, a glycosyloxy group, or a hydrogen atom;

(b) reacting the compound having formula (XVII) with (i) an oxalyl halogen compound and (ii) a compound having formula (XVIII):

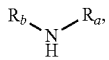
(XVIII)

wherein one or both of $R_a$ and $R_b$ are an alkyl group, and wherein when $R_a$ or $R_b$ are not both an alkyl group, one of $R_a$ or $R_b$ is a hydrogen atom, to form a first intermediate compound having chemical formula (XIX):

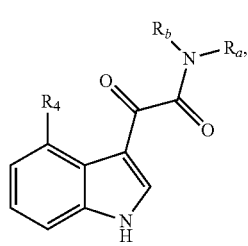
(XIX)

wherein $R_4$ is an O-alkyl group, an O-acyl group, an O-aryl group, an O-alkaryl group, a phosphate group, a glycosyloxy group, or a hydrogen atom, and wherein one or both of $R_a$ and $R_b$ are an alkyl group, and wherein when $R_a$ or $R_b$ are not both an alkyl group, one of $R_a$ or $R_b$ is a hydrogen atom;

(c) deoxygenizing the first intermediate compound having chemical formula (XIXI) to form a second intermediate compound having chemical formula (XX):

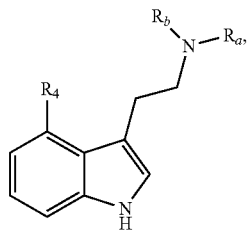
(XX)

wherein $R_4$ is an O-alkyl group, an O-acyl group, an O-aryl group, an O-alkaryl group, a phosphate group, a glycosyloxy group, or a hydrogen atom, and wherein one or both of $R_a$ and $R_b$ are an alkyl group, and wherein when $R_a$ or $R_b$ are not both an alkyl group, one of $R_a$ or $R_b$ is a hydrogen atom; and (d) reacting the second intermediate compound having chemical formula (XX) with an aldehyde group or ketone group forming compound to form the compound having chemical formula (XVI).

In at least one embodiment, in an aspect, one or both of $R_a$ or $R_b$ can be independently selected from a methyl group, an ethyl group, or a propyl group.

In at least one embodiment, in an aspect, the oxalyl halogen compound can be oxalyl chloride.

In at least one embodiment, in an aspect, the aldehyde group or ketone group forming compound can be trifluoroacetic anhydride (TCAA) or tetrahydrofuran (THF).

In at least one embodiment, in an aspect, the formed aldehyde or ketone psilocybin derivative can have a chemical formula (XI), (XII) or (XV):

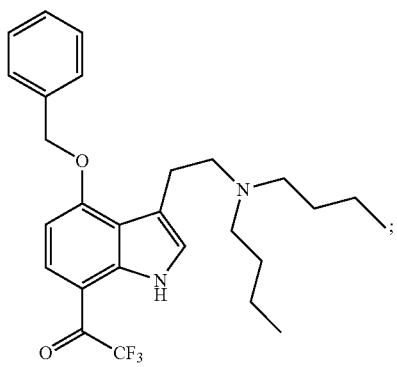
(XI)

(XII)
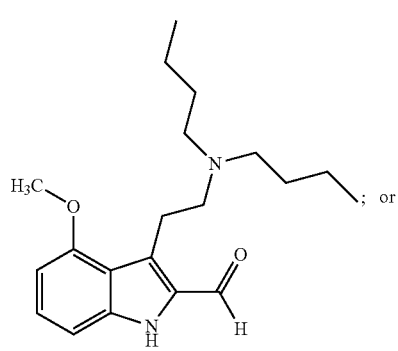
; or
(XV)
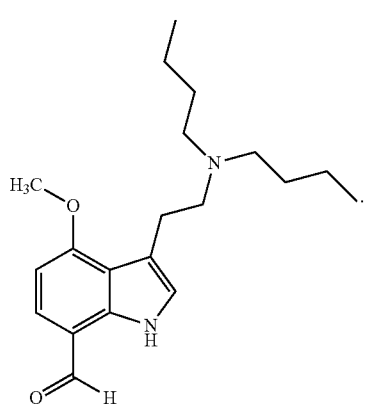
.
In at least one embodiment, in an aspect, the formed aldehyde or ketone derivative of psilocybin is selected from the group consisting of compounds having formulas (VIII), (IX), (X), (XI), (XII), (XIII), (XIV) and (XV):
(VIII)
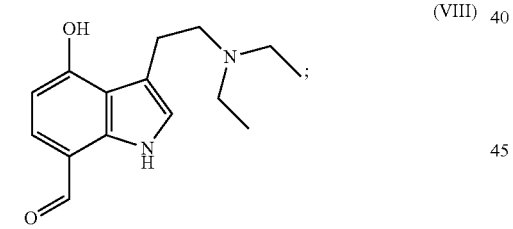
;
(IX)
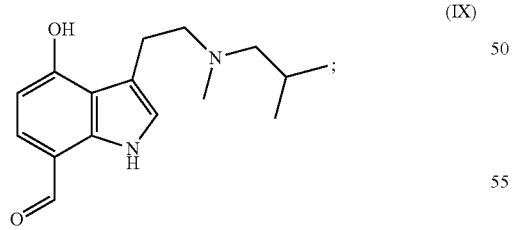
;
(X)
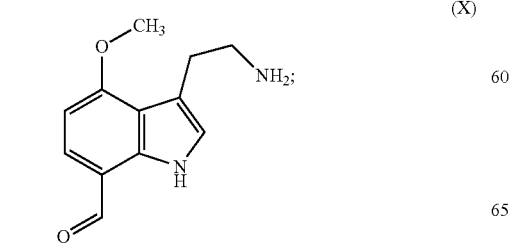
;
(XI)
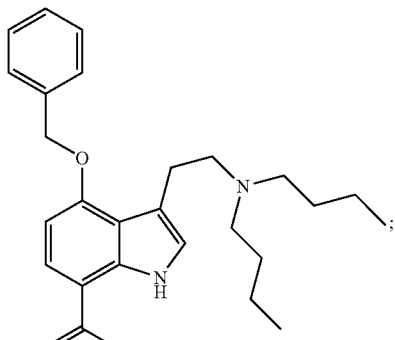
;
(XII)
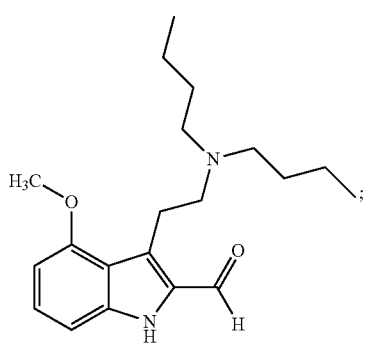
;
(XIII)
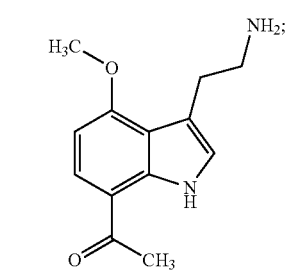
;
(XIV)
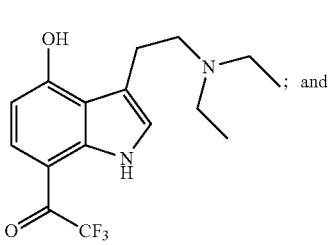
; and
(XV)
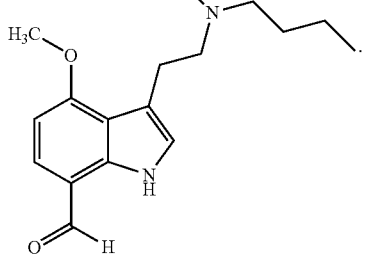
.

In another aspect, the present disclosure provides, in at least one embodiment, a method for modulating a 5-HT$_{2A}$ receptor or a 5-HT$_{aA}$ receptor, the method comprising contacting a 5-HT$_{2A}$ receptor or a 5-HT$_{aA}$ receptor with a chemical compound or salt thereof having formula (I):

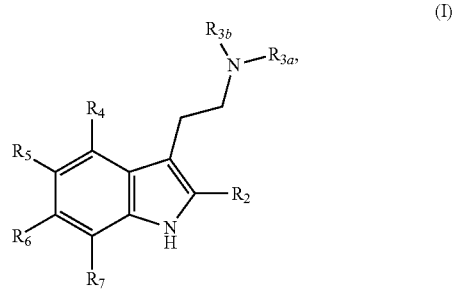

(I)

wherein, at least one of $R_2$, $R_5$, $R_6$, or $R_7$ is an aldehyde or ketone group, and wherein each $R_2$, $R_5$, $R_6$, or $R_7$ which is not an aldehyde or ketone group is a hydrogen atom, an alkyl group, or O-alkyl group, an O-alkaryl group, wherein $R_4$ is an O-alkyl group, an O-acyl group, an O-aryl group, a hydroxy group, a phosphate group, a glycosyloxy group, or a hydrogen atom and wherein $R_{3A}$ and $R_{3B}$ each independently are a hydrogen atom, an alkyl group, acyl group or an aryl group, or an acyl group under reaction conditions sufficient to thereby modulate receptor activity.

In some embodiments, in an aspect, the reaction conditions can be in vitro reaction conditions.

In some embodiments, in an aspect, the reaction conditions can be in vivo reaction conditions.

In another aspect the present disclosure provides, in at least one embodiment, a use of a chemical compound having the chemical formula (I):

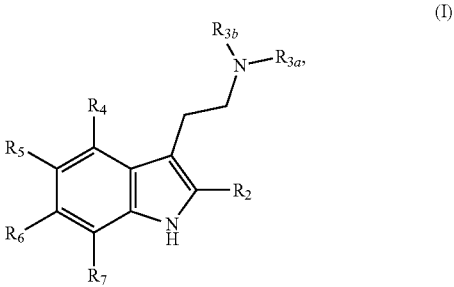

(I)

wherein, at least one of $R_2$, $R_5$, $R_6$, or $R_7$ is an aldehyde group or a ketone group, and wherein each $R_2$, $R_5$, $R_6$, or $R_7$ which is not an aldehyde group or a ketone group, is a hydrogen atom, an alkyl group, or O-alkyl group, wherein $R_4$ is an O-alkyl group, an O-acyl group, an O-aryl group, an O-alkaryl group, a hydroxy group, a phosphate group, a glycosyloxy group, or a hydrogen atom and wherein $R_{3A}$ and $R_{3B}$ each independently are a hydrogen atom, an alkyl group, acyl group or an aryl group, in the manufacture of a pharmaceutical or recreational drug formulation.

In at least one embodiment, in an aspect, the manufacture can comprise formulating the chemical compound with an excipient, diluent or carrier.

In another aspect the present disclosure provides, in at least one embodiment, a use of a chemical compound having the chemical formula (I):

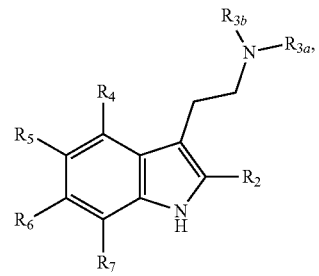

(I)

wherein, at least one of $R_2$, $R_5$, $R_6$, or $R_7$ is an aldehyde group or a ketone group, and wherein each $R_2$, $R_5$, $R_6$, or $R_7$ which is not an aldehyde group or a ketone group is a hydrogen atom, an alkyl group, or O-alkyl group, wherein $R_4$ is an O-alkyl group, an O-acyl group, an O-aryl group, an O-alkaryl group, a hydroxy group, a phosphate group, a glycosyloxy group, or a hydrogen atom and wherein $R_{3A}$ and $R_{3B}$ each independently are a hydrogen atom, an alkyl group, acyl group or an aryl group, together with a diluent, carrier, or excipient as a pharmaceutical or recreational drug formulation.

Other features and advantages will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The figures are not intended to limit the present disclosure.

FIGS. 10A and 10C depict examples of chemical reactions to form 4-O-methyl-psilocybin derivatives mono-formylated at the $C_5$- or $C_7$-position, or di-formylated at both the $C_5$- and $C_7$-position using a 4-O-methyl-psilocybin derivative as a reactant. FIGS. 10B and 10D depict further example of chemical reactions, namely, to form a 4-hydroxy-psilocybin derivative formylated at the $C_5$-position using a 4-hydroxy-psilocybin derivative as a reactant. FIG. 10E depicts an example of a chemical rearrangement reaction to form 4-hydroxy-psilocybin derivatives formylated at either 5-position or 7-position using a 4-O-formyl-psilocybin derivative as a reactant. FIG. 10F depicts an example of a chemical synthesis reaction to form a 4-hydroxy-psilocybin derivative bearing an alkyl group at the $C_5$-position that is modified with a formyl group at the end of the chain, using a 4-hydroxy-psilocybin derivative.

FIG. 11A depicts an example of a chemical reaction to form 4-hydroxy-psilocybin derivatives mono-acylated at the $C_5$- or $C_7$-position, using a 4-hydroxy-psilocybin derivative and either an acyl chloride or anhydride as a reactant. FIG. 11B depicts another example of a chemical reaction to form 4-hydroxy-psilocybin derivatives mono-acylated at the $C_5$- or $C_7$-position using a 4-hydroxy-psilocybin derivative and either an alkylnitrile or arylnitrile as a reactant. FIG. 11C depicts an example of a chemical rearrangement reaction to form 4-hydroxy-psilocybin derivatives monoacylated at either the $C_5$-position or the $C_7$-position using a 4-O-acyl-psilocybin derivative as a reactant.

FIGS. 12A, 12B, 12C, and 12E depict example chemical reactions to form various 7-formyl-psilocybin derivatives and 2-formyl psilocybin derivatives. FIGS. 12D, 12F and 12G depict chemical reactions for forming various 7-trifluoromethyl psilocybin derivatives.

Figure 14A:
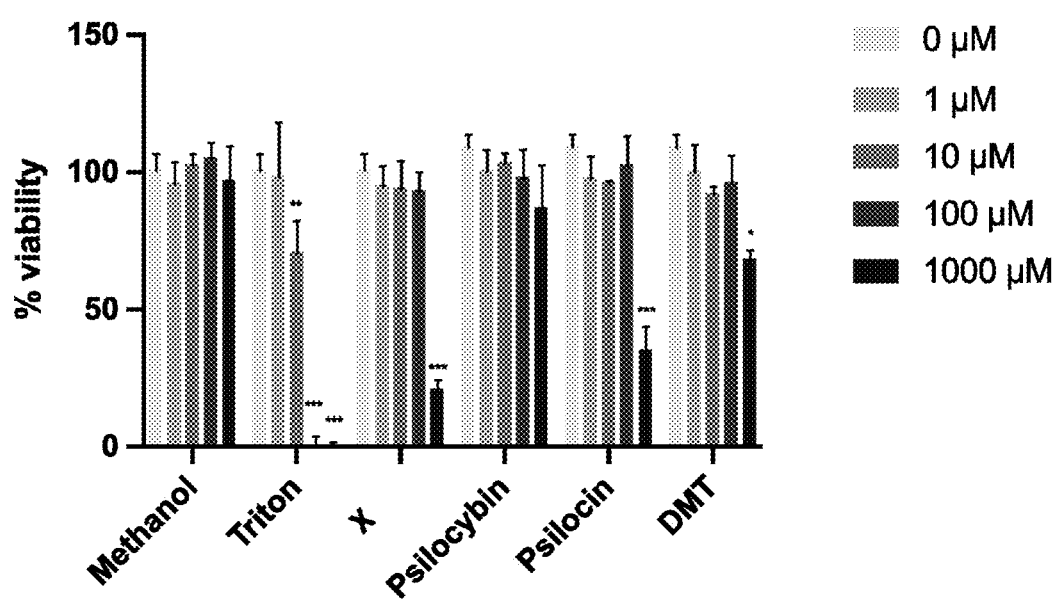
FIGS. 14A, 14B, 14C, 14D, 14E, 14F and 14G depict various further graphs, obtained in the performance of experimental assays to evaluate the efficacy of an example aldehyde psilocybin derivative having the chemical formula (X) set forth herein, notably a cell viability assay (FIG.
Figure 14B:
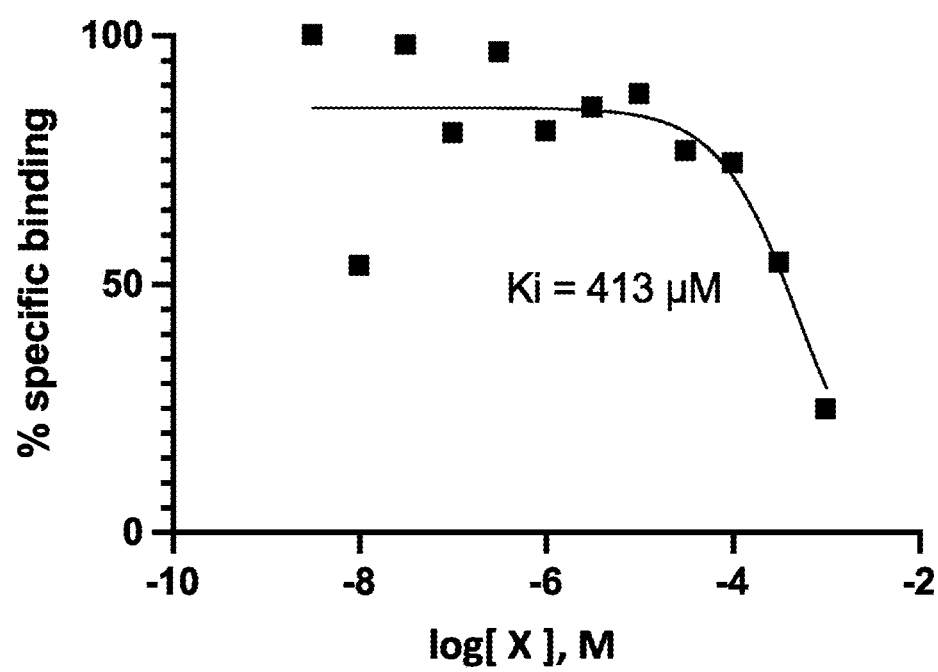
Figure 14C:
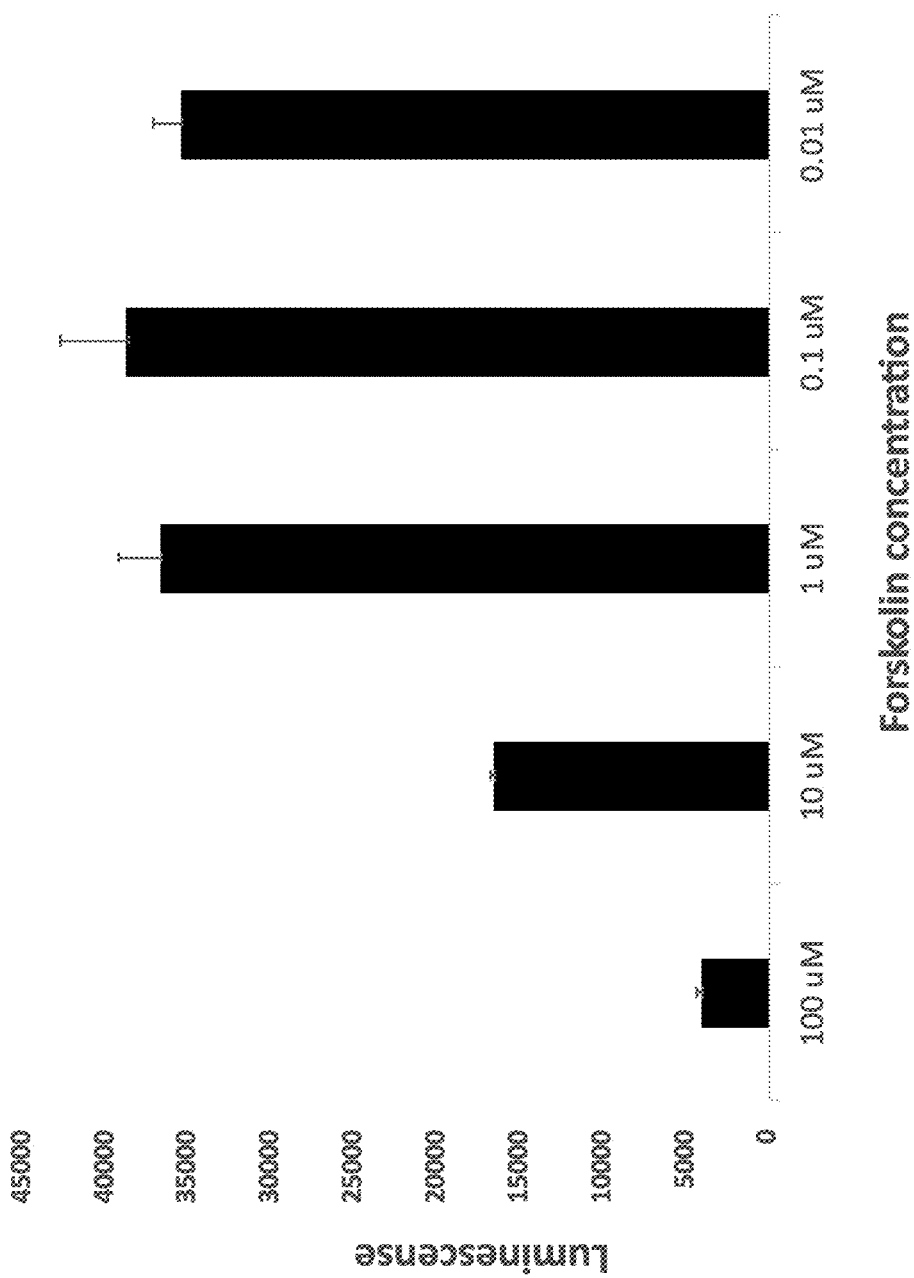
Figure 14D:
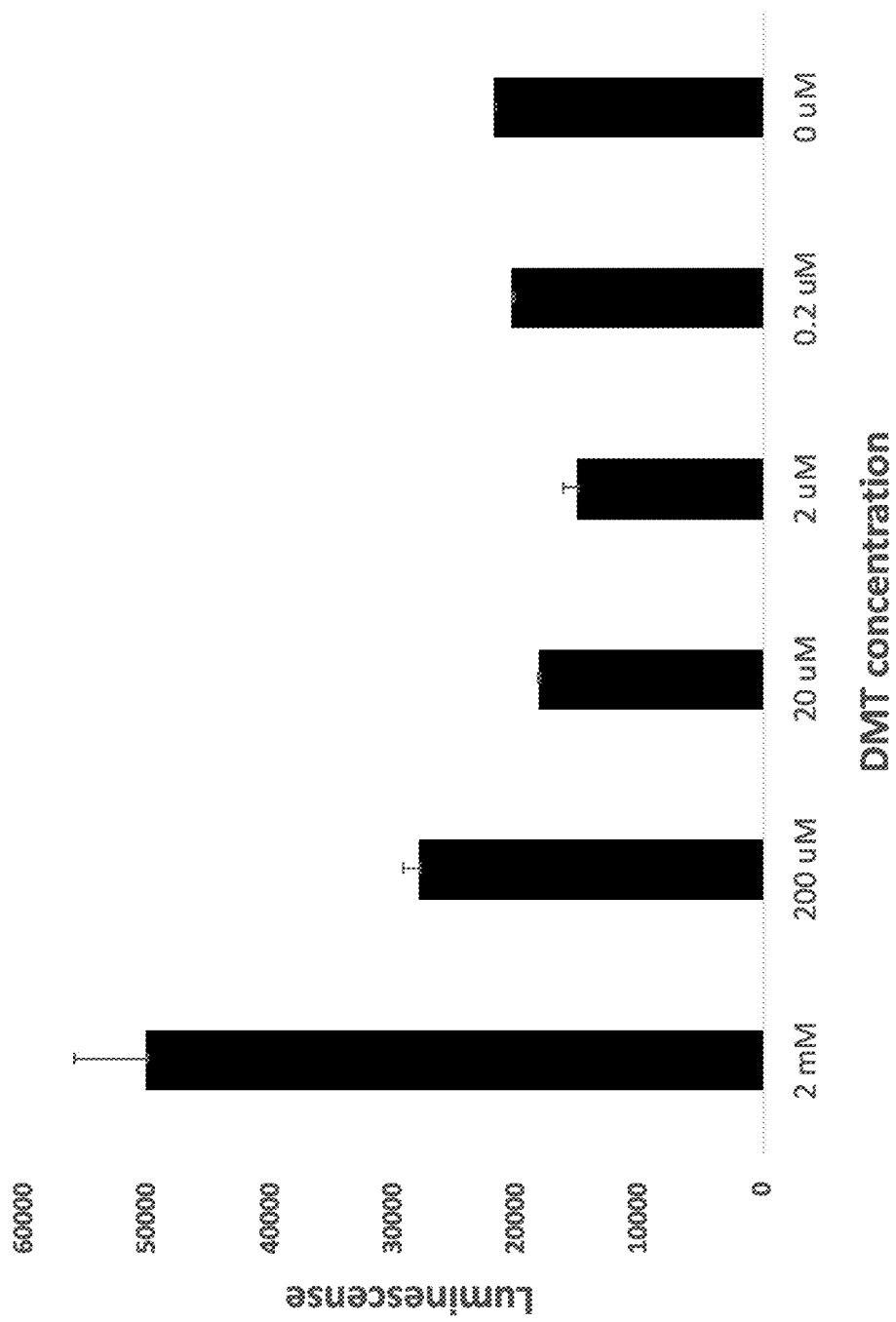
Figure 14E:
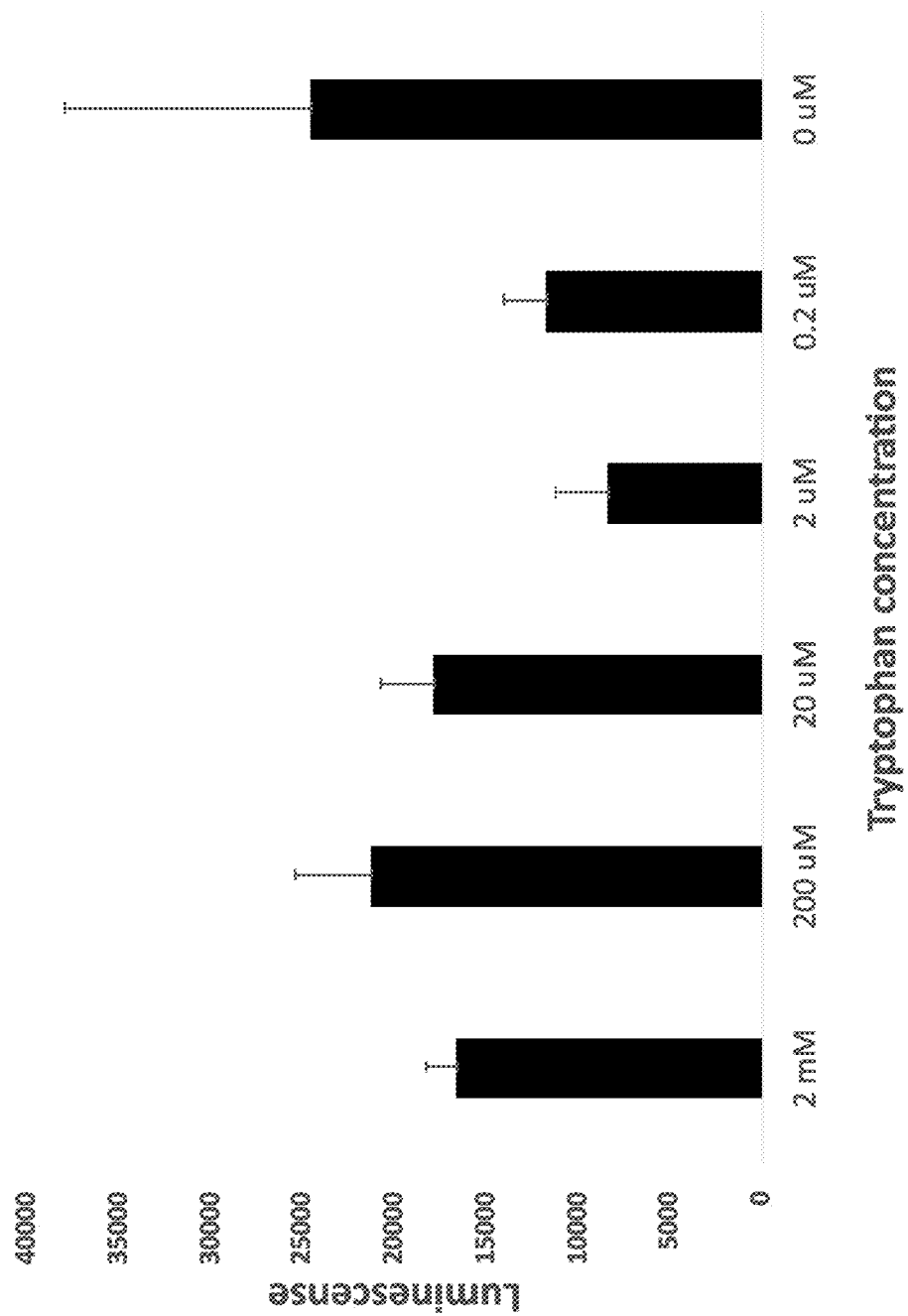
Figure 14F:
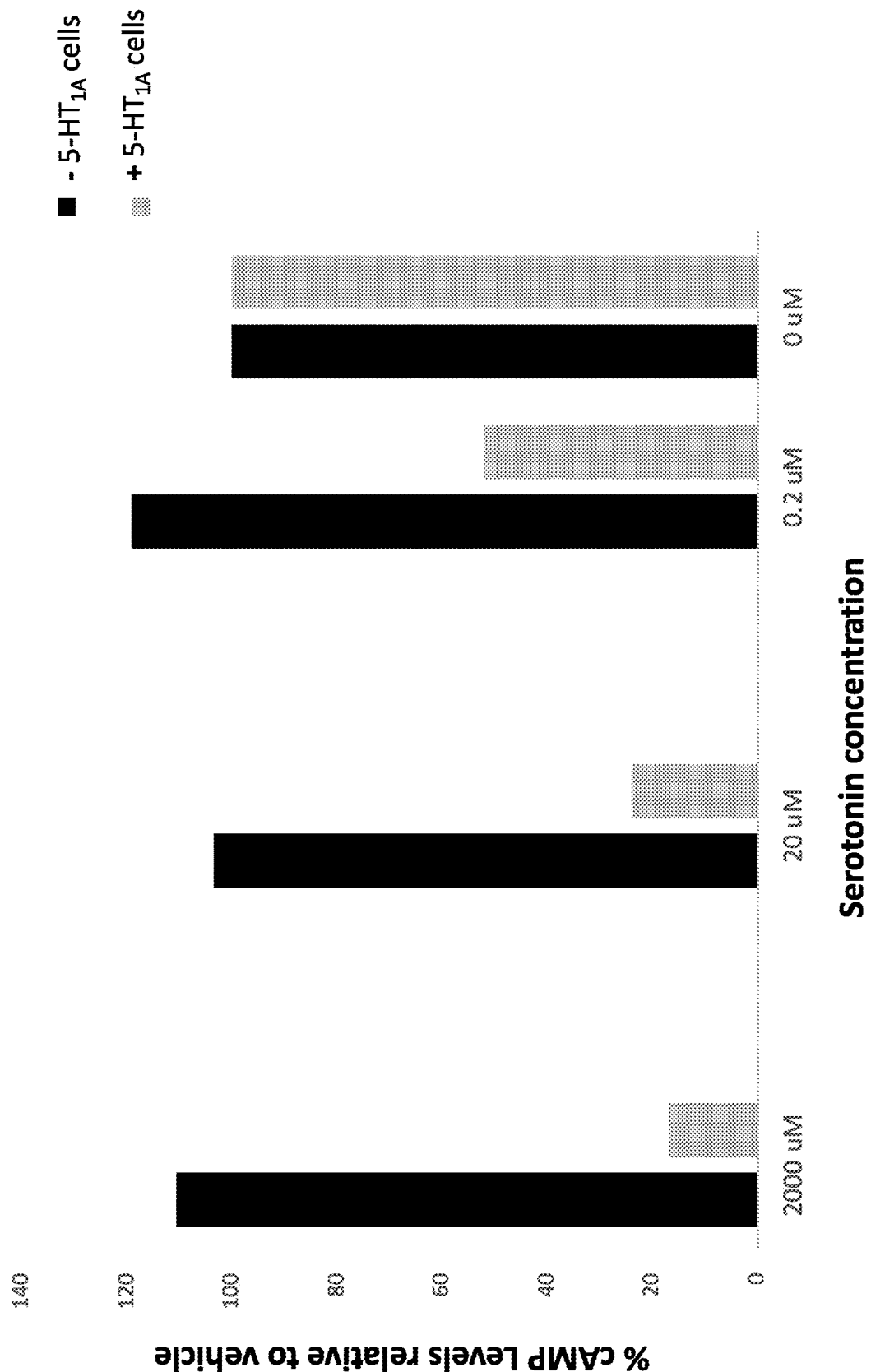
Figure 14G:
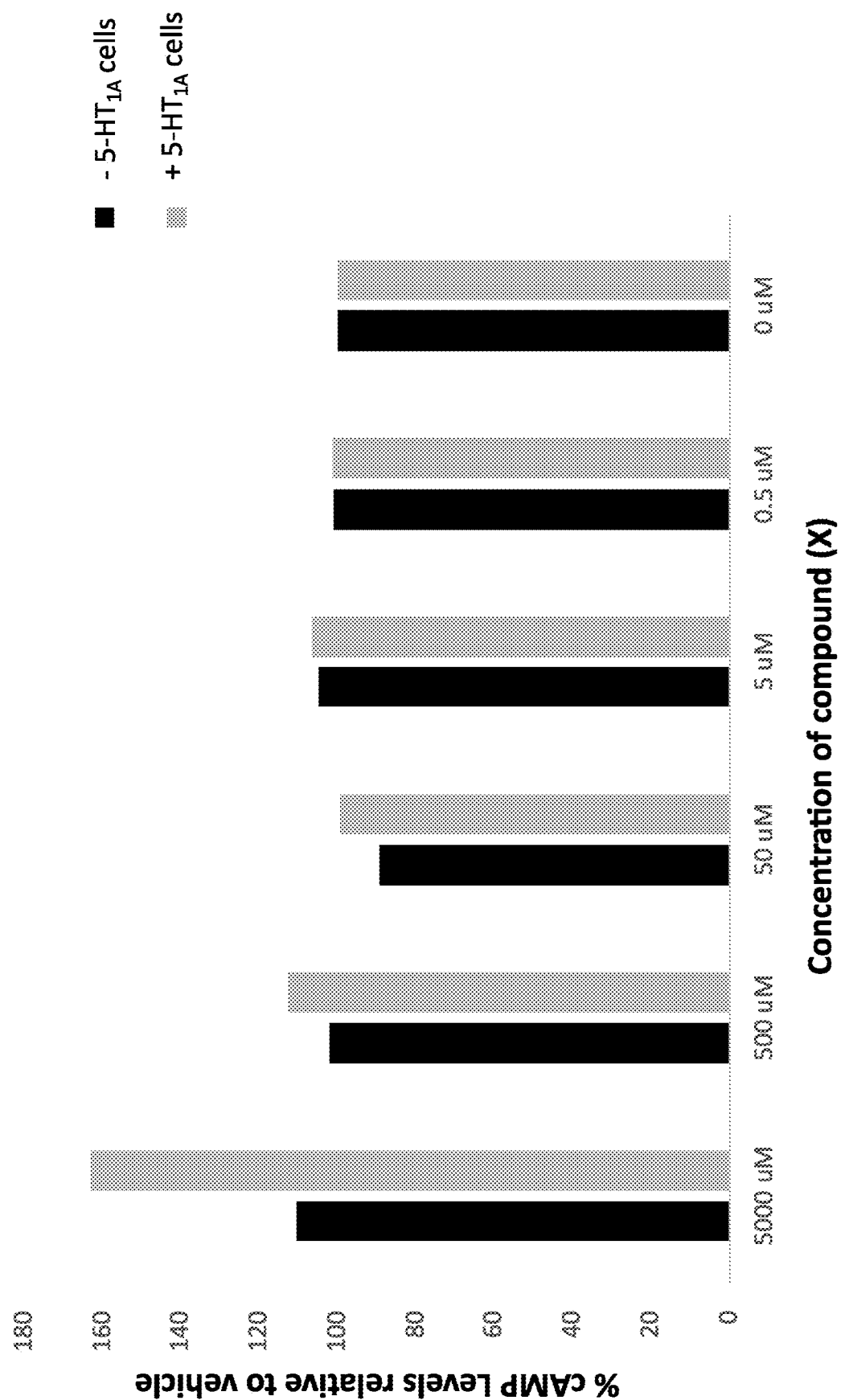

14A), a radioligand competition assay at the 5-HT$_{2A}$ receptor (FIG. 14B), a luminescence assay in +5HT$_{1A}$ cell cultures at various forskolin concentrations (FIG. 14C), a luminescence assay in +5HT$_{1A}$ cell cultures in the presence of constant (4 µM) forskolin but with decreasing DMT concentration (FIG. 14D), a luminescence assay in +5HT$_{1A}$ cell cultures in the presence of constant (4 µM) forskolin but with decreasing tryptophan concentration (FIG. 14E), a cAMP assay in the presence of constant (4 µM) forskolin but with decreasing serotonin concentration in +5HT$_{1A}$ cells (FIG. 14F), a cAMP assay in the presence of constant (4 µM) forskolin but with increasing concentration of an aldehyde psilocybin compound having formula (X), designated "X" in +5HT$_{1A}$ cells and −5HT$_{1A}$ cells (FIG. 14G).

Figure 15A:
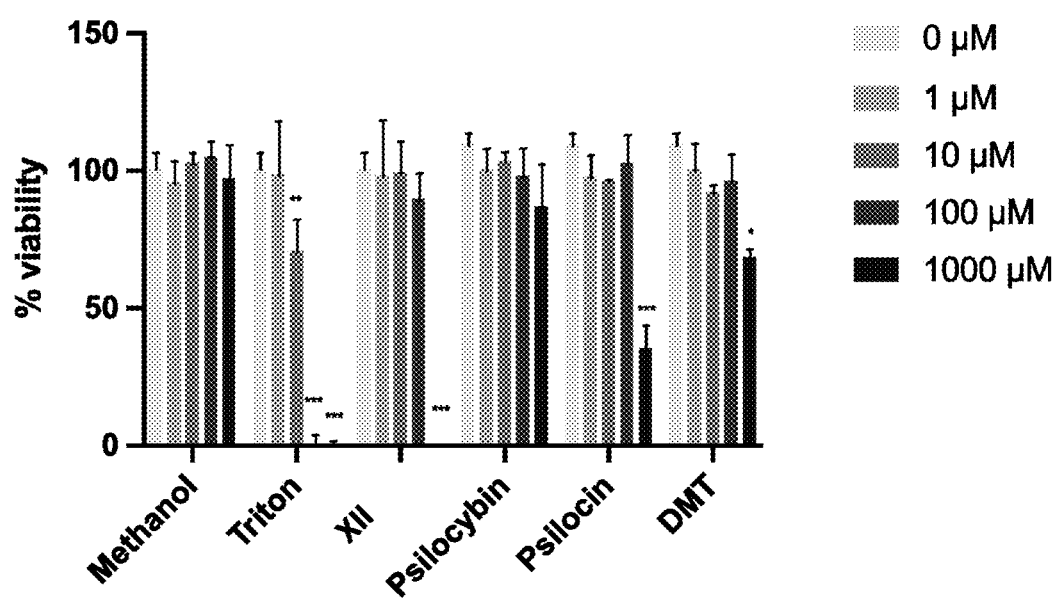
Figure 15B:
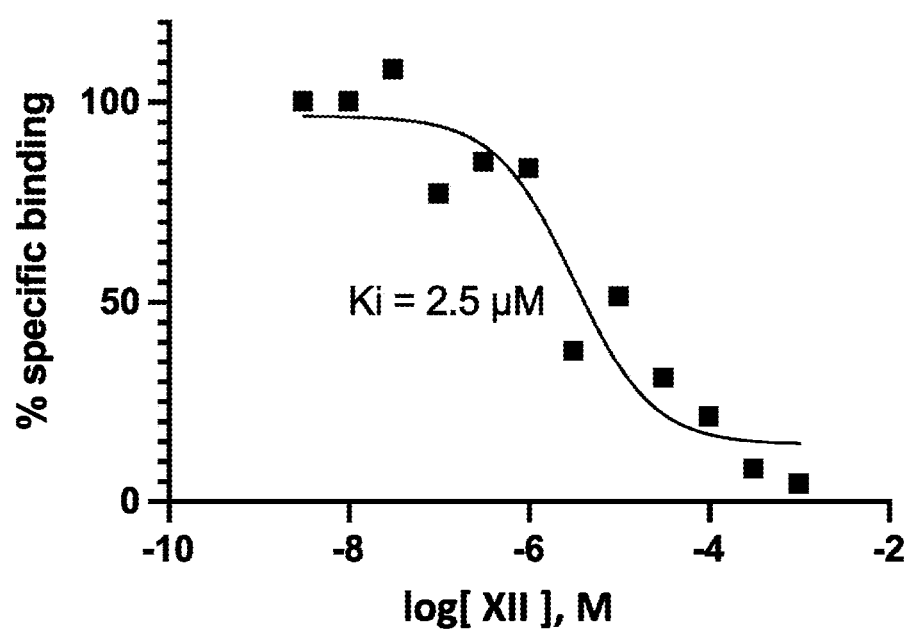
Figure 15C:
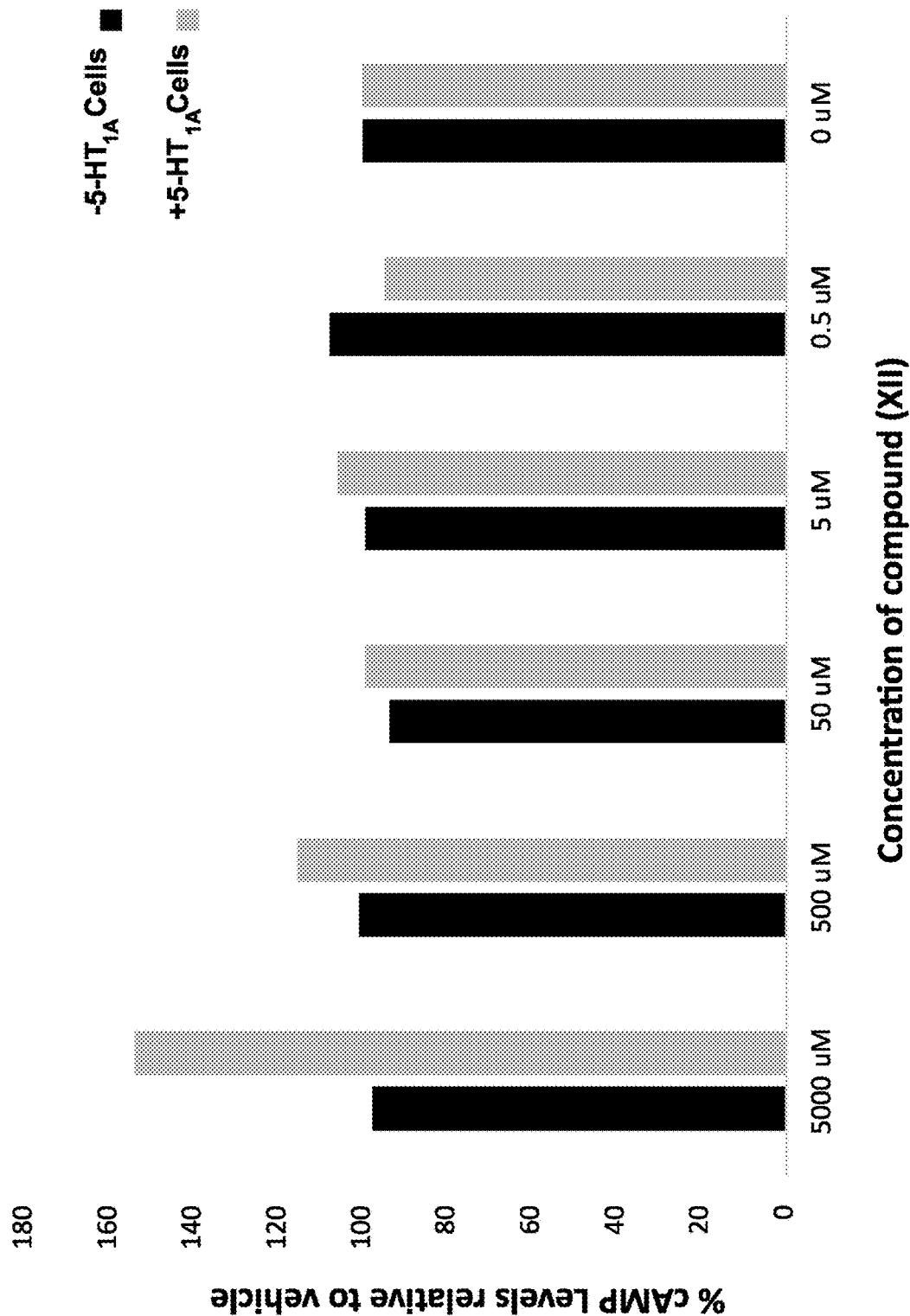

FIGS. 15A, 15B and 15C depict various further graphs, obtained in the performance of experimental assays to evaluate the efficacy of an example aldehyde psilocybin derivative having the chemical formula (XII) set forth herein, notably a cell viability assay (FIG. 15A), a radioligand competition assay at the 5-HT$_{2A}$ receptor (FIG. 15B), a cAMP assay in the presence of constant (4 µM) forskolin but with increasing concentration of an aldehyde psilocybin compound having formula (XII), designated "XII" in +5HT$_{1A}$ cells and −5HT$_{1A}$ cells (FIG. 15C).

Figure 16A:
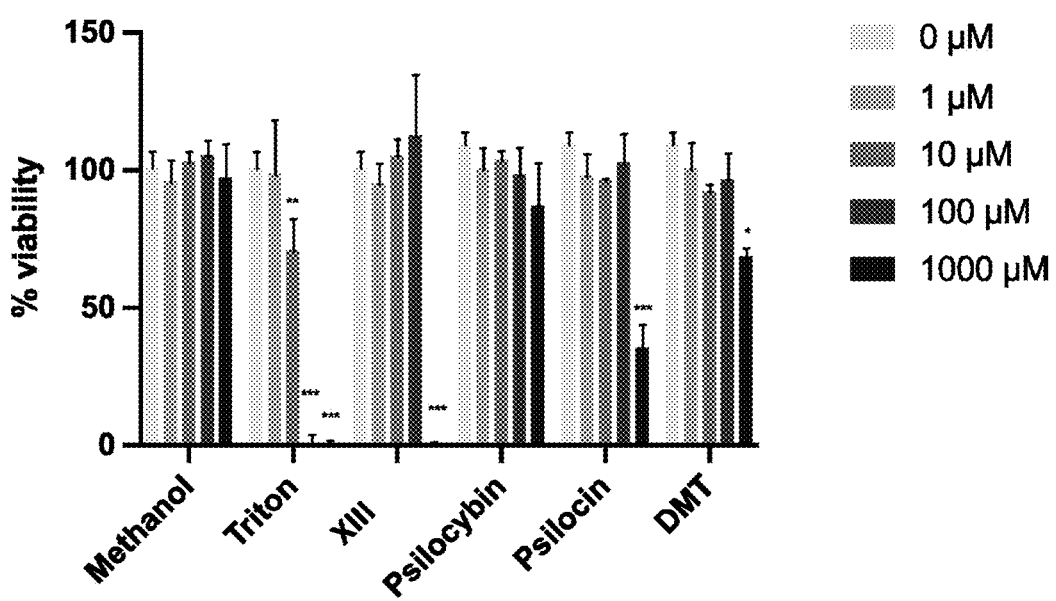
Figure 16B:
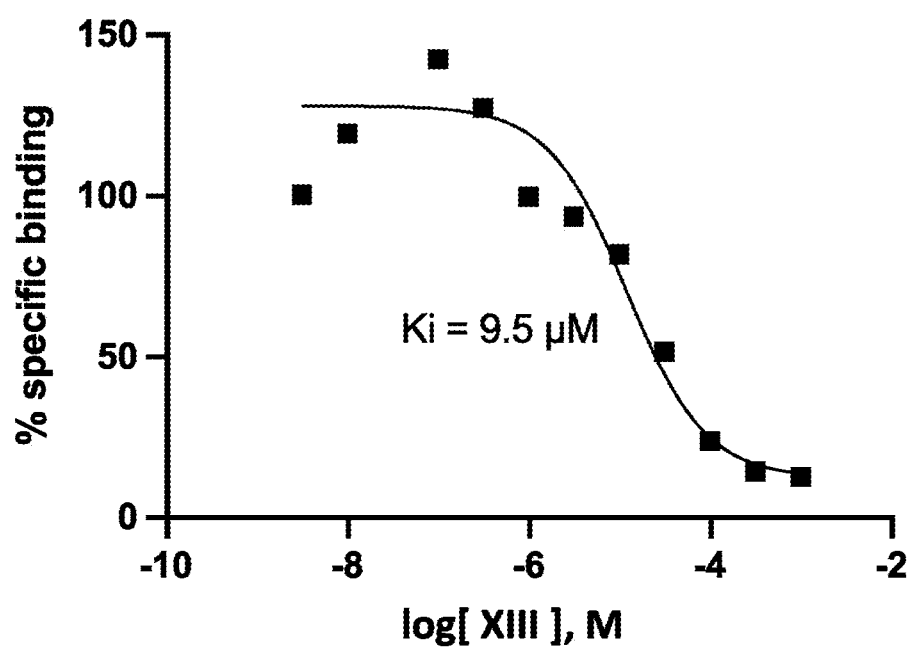
Figure 16C:
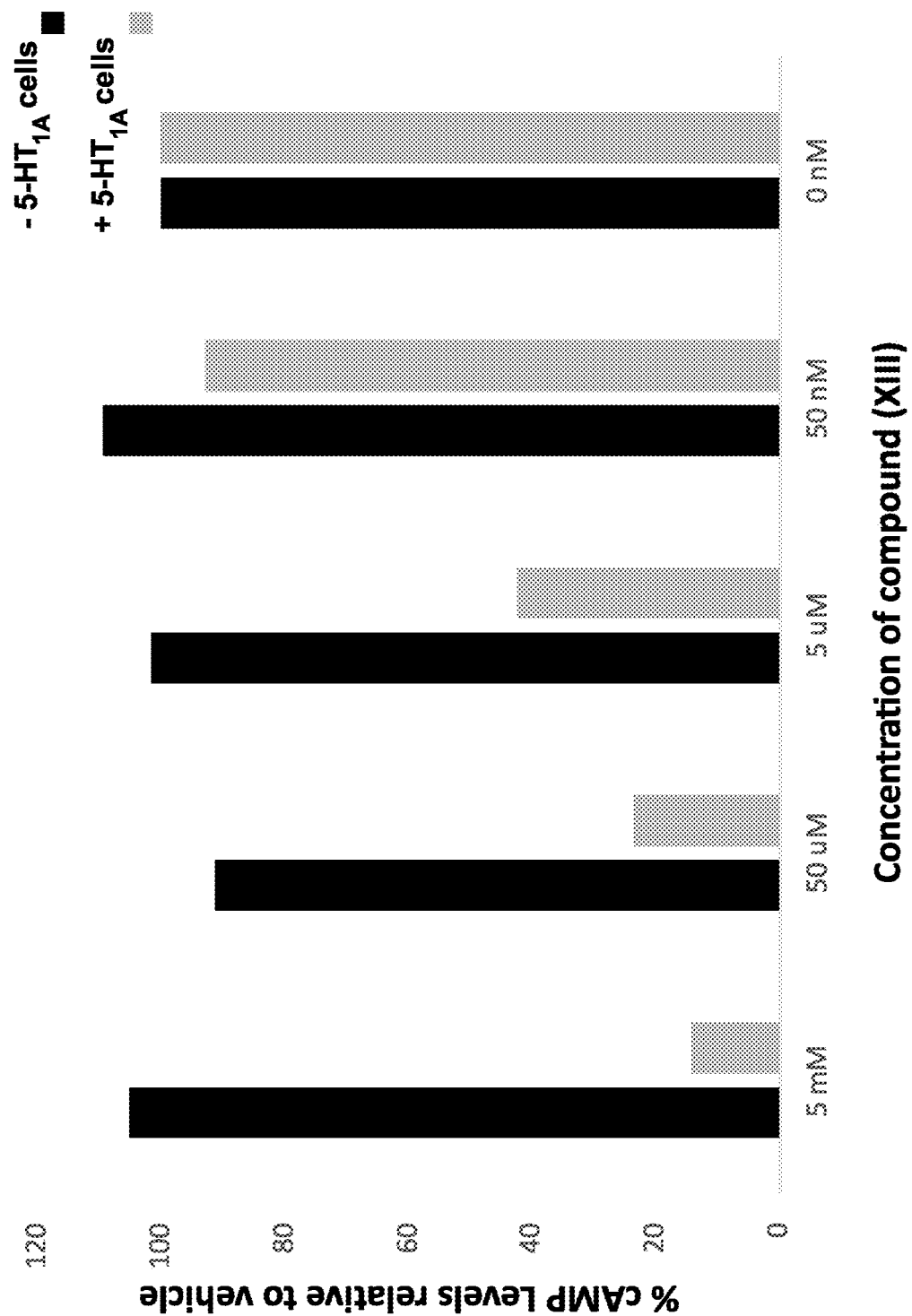

FIGS. 16A, 16B and 16C depict various further graphs, obtained in the performance of experimental assays to evaluate the efficacy of an example ketone psilocybin derivative having the chemical formula (XIII) set forth herein, notably a cell viability assay (FIG. 16A), a radioligand competition assay at the 5-HT$_{2A}$ receptor (FIG. 16B), a cAMP assay in the presence of constant (4 µM) forskolin but with increasing concentration of an aldehyde psilocybin compound having formula (XIII), designated "X" in +5HT$_{1A}$ cells and −5HT$_{1A}$ cells (FIG. 16C).

The figures together with the following detailed description make apparent to those skilled in the art how the disclosure may be implemented in practice.

DETAILED DESCRIPTION

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system, or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

As used herein and in the claims, the singular forms, such "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers.

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system, or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore any range of values described herein is intended to specifically include the limiting values of the range, and any intermediate value or sub-range within the given range, and all such intermediate values and sub-ranges are individually and specifically disclosed (e.g., a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents and patent applications are herein incorporated by reference in their entirety to the same extent as if each individual publication, patent, or patent application was specifically and individually indicated to be incorporated by reference in its entirety.

Terms and Definitions

Figure 1:
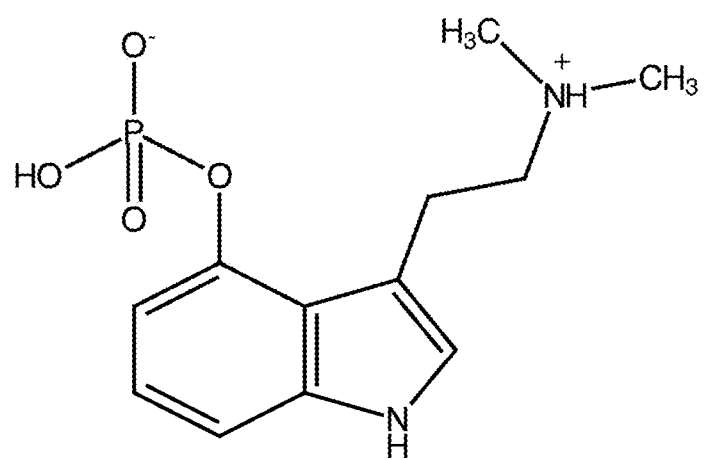
FIG. 1 depicts the chemical structure of psilocybin.

The term "psilocybin", refers to a chemical compound having the structure set forth in FIG. 1.

Figure 2:
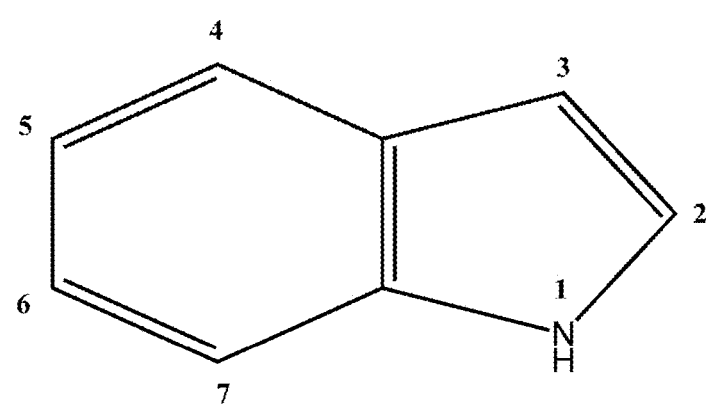
FIG. 2 depicts a certain prototype structure of psilocybin and psilocybin derivative compounds, namely an indole. Certain carbon and nitrogen atoms may be referred to herein by reference to their position within the indole structure, i.e., $N_1$, $C_2$, $C_3$ etc. The pertinent atom numbering is shown.

The term "indole prototype structure" refers to the chemical structure shown in FIG. 2. It is noted that specific carbon atoms and a nitrogen atom in the indole prototype structure are numbered. Reference may be made to these carbon and nitrogen numbers herein, for example $C_2$, $C_4$, $N_1$, and so forth. Furthermore, reference may be made to chemical groups attached to the indole prototype structure in accordance with the same numbering, for example $R_4$ and $R_6$ reference chemical groups attached to the C4 and C6 atom, respectively. In addition, $R_{3A}$ and $R_{3B}$, in this respect, reference chemical groups extending from the ethyl-amino group extending in turn from the C3 atom of the prototype indole structure.

The terms "aldehyde" or "aldehyde group", as used herein, refers to a molecule containing one atom of carbon double bonded to an oxygen atom, and bonded to a hydrogen atom, and having the chemical formula:

which may, further alternatively be represented herein as —CHO. A —CHO group may also by referred to herein as a formyl group. It is to be understood that an aldehyde through its carbon atom may be chemically bonded to another entity.

The terms "ketone" or "ketone group", as used herein, refer to a molecule containing at least two atoms of carbon, a first carbon atom double bonded to an oxygen atom, and the first carbon further bonded to a second carbon atom, the molecule having the chemical formula:

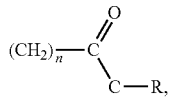

wherein R is any entity or plurality of entities which taken together allow the carbon atom bonded to R to achieve its ordinary valency, and wherein n is a positive integer, including 0, including for example, 0, 1, 2, 3, 4, 5, 6, 7, 8, 9 or 10. Thus, for example, R may represent 3 hydrogen atoms, or R may represent 2 hydrogen atoms and an alkyl group, including a straight chain alkyl group (e.g., methyl, ethyl, propyl, butyl etc.) or a branched chain alkyl group, or R may represent 3 halogen atoms, 2 halogen atoms and a hydrogen atom, or one halogen atom and 2 hydrogen atoms. It is to be understood that a ketone through its first carbon atom may be chemically bonded to another entity.

The term "aldehyde psilocybin derivative", as used herein, refers to a psilocybin derivative compound in which an aldehyde group has been bonded to psilocybin or a psilocybin derivative. Reference may be made to specific carbon atoms which may possess an aldehyde group. For example, a 5-formyl-psilocybin derivative refers to a psilocybin derivative in which carbon atom number 5 (as identified in the indole prototype structure) possesses a formyl (i.e., aldehyde) group, or, similarly, 7-formyl-psilocybin derivative refers to a psilocybin derivative in which carbon atom number 7 (as identified in the indole prototype structure) possesses a formyl group. Thus, for example, aldehyde psilocybin derivatives include, single aldehyde derivatives, 2-formyl, 4-formyl, 5-formyl, 6-formyl, and 7-formyl psilocybin derivatives, for example, and multiple aldehyde derivatives, such as, for example, 5,7-di-formyl psilocybin derivatives, and 2,5,7-tri-formylpsilocybin derivatives. The term aldehyde psilocybin derivatives further includes derivatives wherein the aldehyde group has the chemical formula (IV):

and psilocybin derivatives wherein the aldehyde group has the chemical formula (V):

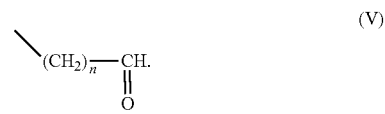

The term aldehyde psilocybin derivatives further includes chemical compounds having the chemical formula (I):

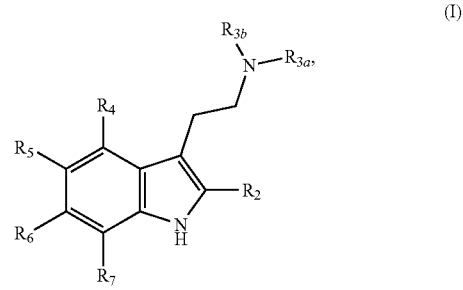

wherein, at least one of $R_2$, $R_5$, $R_6$, or $R_7$ is an aldehyde group, and wherein each $R_2$, $R_5$, $R_6$, or $R_7$ which is not an aldehyde group, is a hydrogen atom, an alkyl group, or O-alkyl group, wherein $R_4$ is an O-alkyl group, an O-acyl group, an O-aryl group, an O-alkaryl group, a hydroxy group, a phosphate group, a glycosyloxy group, or a hydrogen atom and wherein $R_{3A}$ and $R_{3B}$ are a hydrogen atom, an alkyl group, acyl group or an aryl group. Furthermore, it is noted that when $R_4$ is a phosphate group, the term aldehyde psilocybin derivatives includes compounds having the chemical formula (VII):

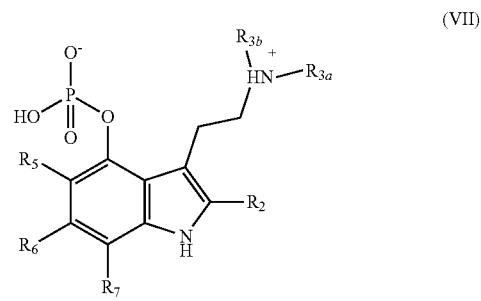

wherein, at least one of $R_2$, $R_5$, $R_6$, or $R_7$ is an aldehyde group, and wherein each $R_2$, $R_5$, $R_6$, or $R_7$ which is not an aldehyde group, is a hydrogen atom, an alkyl group, or O-alkyl group, wherein $R_4$ is an O-alkyl group, an O-acyl group, an O-aryl group, an O-alkaryl group, a hydroxy group, a phosphate group, a glycosyloxy group, or a hydrogen atom and wherein $R_{3A}$ and $R_{3B}$ each independently are a hydrogen atom, an alkyl group, acyl group or an aryl group. The term further includes salts of aldehyde psilocybin derivatives, such as a sodium salt, a potassium salt etc.

The term "ketone psilocybin derivative", as used herein, refers to a psilocybin derivative compound in which a ketone group has been bonded to psilocybin or a psilocybin derivative. Reference may be made to specific carbon atoms which may possess a ketone group. For example, a 5-ketone-psilocybin (or using alternative nomenclature, a 5-acyl-psilocybin) derivative refers to a psilocybin derivative in which carbon atom number 5 (as identified in the indole prototype structure) possesses a ketone group, or, similarly, 7-ketone-psilocybin derivative refers to a psilocybin derivative in which carbon atom number 7 (as identified in the indole prototype structure) possesses a ketone group. Thus, for example, ketone psilocybin derivatives include, single ketone derivatives, 2-ketone, 4-ketone, 5-ketone, 6-ketone, and 7-ketone psilocybin derivatives, for example, and multiple ketone derivatives, such as, for example, 5,7-di-ketone psilocybin derivatives, and 2,5,7-tri-ketone-psilocybin derivatives. The term ketone psilocybin derivatives further includes derivatives wherein the ketone group has the chemical formula (II):

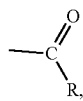

(II)

wherein R is an alkyl group, a halogenated alkyl group, or an aryl group, and derivatives wherein, the ketone group has the chemical formula (III):

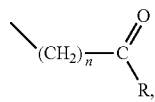

(III)

wherein R is an alkyl group, a halogenated alkyl group or an aryl group, and wherein when R is an alkyl group or alkaryl group n is an integer from 1 to 10, or wherein when R is a halogenated alkyl group (where the halogen is F, Cl, Br, or I), n is an integer from 0-10. The term ketone psilocybin derivatives further includes chemical compounds having the chemical formula (I):

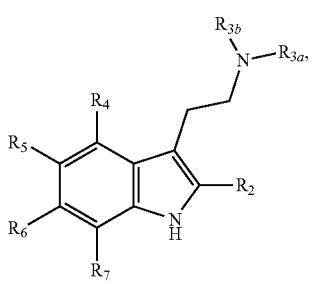

(I)

wherein, at least one of $R_2$, $R_5$, $R_6$, or $R_7$ is a ketone group (or acyl group), and wherein each $R_2$, $R_5$, $R_6$, or $R_7$ which is not a ketone group, is a hydrogen atom, an alkyl group, or O-alkyl group, wherein $R_4$ is an O-alkyl group, an O-acyl group, an O-aryl group, an O-alkaryl group, a hydroxy group, a phosphate group, a glycosyloxy group, or a hydrogen atom and wherein $R_{3A}$ and $R_{3B}$ each independently are a hydrogen atom, an alkyl group, acyl group or an aryl group. Furthermore, it is noted that when $R_4$ is a phosphate group, the term ketone psilocybin derivatives includes compounds having the chemical formula (VII):

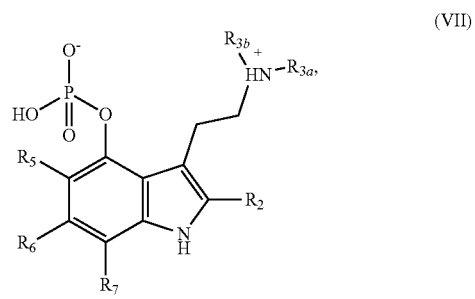

(VII)

wherein, at least one of $R_2$, $R_5$, $R_6$, or $R_7$ is a ketone group, and wherein each $R_2$, $R_5$, $R_6$, or $R_7$ which is not a ketone group, is a hydrogen atom, an alkyl group, or O-alkyl group, wherein $R_4$ is an O-alkyl group, an O-acyl group, an O-aryl group, an O-alkaryl group, a hydroxy group, a phosphate group, a glycosyloxy group, or a hydrogen atom and wherein $R_{3A}$ and $R_{3B}$ each independently are a hydrogen atom, an alkyl group, acyl group or an aryl group. The term further includes salts of ketone psilocybin derivatives, such as a sodium salt, a potassium salt etc.

The term "phosphate group", as used herein, is a molecule containing one atom of phosphorus, covalently bound to four oxygen atoms (three single bonds and one double bond). Of the four oxygen atoms one oxygen atom may be a hydroxy group, and one of the non-hydroxylated oxygen atom may be chemically bonded to another entity.

The terms "hydroxy group", and "hydroxy", as used herein refers to a molecule containing one atom of oxygen bonded to one atom of hydrogen, and having the chemical formula —OH. A hydroxy group through its oxygen atom may be chemically bonded to another entity.

The terms "glycosylated" or "glycosyl", as used herein, refer to a saccharide group, such as a mono-, di-, tri- oligo- or a poly-saccharide group, which can be or has been bonded from its anomeric carbon either in the pyranose or furanose form, either in the α or the β conformation. When bonded through its anomeric carbon via an oxygen atom to another entity, the bonded saccharide group, inclusive of the oxygen atom, may be referred to herein as a "glycosyloxy" group. Example monosaccharide groups include, but are not limited to, a pentosyl, a hexosyl, or a heptosyl group. The glycosyloxy group may also be substituted with various groups. Such substitutions may include lower alkyl, lower alkoxy, acyl, carboxy, carboxyamino, amino, acetamido, halo, thio, nitro, keto, and phosphatyl groups, wherein the substitution may be at one or more positions on the saccharide. Included in the term glycosyl are further stereoisomers, optical Isomers, anomers, and epimers of the glycosyloxy group. Thus, a hexose group, for example, can be either an aldose or a ketose group, can be of D- or L-configuration, can assume either an α or β conformation, and can be a dextro- or levo-rotatory with respect to plane-polarized light. Example glycosyloxy groups further include, without limitation, glucosyl groups, glucuronic add groups, galactosyl groups, fucosyl groups, xylose groups, arabinose groups, and rhamnose groups.

The term "alkyl group" refers to a straight and/or branched chain, saturated alkyl radical containing from one to "p" carbon atoms ("$C_1$-$C_p$-alkyl") and includes, depending on the identity of "p", methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl, and the like; where the variable p is an integer representing the largest number of carbon atoms in the alkyl radical. Alkyl groups further include hydrocarbon groups arranged in a chain having the chemical formula —$C_nH_{2n+1}$, including, without limitation, methyl groups (—$CH_3$), ethyl groups (—$C_2H_5$), propyl groups (—$C_3H_7$), and butyl groups (—$C_4H_9$).

The term "halogenated alkyl group" refers to a straight and/or branched chain, saturated alkyl radical containing from one to "p" carbon atoms ("$C_1$-$C_p$-alkyl") and includes, depending on the identity of "p", methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl, and the like, where the variable p is an integer representing the largest number of carbon atoms in the alkyl radical, and wherein from one to all of the hydrogen atoms are replaced with halogen atoms, such as F, Cl, I or Br. Alkyl groups further include hydrocarbon groups substituted with halogen atoms arranged in a chain having the chemical formula —$C_nH_{2n+1}$, including, without limitation, methyl groups (—$CH_3$), ethyl groups (—$C_2H_5$), propyl groups (—$C_3H_7$), and butyl groups (—$C_4H_9$).

The term "O-alkyl group", refers to a hydrocarbon group arranged in a chain having the chemical formula —O—$C_nH_{2n+1}$. O-alkyl groups include, without limitation, O-methyl groups (—O—$CH_3$), O-ethyl groups (—O—$C_2H_5$), O-propyl groups (—O—$C_3H_7$) and O-butyl groups (—O—$C_4H_9$).

The term "acyl group" refers to a carbon atom double bonded to an oxygen and single bonded to an alkyl group. The carbon atom further can be bonded to another entity. An acyl group can be described by the chemical formula: —C(=O)—$C_nH_{2n+1}$.

The term "O-acyl group" refers to an acyl group in which the carbon atom is single bonded to an additional oxygen atom. The additional oxygen atom can be bonded to another entity. An O-acyl group can be described by the chemical formula: —O—C(=O)—$C_nH_{2n+1}$. Furthermore, depending on the carbon chain, length specific O-acyl groups may be termed an acetyl group (n=1), a propionoyl group (n=2), butyryl group (n=3), a pentanoyl group (n=4) etc.

The term "aryl", as used herein, refers to a monocyclic, bicyclic; or tricyclic aromatic ring system containing, depending on the number of atoms in the rings; for example, from 6 to 14 carbon atoms ($C_6$-$C_{14}$-aryl) or from 6 to 10 carbons ($C_6$-$C_{10}$-aryl), and at least 1 aromatic ring and includes phenyl; alkyl phenyl, benzyl naphthyl, anthracenyl, 1,2-dihydronaphthyl, 1,2,3,4-tetrahydronaphthyl, fluorenyl, phenanthrenyl, biphenylenyl, indanyl, indenyl and the like.

The term "O-aryl", as used herein, refers to a monocyclic, bicyclic, or tricyclic; aromatic ring system containing; depending on the number of atoms in the rings, for example, from 6 to 14 carbon atoms ($C_6$-$C_{14}$—O-aryl) or from 6 to 10 carbons ($C_6$-$C_{10}$—O-aryl), and at least 1 aromatic ring, attached to which is an oxygen atom. When the moiety is bonded through or an O-alkyl group; the moiety is a "—O-alkaryl" group in which the oxygen atom is bonded to the aryl group through a carbon atom (e.g., —$CH_2O$—; —$CH_2$—$CH_2O$—; or —$CH_2$—$CH_2$—$CH_2O$—). The oxygen atom can be bonded to another entity.

The term "halogen", "halogenated" and "halo-", as used herein, refers to the class of elements consisting of fluorine (F), chlorine (Cl), bromine (Br), and iodine (I). Accordingly, halogenated compounds can refer to "fluorinated", "chlorinated", "brominated", or "iodinated" compounds.

The term "5-$HT_{2A}$ receptor", as used herein, refers to a subclass of a family of receptors for the neurotransmitter and peripheral signal mediator serotonin. 5-$HT_{2A}$ receptors can mediate a plurality of central and peripheral physiologic functions of serotonin. Central nervous system effects can include mediation of hallucinogenic effects of hallucinogenic compounds.

The term "modulating 5-$HT_{2A}$ receptors", as used herein, refers to the ability of a compound disclosed herein to alter the function of 5-$HT_{2A}$ receptors. A 5-$HT_{2A}$ receptor modulator may activate the activity of a 5-$HT_{2A}$ receptor, may activate or inhibit the activity of a 5-$HT_{2A}$ receptor depending on the concentration of the compound exposed to the 5-$HT_{2A}$ receptor, or may inhibit the activity of a 5-$HT_{2A}$ receptor. Such activation or inhibition may be contingent on the occurrence of a specific event, such as activation of a signal transduction pathway, and/or may be manifest only in particular cell types. The term "modulating 5-$HT_{2A}$ receptors," also refers to altering the function of a 5-$HT_{2A}$ receptor by increasing or decreasing the probability that a complex forms between a 5-$HT_{2A}$ receptor and a natural binding partner to form a multimer. A 5-$HT_{2A}$ receptor modulator may increase the probability that such a complex forms between the 5-$HT_{2A}$ receptor and the natural binding partner, may increase or decrease the probability that a complex forms between the 5-$HT_{2A}$ receptor and the natural binding partner depending on the concentration of the compound exposed to the 5-$HT_{2A}$ receptor, and or may decrease the probability that a complex forms between the 5-$HT_{2A}$ receptor and the natural binding partner.

The term "5-$HT_{2A}$ receptor-mediated disorder", as used herein, refers to a disorder that is characterized by abnormal 5-$HT_{2A}$ receptor activity. A 5-$HT_{2A}$ receptor-mediated disorder may be completely or partially mediated by modulating 5-$HT_{2A}$ receptors. In particular, a 5-$HT_{2A}$ receptor-mediated disorder is one in which modulation of 5-$HT_{2A}$ receptors results in some effect on the underlying disorder e.g., administration of a 5-$HT_{2A}$ receptor modulator results in some improvement in at least some of the subjects being treated.

The term "5-$HT_{1A}$ receptor", as used herein, refers to a subclass of a family of receptors for the neurotransmitter and peripheral signal mediator serotonin. 5-$HT_{1A}$ receptors can mediate a plurality of central and peripheral physiologic functions of serotonin. Ligand activity at 5-$HT_{1A}$ is generally not associated with hallucination, although many hallucinogenic compounds are known to modulate 5-$HT_{1A}$ receptors to impart complex physiological responses (Inserra et al., 2020, Pharmacol Rev 73: 202).

The term "modulating 5-$HT_{1A}$ receptors", as used herein, refers to the ability of a compound disclosed herein to alter the function of 5-$HT_{1A}$ receptors.

A 5-$HT_{1A}$ receptor modulator may activate the activity of a 5-$HT_{1A}$ receptor, may activate or inhibit the activity of a 5-$HT_{1A}$ receptor depending on the concentration of the compound exposed to the 5-$HT_{1A}$ receptor, or may inhibit the activity of a 5-$HT_{1A}$ receptor. Such activation or inhibition may be contingent on the occurrence of a specific event, such as activation of a signal transduction pathway, and/or may be manifest only in particular cell types. The term "modulating 5-HT$_{1A}$ receptors," also refers to altering the function of a 5-HT$_{1A}$ receptor by increasing or decreasing the probability that a complex forms between a 5-HT$_{1A}$ receptor and a natural binding partner to form a multimer. A 5-HT$_{1A}$ receptor modulator may increase the probability that such a complex forms between the 5-HT$_{1A}$ receptor and the natural binding partner, may increase or decrease the probability that a complex forms between the 5-HT$_{1A}$ receptor and the natural binding partner depending on the concentration of the compound exposed to the 5-HT$_{1A}$ receptor, and or may decrease the probability that a complex forms between the 5-HT$_{1A}$ receptor and the natural binding partner.

The term "5-HT$_{1A}$ receptor-mediated disorder", as used herein, refers to a disorder that is characterized by abnormal 5-HT$_{1A}$ receptor activity. A 5-HT$_{1A}$ receptor-mediated disorder may be completely or partially mediated by modulating 5-HT$_{1A}$ receptors. In particular, a 5-HT$_{1A}$ receptor-mediated disorder is one in which modulation of 5-HT$_{1A}$ receptors results in some effect on the underlying disorder e.g., administration of a 5-HT$_{1A}$ receptor modulator results in some improvement in at least some of the subjects being treated.

The term "pharmaceutical formulation", as used herein, refers to a preparation in a form which allows an active ingredient, including a psychoactive ingredient, contained therein to provide effective treatment, and which does not contain any other ingredients which cause excessive toxicity, an allergic response, irritation, or other adverse response commensurate with a reasonable risk/benefit ratio. The pharmaceutical formulation may contain other pharmaceutical ingredients such as excipients, carriers, diluents, or auxiliary agents.

The term "recreational drug formulation", as used herein, refers to a preparation in a form which allows a psychoactive ingredient contained therein to be effective for administration as a recreational drug, and which does not contain any other ingredients which cause excessive toxicity, an allergic response, irritation, or other adverse response commensurate with a reasonable risk/benefit ratio. The recreational drug formulation may contain other ingredients such as excipients, carriers, diluents, or auxiliary agents.

The term "effective for administration as a recreational drug", as used herein, refers to a preparation in a form which allows a subject to voluntarily induce a psychoactive effect for non-medical purposes upon administration, generally in the form of self-administration. The effect may include an altered state of consciousness, satisfaction, pleasure, euphoria, perceptual distortion, or hallucination.

The term "effective amount", as used herein, refers to an amount of an active agent, pharmaceutical formulation, or recreational drug formulation, sufficient to induce a desired biological or therapeutic effect, including a prophylactic effect, and further including a psychoactive effect. Such effect can include an effect with respect to the signs, symptoms or causes of a disorder, or disease or any other desired alteration of a biological system. The effective amount can vary depending, for example, on the health condition, injury stage, disorder stage, or disease stage, weight, or sex of a subject being treated, timing of the administration, manner of the administration, age of the subject, and the like, all of which can be determined by those of skill in the art.

The terms "treating" and "treatment", and the like, as used herein, are intended to mean obtaining a desirable physiological, pharmacological, or biological effect, and includes prophylactic and therapeutic treatment. The effect may result in the inhibition, attenuation, amelioration, or reversal of a sign, symptom or cause of a disorder, or disease, attributable to the disorder, or disease, which includes mental and psychiatric diseases and disorders. Clinical evidence of the prevention or treatment may vary with the disorder, or disease, the subject, and the selected treatment.

The term "pharmaceutically acceptable", as used herein, refers to materials, including excipients, carriers, diluents, or auxiliary agents, that are compatible with other materials in a pharmaceutical or recreational drug formulation and within the scope of reasonable medical judgement suitable for use in contact with a subject without excessive toxicity, allergic response, irritation, or other adverse response commensurate with a reasonable risk/benefit ratio.

The terms "substantially pure" and "isolated", as may be used interchangeably herein describe a compound, e.g., a psilocybin derivative, which has been separated from components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis.

General Implementation

As hereinbefore mentioned, the present disclosure relates to psilocybin derivatives. In particular, the present disclosure provides novel aldehyde and ketone psilocybin derivatives. In general, the herein provided compositions exhibit functional properties which deviate from the functional properties of psilocybin. Thus, for example, the aldehyde and ketone psilocybin derivatives, can exhibit pharmacological properties which deviate from psilocybin. Furthermore, the aldehyde and ketone derivatives may psilocybin derivatives may exhibit physico-chemical properties which differ from psilocybin. Thus, for example, the aldehyde and ketone psilocybin derivatives may exhibit superior solubility in a solvent, for example, an aqueous solvent. The aldehyde and ketone psilocybin derivatives in this respect are useful in the formulation of pharmaceutical and recreational drug formulations. In one embodiment, the aldehyde and ketone psilocybin derivatives of the present disclosure can conveniently be biosynthetically produced. The practice of this method avoids the extraction of psilocybin from mushrooms and the performance of subsequent chemical reactions to achieve aldehyde and ketone derivatives. Furthermore, the growth of mushrooms can be avoided thus limiting the dependence on climate and weather, and potential legal and social challenges associated with the cultivation of mushrooms containing psychoactive compounds. The method can efficiently yield substantial quantities of aldehyde and ketone psilocybin derivatives.

In what follows selected embodiments are described with reference to the drawings.

Initially example aldehyde and ketone psilocybin derivatives will be described. Thereafter example methods of using and making the aldehyde and ketone psilocybin derivatives will be described.

Accordingly, in one aspect the present disclosure provides derivatives of a compound known as psilocybin of which the chemical structure is shown in FIG. 1. The derivatives herein provided are, in particular, aldehyde and ketone derivatives, including psilocybin derivatives possessing an aldehyde group or a ketone group.

Thus, in one aspect, the present disclosure provides, in accordance with the teachings herein, in at least one embodiment, a chemical compound having the chemical formula (I):

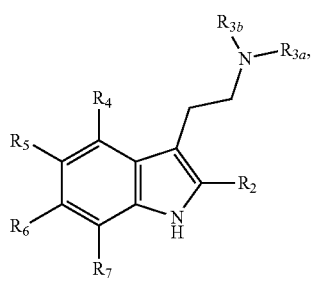

(I)

wherein, at least one of $R_2$, $R_5$, $R_6$, or $R_7$ is an aldehyde or a ketone group, and wherein each of $R_2$, $R_5$, $R_6$, or $R_7$ which is not a aldehyde group or a ketone group, is a hydrogen atom, an alkyl group, or O-alkyl group, wherein $R_4$ is an O-alkyl group, an O-acyl group, an O-aryl group, an O-alkaryl group, a hydroxy group, a phosphate group, a glycosyloxy group, or a hydrogen atom and wherein $R_{3A}$ and $R_{3B}$ each independently are a hydrogen atom, an alkyl group, acyl group or an aryl group.

Thus, referring to the chemical compound having the chemical formula (I), initially it is noted that, in an aspect hereof, at least one of $R_2$, $R_5$, $R_6$, or $R_7$ is an aldehyde group or a ketone group.

In one aspect, in an embodiment, the ketone group can have the chemical formula (II):

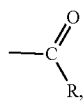

Figure 4A:
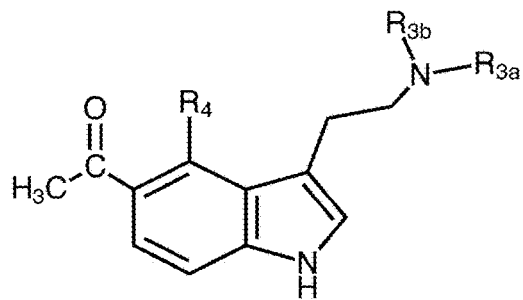
FIGS. 4A, 4B, 4C, 4D, 4E, 4F, 4G, and 4H depict the chemical structures of certain example ketone psilocybin derivatives, notably a 5-acetyl-psilocybin derivative (FIG. 4A), a 5-propionyl-ketone psilocybin derivative (FIG. 4B), a 5-benzoylpsilocybin derivative (FIG. 4C), a 5-(4-methylbenzoyl)psilocybin derivative (FIG. 4D), a 5-naphthoyl psilocybin derivative (FIG. 4E), a 5-(2-oxo-ethyl) psilocybin derivative (FIG. 4F), a 5-butyryl psilocybin derivative (FIG. 4G), and a 5-(2-oxo-3-phenyl-propyl) psilocybin derivative (FIG. 4H).
Figure 4B:
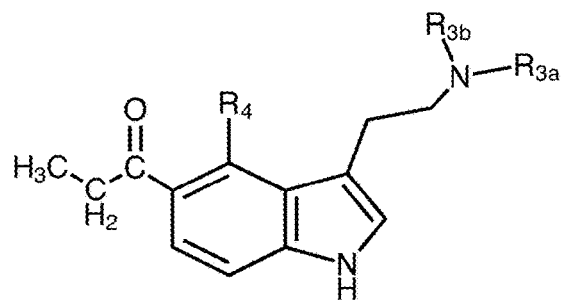

(II)

wherein R is an alkyl group or an aryl group. In one embodiment, the alkyl group in chemical formula (II) is $C_1$-$C_{20}$-alkyl or halogenated-$C_1$-$C_{20}$-alkyl. In another embodiment, the alkyl group is $C_1$-$C_{10}$-alkyl or halogenated-$C_1$-$C_{10}$-alkyl. In another embodiment, the alkyl group is $C_1$-$C_6$-alkyl or halogenated-$C_1$-$C_6$-alkyl. In another embodiment, the alkyl group is methyl, ethyl, propyl, butyl or pentyl, or the halogenated-alkyl group is trifluoromethyl. Example embodiments, wherein R in chemical formula (II) is an alkyl group are shown in FIG. 4A and FIG. 4B.

Figure 4C:
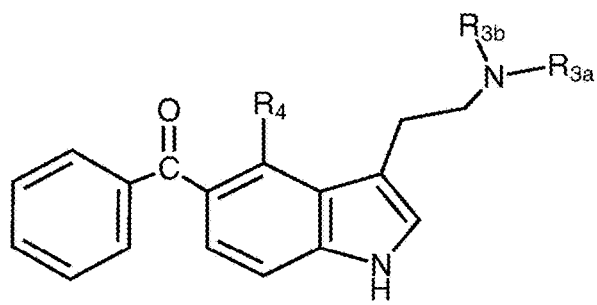
Figure 4D:
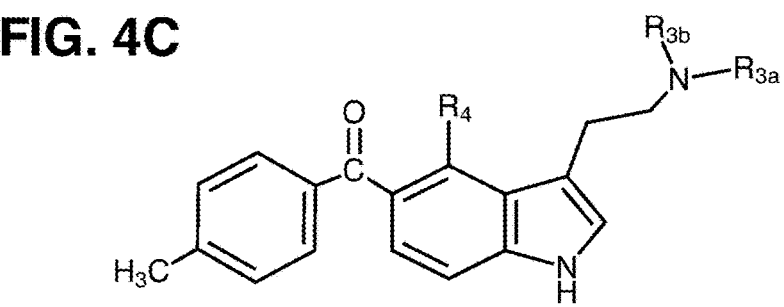
Figure 4E:
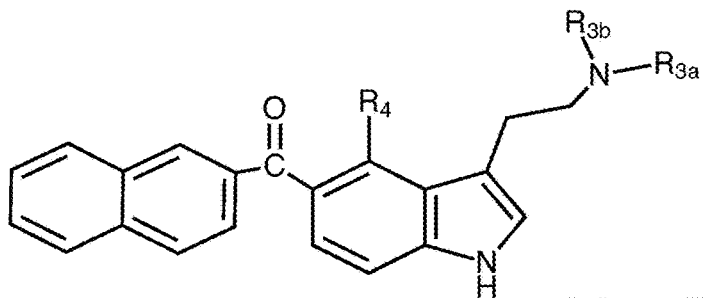

In one embodiment, the aryl group in chemical formula (II) of the disclosure is optionally substituted $C_6$-$C_{14}$-aryl. In another embodiment, the aryl group is optionally substituted $C_6$-$C_{10}$-aryl, or phenyl. In another embodiment, the aryl group is phenyl, naphthyl, tetrahydronaphthyl, phenanthrenyl, biphenylenyl, indanyl, or indenyl and the like. Example embodiments, wherein R in chemical formula (II) are an aryl group are shown in FIG. 4C, FIG. 4D and FIG. 4E.

In one aspect, in an embodiment, the ketone group has the chemical formula (III):

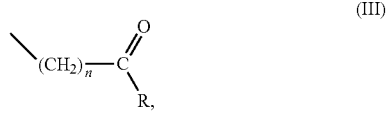

Figure 4F:
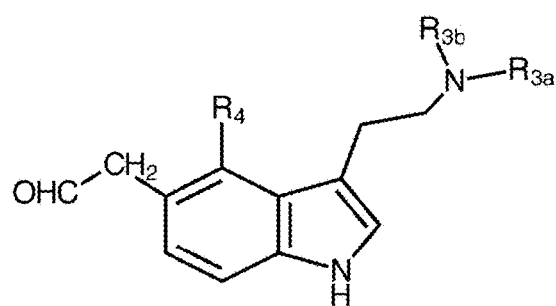
Figure 4G:
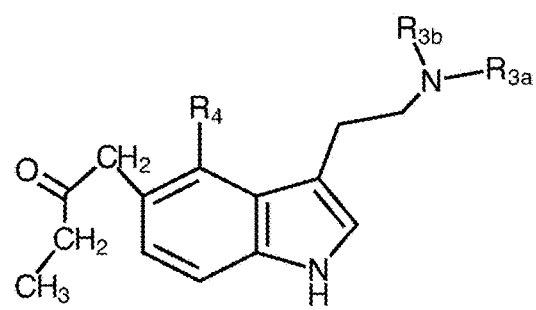

(III)

wherein R is an alkyl group or an aryl group or a halogenated alkyl group. In one embodiment, when R is an alkyl group or an aryl group, n is an integer from 1-20, i.e., n can be 1, 2, 3, 4, 5, 6, 7, 8, 9, 10, 11, 12, 13, 14, 15, 16, 17, 18, 19 or 20. In one embodiment, when R is a halogenated alkyl group, such as $CF_3$, $CHCl_2$, or $CH_2CF_3$, for example, n is an integer from 0-20, i.e., n can be 0, 1, 2, 3, 4, 5, 6, 7, 8, 9, 10, 11, 12, 13, 14, 15, 16, 17, 18, 19 or 20. In one embodiment, the alkyl group in chemical formula (III) is a $C_1$-$C_{20}$-alkyl or halogenated-$C_1$-$C_{20}$-alkyl. In another embodiment, the alkyl group is $C_1$-$C_{10}$-alkyl or halogenated-$C_1$-$C_{10}$-alkyl. In another embodiment, the alkyl group is $C_1$-$C_6$-alkyl or halogenated-$C_1$-$C_6$-alkyl. In another embodiment, the alkyl group is methyl, ethyl, propyl, butyl or pentyl, or the halogenated-alkyl group is trifluoromethyl. An example embodiment wherein R in chemical formula (III) is an alkyl group, is shown in FIG. 4G.

Figure 4H:
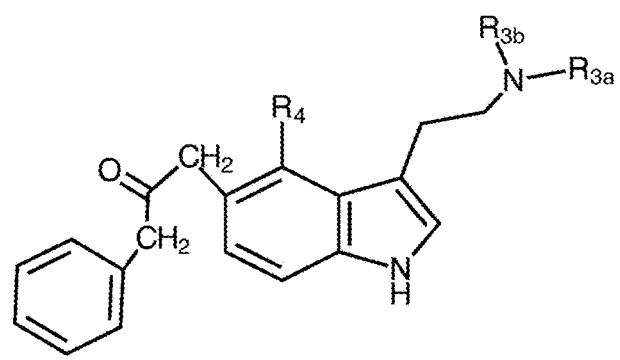

In one embodiment, the aryl groups in chemical formula (III) of the disclosure is optionally substituted $C_6$-$C_{14}$-aryl. In another embodiment, the aryl group is optionally substituted $C_6$-$C_{10}$-aryl, or phenyl. In another embodiment, the aryl group is phenyl, naphthyl, tetrahydronaphthyl, phenanthrenyl, biphenylenyl, indanyl, or indenyl and the like. An example embodiment, wherein R in chemical formula (III) is an aryl group, is shown in FIG. 4H.

In one embodiment, the aldehyde group has the chemical formula (IV):

(IV)

Example embodiments thereof are shown, for example, in FIGS. 3A-3D.

In one embodiment, the aldehyde group has the chemical formula (V):

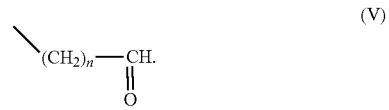

(V)

In one embodiment, n is an integer from 1-20, i.e., n can be 1, 2, 3, 4, 5, 6, 7, 8, 9, 10, 11, 12, 13, 14, 15, 16, 17, 18, 19 or 20. An example embodiment (n=1) in this respect, is shown in FIG. 4F.

In a further aspect hereof, $R_{3A}$ and $R_{3B}$ can be a hydrogen atom, an alkyl group, an acyl group, or an aryl group. Thus, $R_{3A}$ and $R_{3B}$ can each be a hydrogen atom, or $R_{3A}$ and $R_{3B}$ can each be an alkyl group, such as a methyl group, ethyl group, propyl group, or longer chain alkyl group, or $R_{3A}$ and $R_{3B}$ can be each be an acyl group, or $R_{3A}$ and $R_{3B}$ can each be an aryl group. Furthermore, one of $R_{3A}$ and $R_{3B}$ can be a hydrogen atom, and one of $R_{3A}$ and $R_{3B}$ can be an alkyl group. One of $R_{3A}$ and $R_{3B}$ can be a hydrogen atom, and one of $R_{3A}$ and $R_{3B}$ can be an acyl group. One of $R_{3A}$ and $R_{3B}$ can be a hydrogen atom, and one of $R_{3A}$ and $R_{3B}$ can be an aryl group. One of $R_{3A}$ and $R_{3B}$ can be an alkyl group, and one of $R_{3A}$ and $R_{3B}$ can be an aryl group. One of $R_{3A}$ and $R_{3B}$ can be an alkyl group, and one of $R_{3A}$ and $R_{3B}$ can be an acyl group. One of $R_{3A}$ and $R_{3B}$ can be an acyl group, and one of $R_{3A}$ and $R_{3B}$ can be an aryl group.

In a further aspect hereof, $R_4$ can be an O-alkyl group, an O-acyl group, an O-aryl group, an O-alkaryl group, a hydroxy group, a phosphate group, a glycosyloxy group, or a hydrogen atom.

Figure 3A:
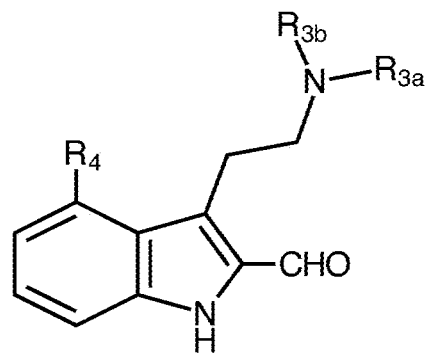
FIGS. 3A, 3B, 3C, 3D, 3E, 3F, 3G, and 3H depict the chemical structures of certain example aldehyde and ketone psilocybin derivatives, notably a 2-formyl-psilocybin derivative (FIG. 3A), a 5-formyl-psilocybin derivative (FIG. 3B), a 6-formyl-psilocybin derivative (FIG. 3C), a 7-formyl-psilocybin derivative (FIG. 3D), a 2-ketone-psilocybin derivative (FIG. 3E), a 5-ketone-psilocybin derivative (FIG. 3F), a 6-ketone-psilocybin derivative (FIG. 3G), and a 7-ketone-psilocybin derivative (FIG. 3H).
Figure 3B:
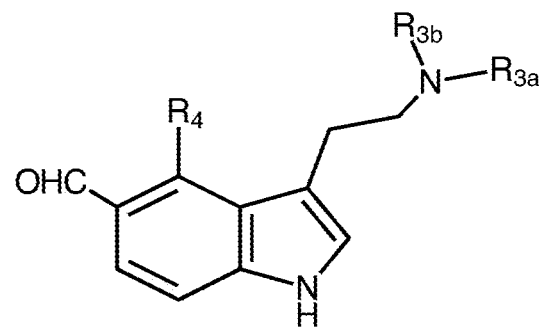
Figure 3C:
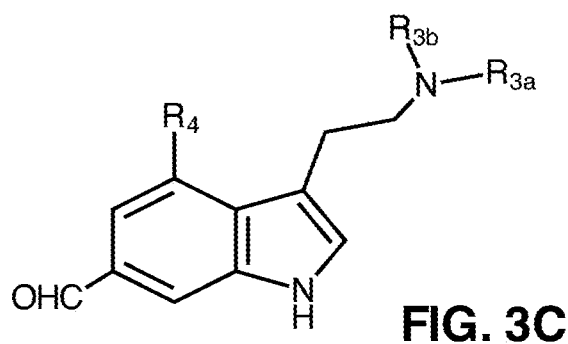
Figure 3D:
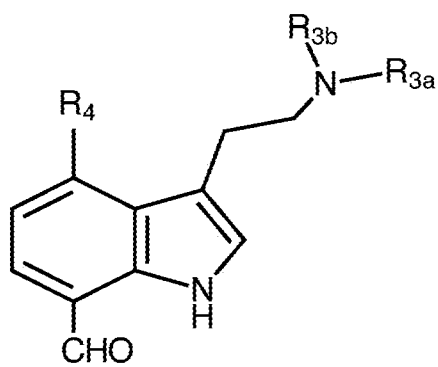
Figure 3E:
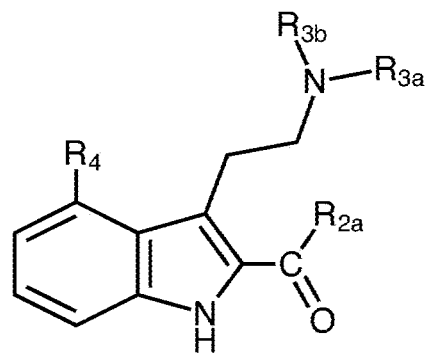
Figure 3F:
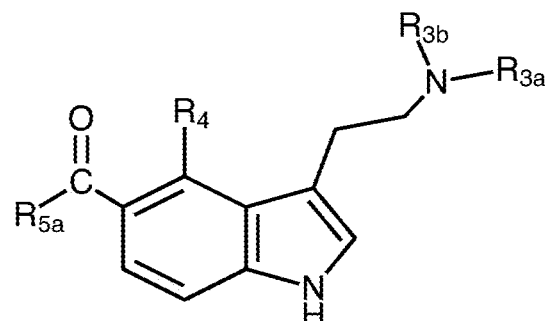
Figure 3G:
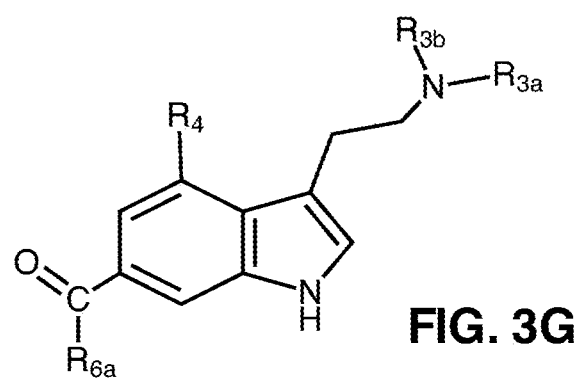
Figure 3H:
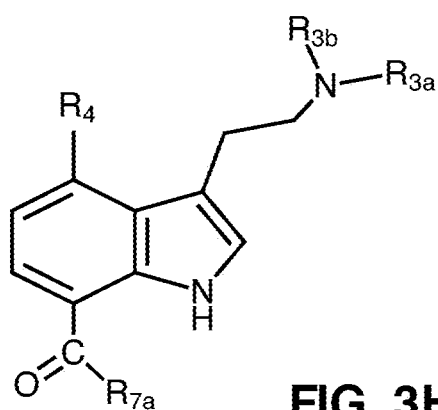

In a further aspect hereof, the $R_2$, $R_5$, $R_6$, or $R_7$ groups which are not an aldehyde or ketone can be a hydrogen atom. Referring now to FIGS. 3A-3D, examples of aldehyde psilocybin derivatives in accordance herewith, wherein one of $R_2$, $R_5$, $R_6$, or $R_7$ is an aldehyde, and the $R_2$, $R_5$, $R_6$, or $R_7$ which are not an aldehyde are hydrogen atoms are: the 2-formyl-psilocybin derivative compound depicted in FIG. 3A, the 5-formyl-psilocybin derivative depicted in FIG. 3B, the 6-formyl-psilocybin derivative depicted in FIG. 3C, and the 7-formyl-psilocybin derivative depicted in FIG. 3D, Referring now to FIGS. 3E-3H, examples of ketone psilocybin derivatives in accordance herewith, wherein one of $R_2$, $R_5$, $R_6$, or $R_7$ is a ketone, and the $R_2$, $R_5$, $R_6$, or $R_7$ which are not ketones are hydrogen atoms are: the 2-ketone-psilocybin derivative compound depicted in FIG. 3E, the 5-ketone-psilocybin derivative depicted in FIG. 3F, the 6-ketone-psilocybin derivative depicted in FIG. 3G, and the 7-ketone-psilocybin derivative depicted in FIG. 3H. It is noted that in FIGS. 3E-3H, Rea, $R_{6a}$, $R_{6a}$, and $R_{7a}$, can be an alkyl group or an aryl group.

Figure 5A:
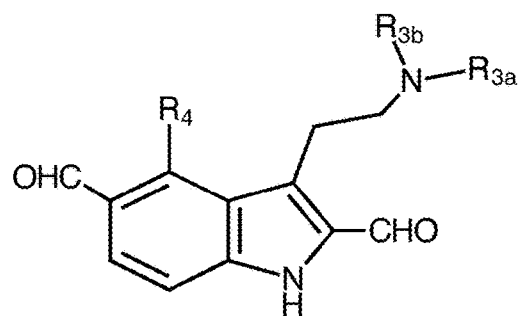
FIGS. 5A, 5B, 5C, 5D, 5E, 5F, 5G, 5H, 5I, 5J, 5K, 5L, 5M, 5N, 5O, 5P, 5Q, 5R, 5S, 5T, 5U, 5V, 5W, and 5X depict the chemical structures of certain example aldehyde and ketone psilocybin derivatives, notably a 2,5-di-formyl-psilocybin derivative (FIG. 5A), a 2,6-di-formyl-psilocybin derivative (FIG. 5B), a 2,7-di-formyl-psilocybin derivative (FIG. 5C), a 5,6-di-formyl-psilocybin derivative (FIG. 5D), a 5,7-di-formyl-psilocybin derivative (FIG. 5E), a 6,7-di-formyl-psilocybin derivative (FIG. 5F), a 2,5,6-tri-formyl-psilocybin derivative (FIG. 5G), a 2,5,7-tri-formyl-psilocybin derivative (FIG. 5H), a 2,6,7-tri-formyl-psilocybin derivative (FIG. 5I) a 5,6,7-tri-formyl-psilocybin derivative (FIG. 5J), a 2,5,6,7-tetra-formyl-psilocybin derivative (FIG. 5K), a 2,5-di-ketone-psilocybin derivative (or alternatively, the nomenclature is a 2,5-di-acyl-psilocybin derivative) (FIG. 5L), a 2,6-di-ketone-psilocybin derivative (FIG. 5M), a 2,7-di-ketone-psilocybin derivative (FIG. 5N), a 5,6-di-ketone psilocybin derivative (FIG. 5O), a 5,7-di-ketone-psilocybin derivative (FIG. 5P), a 6,7-di-ketone-psilocybin derivative (FIG. 5Q), a 2,5,6-tri-ketone-psilocybin derivative (FIG. 5R), a 2,5,7-tri-ketone-psilocybin derivative (FIG. 5S), a 2,6,7-tri-ketone-psilocybin derivative (FIG. 5T) a 5,6,7-tri-ketone-psilocybin derivative (FIG. 5U), a 2,5,6,7-tetra-ketone-psilocybin derivative (FIG. 5V), a 5-formyl-7-ketone-psilocybin derivative (FIG. 5W), and a 5-ketone, 7-formyl-psilocybin derivative (FIG. 5X).
Figure 5B:
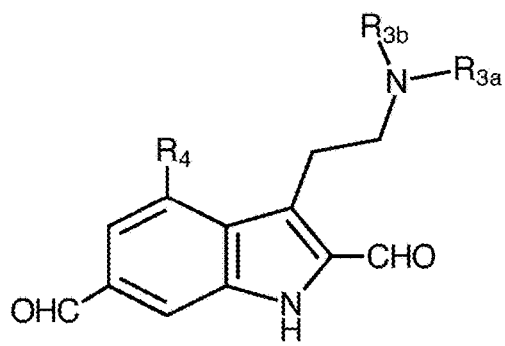
Figure 5C:
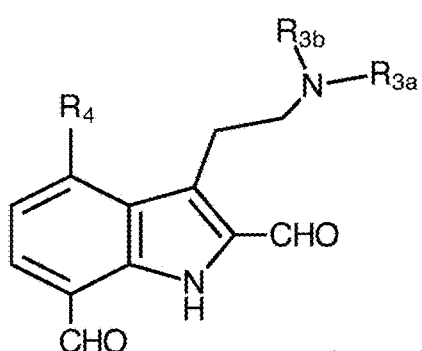
Figure 5D:
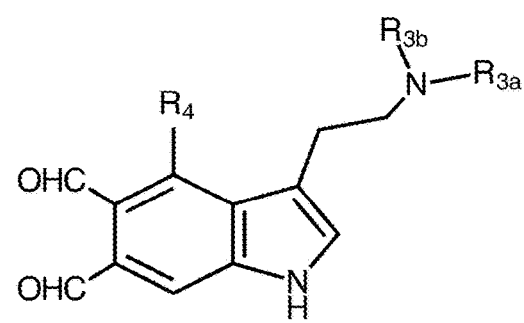
Figure 5E:
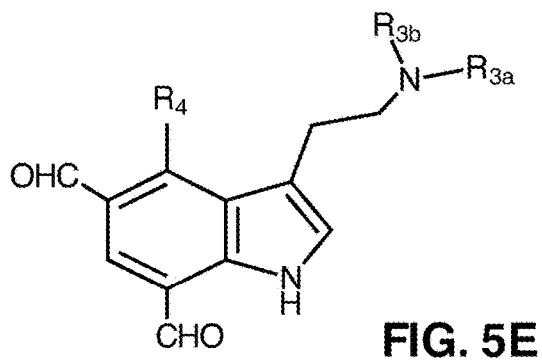
Figure 5F:
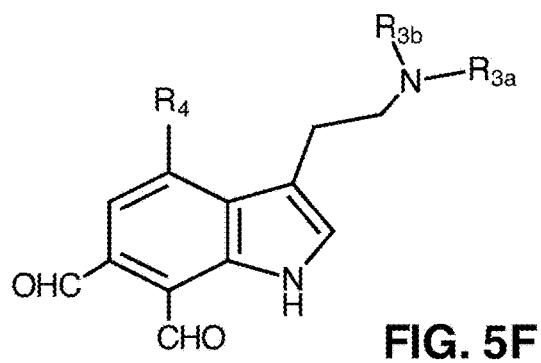

Referring now to FIGS. 5A-5F, examples of aldehyde psilocybin derivatives in accordance herewith, wherein two of $R_2$, $R_5$, $R_6$, or $R_7$ are aldehydes, and the $R_2$, $R_5$, $R_6$, or $R_7$ which are not aldehydes are hydrogen atoms, are: the 2,5-di-formyl-psilocybin derivative compound depicted in FIG. 5A, the 2,6-di-formyl-psilocybin derivative depicted in FIG. 5B, the 2,7-di-formyl-psilocybin derivative depicted in FIG. 5C, the 5,6-di-formyl-psilocybin derivative depicted in FIG. 5D, the 5,7-di-formyl-psilocybin derivative depicted in FIG. 5E, and the 6,7-di-formyl-psilocybin derivative depicted in FIG. 5F.

Figure 5G:
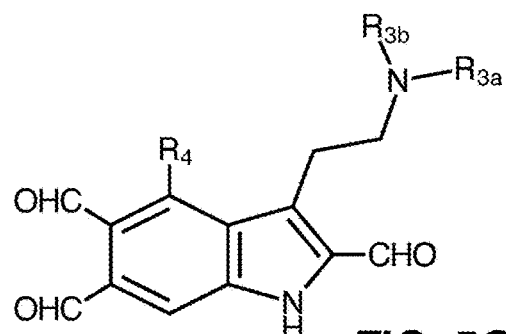
Figure 5H:
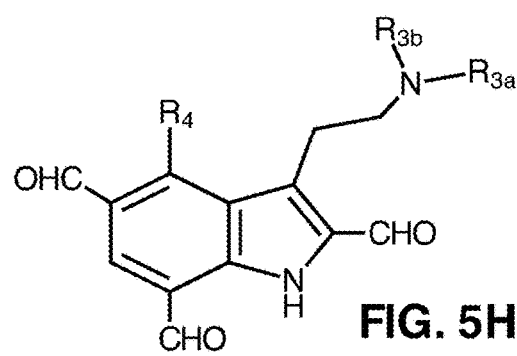
Figure 5I:
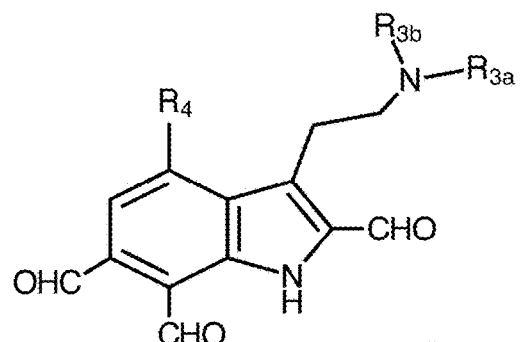
Figure 5J:
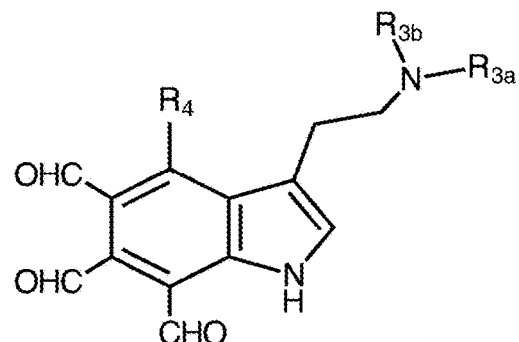

Referring now to FIGS. 5G-5J, examples of aldehyde psilocybin derivatives in accordance herewith, wherein three of $R_2$, $R_5$, $R_6$, or $R_7$ are aldehydes, and the $R_2$, $R_5$, $R_6$, or $R_7$ which are not aldehydes are hydrogen atoms are: the 2,5,6-tri-formyl-psilocybin derivative compound depicted in FIG. 5G, the 2,5,7-tri-formyl-psilocybin derivative depicted in FIG. 5H; the 2,6,7-tri-formyl-psilocybin derivative depicted in FIG. 5I and the 1-tri-formyl-psilocybin derivative depicted in FIG. 5J.

Figure 5K:
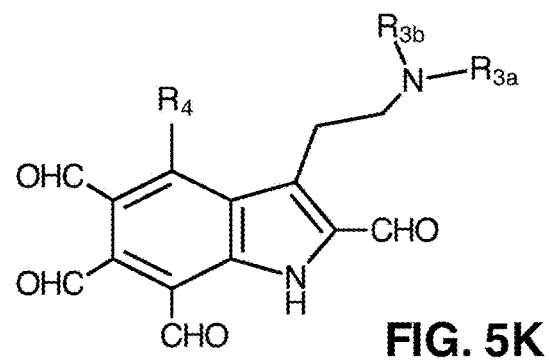

Referring now to FIG. 5K an example of an aldehyde psilocybin derivative in accordance herewith, wherein all four of $R_2$, $R_5$, $R_6$, or $R_7$ are an aldehyde is the 2,5,6,7-tetra-formyl-psilocybin derivative depicted in FIG. 4K.

Figure 5L:
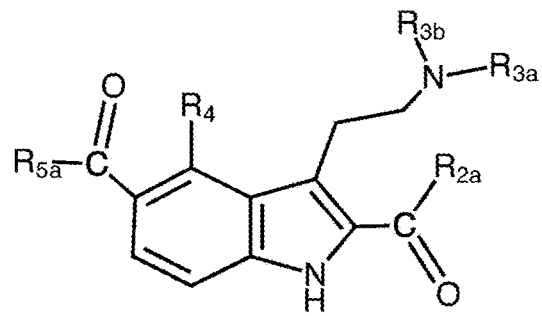
Figure 5M:
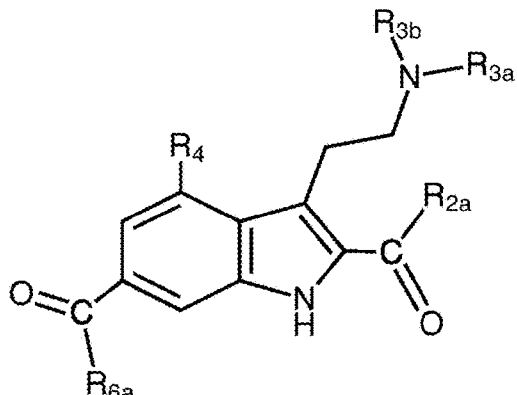
Figure 5N:
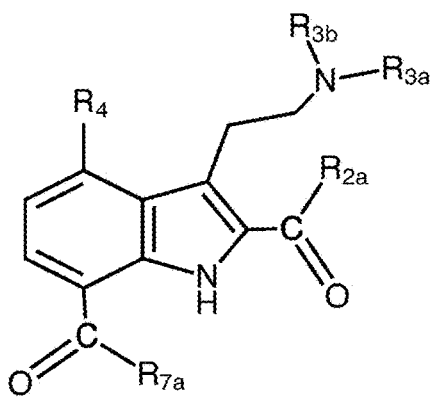
Figure 5O:
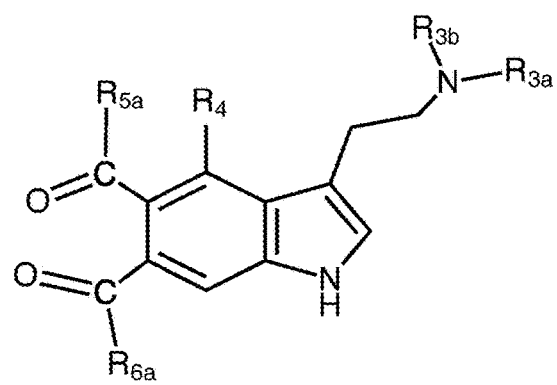
Figure 5P:
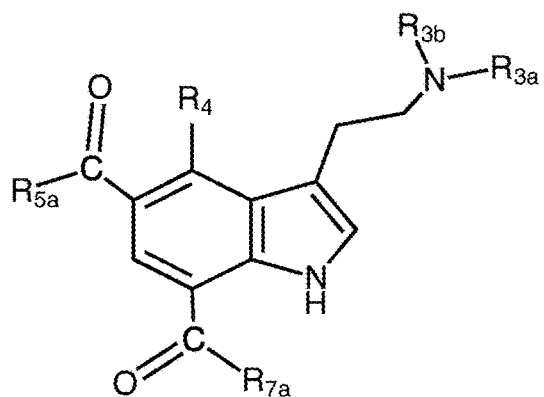
Figure 5Q:
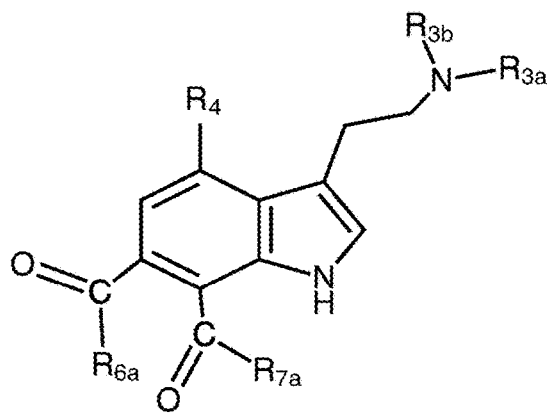

Referring now to FIGS. 5L-5Q, examples of ketone psilocybin derivatives in accordance herewith, wherein two of $R_2$, $R_5$, $R_6$, or $R_7$ are ketone groups, and wherein $R_2$, $R_5$, $R_6$, or $R_7$ which are not ketone groups are hydrogen atoms are: the 2,5-di-ketone-psilocybin derivative compound depicted in FIG. 5L, the 2,6-di-ketone-psilocybin derivative depicted in FIG. 5M, the 2,7-di-ketone-psilocybin derivative depicted in FIG. 5N, the 5,6-di-ketone-psilocybin derivative depicted in FIG. 5O, the 5,7-di-ketone-psilocybin derivative depicted in FIG. 5P, and the 6,7-di-ketone-psilocybin derivative depicted in FIG. 5Q. As hereinbefore noted, the R-groups i.e., $R_{2a}$, $R_{5a}$, $R_{6a}$ and $R_{7A}$, may be an alkyl group or an aryl group.

Figure 5R:
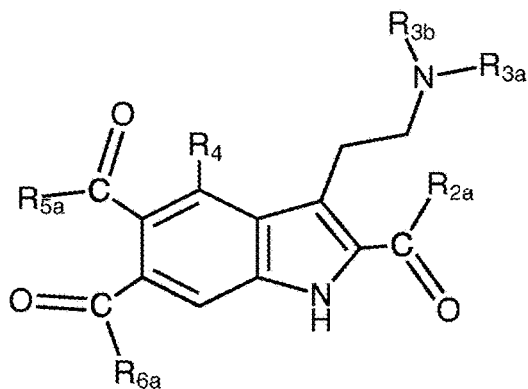
Figure 5S:
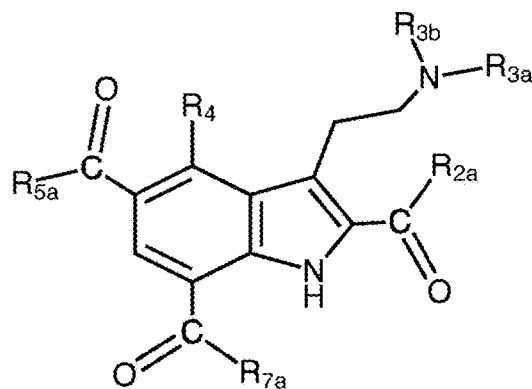
Figure 5T:
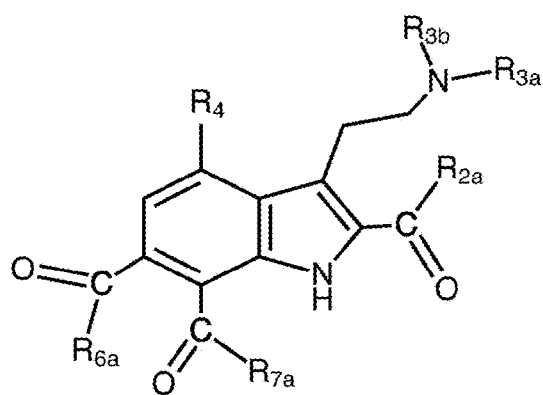
Figure 5U:
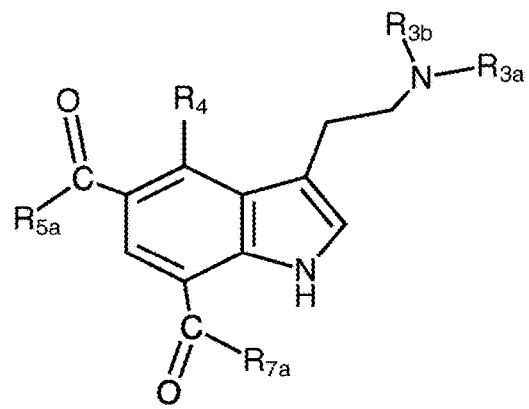
Figure 5V:
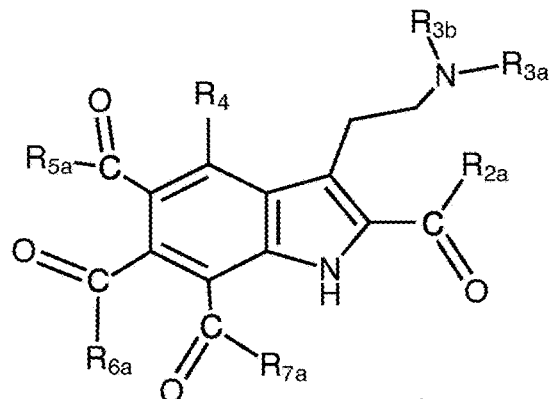
Figure 5W:
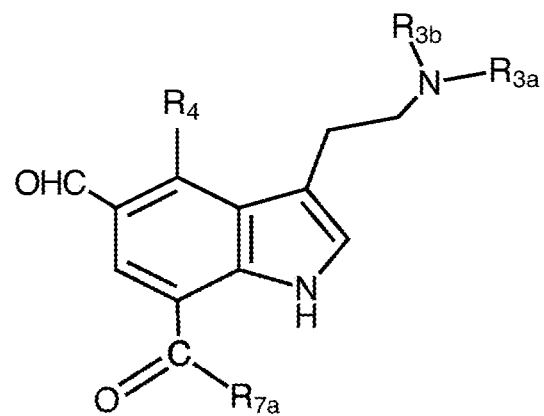
Figure 5X:
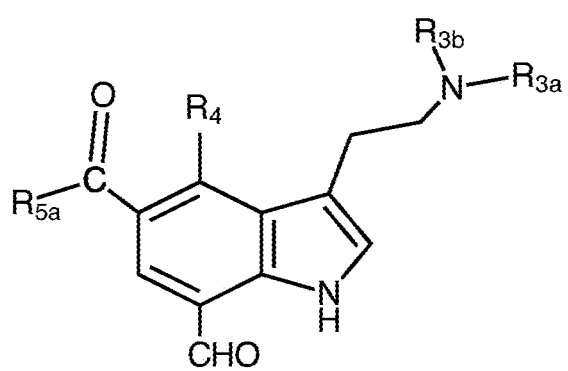

Referring now to FIGS. 5W-5X, it is noted that, in other embodiments, one of the substituent R groups may be an aldehyde group, while the other R group may be a ketone group. Thus, for example, referring to FIG. 5W, in such embodiments, the $C_7$ group may be a ketone group, while the $C_5$ group is an aldehyde (formyl) group, or conversely, as shown in in FIG. 5X, the $C_5$ group may be a ketone group, while the $C_7$ group may be an aldehyde (formyl) group. It is to be understood that any and all embodiments including a psilocybin derivatives wherein two of $R_2$, $R_5$, $R_6$ or $R_7$ are modified, include embodiments wherein none, one or two of these groups are aldehydes, or none, one or two of these groups are ketones, wherein at least two of $R_2$, $R_5$, $R_6$ or $R_7$ are an aldehyde or ketone, and wherein $R_2$, $R_5$, $R_6$ or $R_7$ which are not an aldehyde or ketone are a hydrogen atom.

Referring now to FIGS. 5R-5U, examples of ketone psilocybin derivatives in accordance herewith, wherein three of $R_2$, $R_5$, $R_6$, or $R_7$ are ketone groups, and wherein the $R_2$, $R_5$, $R_6$, or $R_7$ which are not ketone groups are hydrogen atoms are: the 2-,5-,6-ketone-psilocybin derivative compound depicted in FIG. 5R, the 2,5,7-ketone-tri-psilocybin derivative depicted in FIG. 5S, the 2,6,7-tri-ketone-psilocybin derivative depicted in FIG. 5T, and the 5,6,7-tri-ketone-psilocybin derivative depicted in FIG. 5U. As hereinbefore noted, the R-groups, i.e., $R_{2a}$, $R_{5a}$, $R_{6a}$ and $R_{7A}$, may be an alkyl group or an aryl group.

It is noted that, in other embodiments, one of the substituent R groups may be an aldehyde group, while the other R groups may be a ketone groups, or conversely, one of the R groups may be a ketone group, while the other R groups may be aldehyde groups. It is to be understood that any and all embodiments including psilocybin derivatives wherein three of $R_2$, $R_5$, $R_6$ or $R_7$ are modified, include embodiments wherein none, one, two, three of these groups are aldehydes, or none, one, two or three of these groups are ketones, wherein at least three of $R_2$, $R_5$, $R_6$ or $R_7$ are an aldehyde or ketone, and wherein $R_2$, $R_5$, $R_6$ or $R_7$ which is not an aldehyde or ketone is a hydrogen atom.

Referring now to FIG. 5V, an example of a ketone psilocybin derivative in accordance herewith, wherein all four of $R_2$, $R_5$, $R_6$, or $R_7$ are ketone groups is the 2,5,6,7-tetra-ketone-psilocybin derivative depicted in FIG. 5V. As hereinbefore noted, the R-groups, i.e., $R_{2a}$, $R_{5a}$, $R_{6a}$ and $R_{7A}$, may be an alkyl group or an aryl group.

It is noted that, in other embodiments, one of the substituent R groups may be an aldehyde group, while the other R groups may be a ketone groups or aldehyde groups, or conversely, one of the R groups may be a ketone group, while the other R groups may be aldehyde or ketone groups. It is to be understood that any and all embodiments including psilocybin derivatives wherein four of $R_2$, $R_5$, $R_6$ or $R_7$ are modified, include embodiments wherein none, one, two, three or four of these groups are aldehydes, or none, one, two or three, four of these groups are ketones, wherein all four of $R_2$, $R_5$, $R_6$ or $R_7$ are an aldehyde or ketone.

In a further aspect, $R_4$, can be an O-alkyl group. Referring now to FIGS. 6A, 6B, 7A, 7B, 8A, and 8B, examples of aldehyde psilocybin derivatives in accordance herewith, wherein $R_5$, and/or $R_7$ are aldehyde groups and $R_4$ is an O-alkyl group are: the 4-O-methyl-5-formyl-psilocybin derivative depicted in FIG. 6A, the 4-O-ethyl-5-formyl-psilocybin derivative depicted in FIG. 6B, the 4-O-methyl-7-formyl-psilocybin derivative depicted in FIG. 7A, the 4-O-ethyl-7-formyl-psilocybin derivative depicted in FIG. 7B, the 4-O-methyl-5,7-di-formyl-psilocybin derivative depicted in FIG. 8A, the 4-O-ethyl-5,7-di-formyl-psilocybin derivative depicted in FIG. 8B, It is noted that in these specific examples only 5-formyl, 7-formyl, and 5,7-di-formyl-4-O-alkyl psilocybin derivatives are shown. Further examples of O-alkyl psilocybin derivatives included herein are any and all O-alkyl psilocybin derivatives which may be selected by referring to the chemical formulas shown in FIGS. 3A-3D and FIGS. 5A-5K, wherein $R_4$ is an O-alkyl group. It will thus be clearly understood that FIGS. 6A, 6B, 7A, 7B, 8A, and 8B represent examples only of aldehyde and ketone psilocybin derivatives having chemical formula (I) wherein the $R_2$, $R_5$, $R_6$, or $R_7$ groups which are not an aldehyde group are a hydrogen atom. Other psilocybin derivatives wherein $R_2$, $R_5$, $R_6$, or $R_7$ which are not an aldehyde group, are a hydrogen atom can readily be selected, and thus are included in the O-alkylated aldehyde psilocybin derivatives compounds of the present disclosure.

It is noted that the example aldehyde psilocybin derivatives shown in FIGS. 6A, 6B, 7A, 7B, 8A, and 8B are aldehyde psilocybin derivatives compounds by virtue of their aldehyde groups. Considering, FIGS. 6A, 6B, 7A, 7B, 8A, and 8D in conjunction with FIGS. 3E-3H and FIGS. 5L-5X, it is noted, and it will be clear that, in other embodiments, included herein are, further, ketone psilocybin derivatives wherein instead of an aldehyde group the psilocybin derivative possesses at least one ketone group in accordance with chemical formula (II) or (III) wherein R is an alkyl group or aryl group.

In a further aspect, $R_4$, can be an O-acyl group. Referring now to FIGS. 6C, 6D, 7C, 7D, 8C, and 8D, examples of aldehyde psilocybin derivatives in accordance herewith, wherein $R_5$, and/or $R_7$ are aldehyde or ketone groups and $R_4$ is an O-acyl group are: the 4-acetyl-5-formyl-psilocybin derivative depicted in FIG. 6C, the 4-propionoyl-5-formyl-psilocybin derivative depicted in FIG. 6D, the 4-acetyl-7-formyl-psilocybin derivative depicted in FIG. 7C, the 4-propionoyl-7-formyl-psilocybin derivative depicted in FIG. 7D, the 4-acetyl-5,7-di-formyl-psilocybin derivative depicted in FIG. 8C, the 4-propionoyl-5,7-di-formyl-psilocybin derivative depicted in FIG. 8D. It is noted that in these specific examples only 5-formyl, 7-formyl, and 5,7-di-formyl O-acyl psilocybin derivatives are shown. Further examples of O-acyl psilocybin derivatives included herein are any and all O-acyl psilocybin derivatives which may be selected by referring to the chemical formulas shown in FIGS. 3A-3D and FIGS. 5A-5K, wherein $R_4$ is an O-acyl group. It will thus be clearly understood that FIGS. 6C, 6D, 7C, 7D, 8C, and 8D represent examples only of O-acylated psilocybin derivatives having chemical formula (I) wherein the $R_2$, $R_5$, $R_6$, or $R_7$ groups which are not an aldehyde are a hydrogen atom. Other aldehyde and ketone psilocybin derivatives wherein $R_2$, $R_5$, $R_6$, or $R_7$ which are not an aldehyde are a hydrogen atom can readily be selected, and thus are included in the O-acylated aldehyde psilocybin derivatives compounds of the present disclosure.

Figure 6I:
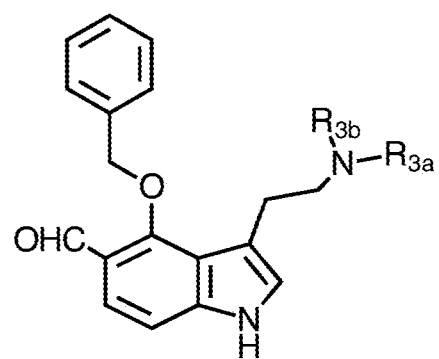

In a further aspect, $R_4$, can be an O-aryl group. Referring now to FIGS. 6I, 7I, and 8I examples of aldehyde psilocybin derivatives in accordance herewith, wherein $R_5$, and/or $R_7$ are aldehyde or ketone groups and $R_4$ is an O-aryl group are: the 4-benzyloxy-5-formyl-psilocybin derivative depicted in FIG. 6I, the 4-acetyl-7-benzyloxy-psilocybin derivative depicted in FIG. 7I, and the 4-phenylethylalcohol-5,7-di-formyl-psilocybin derivative depicted in FIG. 8I, It is noted that in these specific examples only 5-formyl, 7-formyl, and 5,7-di-formyl O-aryl psilocybin derivatives are shown. Further examples of O-aryl psilocybin derivatives included herein are any and all O-aryl psilocybin derivatives which may be selected by referring to the chemical formulas shown in FIGS. 3A-3D and FIGS. 5A-5K, wherein $R_4$ is an O-aryl group. It will thus be clearly understood that FIGS. 6I, 7I, and 8I represent examples only of O-arylated psilocybin derivatives having chemical formula (I) wherein the $R_2$, $R_5$, $R_6$, or $R_7$ groups which are not an aldehyde are a hydrogen atom. Other aldehyde and ketone psilocybin derivatives wherein $R_2$, $R_5$, $R_6$, or $R_7$ which are not an aldehyde are a hydrogen atom can readily be selected, and thus are included in the O-arylated aldehyde psilocybin derivatives compounds of the present disclosure.

It is noted that the example aldehyde psilocybin derivatives shown in FIGS. 6C, 6D, 7C, 7D, 8C, and 8D are aldehyde psilocybin derivatives compounds by virtue of their aldehyde groups. Considering, FIGS. 6C, 6D, 7C, 7D, 8C, and 8D in conjunction with FIGS. 3E-3H and FIGS. 5L-5X, it is noted, and it will be clear that, in other embodiments, included herein are, further, ketone psilocybin derivatives wherein instead of an aldehyde group the psilocybin derivative possesses at least one ketone group in accordance with chemical formula (II) or (III) wherein R is an alkyl group or aryl group.

In a further aspect, $R_4$, can be a hydroxy group. Referring now to FIGS. 6E, 7E, and 8E, examples of aldehyde psilocybin derivatives in accordance herewith, wherein $R_5$, and/or $R_7$ are aldehydes and are $R_4$ is a hydroxy group are: the 4-hydroxy-5-formyl-psilocybin derivative depicted in FIG. 6E, the 4-hydroxy-7-formyl-psilocybin derivative depicted in FIG. 7E, and the 4-hydroxy-5,7-di-formyl-psilocybin derivative depicted in FIG. 8E, It is noted that in these specific examples only 5-formyl, 7-formyl, and 5,7-di-formyl-psilocybin derivatives are shown. Further examples of hydroxy-psilocybin derivatives included herein are any and all hydroxy-psilocybin derivatives which may be selected by referring to the chemical formulas shown in FIGS. 3A-3D and FIGS. 5A-5K, wherein $R_4$ is a hydroxy group. It will thus be clearly understood that FIGS. 6E, 7E, and 8E represent examples only of hydroxy psilocybin derivatives having chemical formula (I) wherein the $R_2$, $R_5$, $R_6$, or $R_7$ groups which are not aldehyde groups are a hydrogen atom. Other psilocybin derivatives wherein $R_2$, $R_5$, $R_6$, or $R_7$ groups which are not aldehyde groups are a hydrogen atom can readily be selected, and thus are included in the aldehyde hydroxy psilocybin derivatives compounds of the present disclosure.

It is noted that the example aldehyde and ketone psilocybin derivatives shown in FIGS. 6E, 7E, and 8E are aldehyde psilocybin derivatives compounds by virtue of their aldehyde groups. Considering, FIGS. 6E, 7E and 8E in conjunction with FIGS. 3E-3H and FIGS. 5L-5X, it is noted, and it will be clear that, in other embodiments, included herein are, further, ketone psilocybin derivatives wherein instead of an aldehyde group the psilocybin derivative possesses at least one ketone group in accordance with chemical formula (II) or (III) wherein R is an alkyl group or aryl group.

Figure 6F:
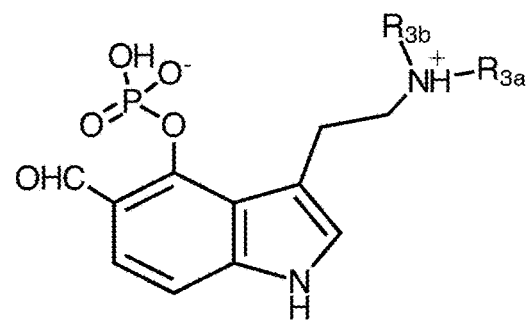

In a further aspect, $R_4$, can be a phosphate group. Referring now to FIGS. 6F, 7F, and 8F examples of aldehyde psilocybin derivatives in accordance herewith, wherein $R_5$, and/or $R_7$ are aldehyde groups and are $R_4$ is a phosphate group are: the 4-phosphate-5-formyl-psilocybin derivative depicted in FIG. 6F, the 4-phosphate-7-formyl-psilocybin derivative depicted in FIG. 7F, and the 4-phosphate-5,7-formyl-psilocybin derivative depicted in FIG. 8F, It is noted that in these specific examples only 5-formyl, 7-formyl, and 5,7-di-formyl-phosphate-psilocybin derivatives are shown. Further examples of phosphate-psilocybin derivatives included herein are any and all phosphate-psilocybin derivatives which may be selected by referring to the chemical formulas shown in FIGS. 3A-3D and FIGS. 5A-5K, wherein $R_4$ is a phosphate group. It will thus be clearly understood that FIGS. 6F, 7F, and 8F represent examples only of phosphate psilocybin derivatives having chemical formula (I) wherein $R_2$, $R_5$, $R_6$, or $R_7$ which are not aldehydes are a hydrogen atom. Other psilocybin derivatives wherein the $R_2$, $R_5$, $R_6$, or $R_7$ groups which are not aldehydes are a hydrogen atom can readily be selected, and thus are included in the aldehyde phosphate psilocybin derivatives compounds of the present disclosure.

It is noted that the example aldehyde and ketone psilocybin derivatives shown in FIGS. 6F, 7F, and 8F are aldehyde psilocybin derivatives compounds by virtue of their aldehyde groups. Considering, FIGS. 6F, 7F and 8F in conjunction with FIGS. 3E-3H and FIGS. 5L-5X, it is noted, and it will be clear that, in other embodiments, included herein are, further, ketone psilocybin derivatives wherein instead of an aldehyde group the psilocybin derivative possesses at least one ketone group in accordance with chemical formula (II) or (III) wherein R is an alkyl group or aryl group.

Figure 6G:
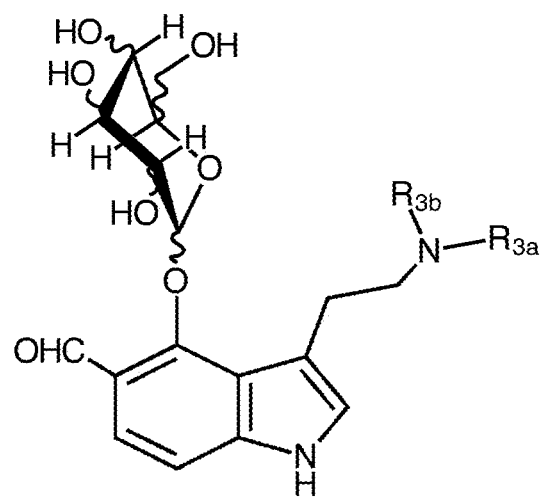

In a further aspect, $R_4$, can be a glycosyloxy group. Referring now to FIGS. 6G, 7G, and 8G, examples of aldehyde psilocybin derivatives in accordance herewith, wherein $R_5$, and/or $R_7$ are aldehyde groups and are $R_4$ is a glycosyloxy group are: the 4-O-glycosyl-5-formyl-psilocybin derivative depicted in FIG. 6G, the 4-O-glycosyl-7-formyl-psilocybin derivative depicted in FIG. 7G, and the 4-O-glycosyl-5,7-di-formyl-psilocybin derivative depicted in FIG. 8G, It is noted that in these specific examples only 5-formyl, 7-formyl, and 5,7-di-formyl-psilocybin derivatives are shown. Further examples of glycosyl-psilocybin derivatives included herein are any and all glycosyl-psilocybin derivatives which may be selected by referring to the chemical formulas shown in FIGS. 3A-3D and FIGS. 5A-5K, wherein $R_4$ is a glycosyloxy group. It will thus be clearly understood that FIGS. 6G, 7G, and 8G represent examples only of glycosyloxy psilocybin derivatives having chemical formula (I) wherein the $R_2$, $R_5$, $R_6$, or $R_7$ groups which are not aldehyde groups are a hydrogen atom. Other psilocybin derivatives wherein the $R_2$, $R_5$, $R_6$, or $R_7$ groups which are not aldehyde groups are a hydrogen atom can readily be selected, and thus are included in the aldehyde glycosyloxy psilocybin derivatives compounds of the present disclosure.

It is noted that the example aldehyde psilocybin derivatives shown in FIGS. 6G, 7G, and 8G are aldehyde psilocybin derivatives compounds by virtue of their aldehyde groups. Considering, FIGS. 6G, 7G and 8G in conjunction with FIGS. 3E-3H and FIGS. 5L-5X, it is noted, and it will be clear that, in other embodiments, included herein are, further, ketone psilocybin derivatives wherein instead of an aldehyde group the psilocybin derivative possesses at least one ketone group in accordance with chemical formula (II) or (III) wherein R is an alkyl group or aryl group.

Figure 6H:
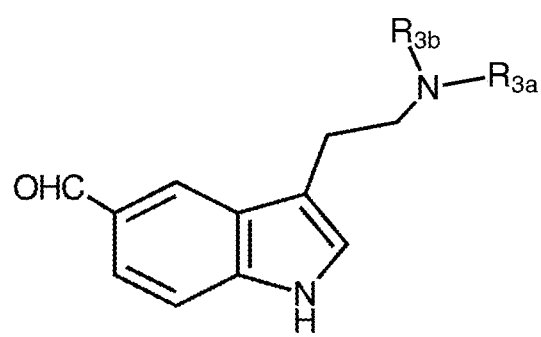

In a further aspect, $R_4$, can be a hydrogen atom. Referring now to FIGS. 6H, 7H, and 8H, examples of aldehyde psilocybin derivatives in accordance herewith, wherein $R_5$, and/or $R_7$ are aldehyde groups and are $R_4$ is a hydrogen atom are: the 4-hydro-5-formyl-psilocybin derivative depicted in FIG. 6H, the 4-hydro-7-formyl-psilocybin derivative depicted in FIG. 7H, and the 4-hydro-5,7-di-formyl-psilocybin derivative depicted in FIG. 8H, It is noted that in these specific examples only 5-formyl, 7-formyl, and 5,7-di-formyl-hydro-psilocybin derivatives are shown. Further examples of hydro-psilocybin derivatives included herein are any and all hydro-psilocybin derivatives which may be selected by referring to the chemical formulas shown in FIGS. 3A-3D and FIGS. 5A-5K, wherein $R_4$ is a hydrogen atom. It will thus be clearly understood that FIGS. 6H, 7H, and 8H represent examples only of hydro psilocybin derivatives having chemical formula (I) wherein $R_2$, $R_5$, $R_6$, or $R_7$ groups are a hydrogen atom. Other aldehyde psilocybin derivatives wherein $R_2$, $R_5$, $R_6$, or $R_7$ groups which are not an aldehyde are a hydrogen atom can readily be selected, and thus are included in the aldehyde hydro psilocybin derivatives compounds of the present disclosure.

It is noted that the example aldehyde psilocybin derivatives shown in FIGS. 6H, 7H, and 8H are aldehyde psilocybin derivatives compounds by virtue of their aldehyde groups. Considering, FIGS. 6H, 7H and 8H in conjunction with FIGS. 3E-3H and FIGS. 5L-5X, it is noted, and it will be clear that, in other embodiments, included herein are, further, ketone psilocybin derivatives wherein instead of an aldehyde group the psilocybin derivative possesses at least one ketone group in accordance with chemical formula (II) or (III) wherein R is an alkyl group or aryl group.

Furthermore, in example one embodiment, the psilocybin derivative according to the present disclosure can be a chemical compound having the formula (VIII):

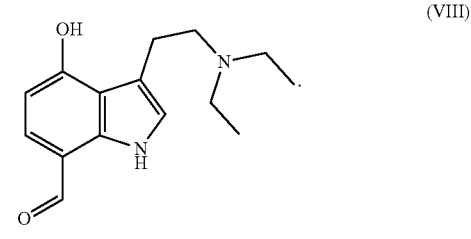 [SMILES: CCN(CC)CCc1c[nH]c2c(C=O)ccc(O)c12]

(VIII)

Furthermore, in example one embodiment, the psilocybin derivative according to the present disclosure can be a chemical compound having the formula (IX):

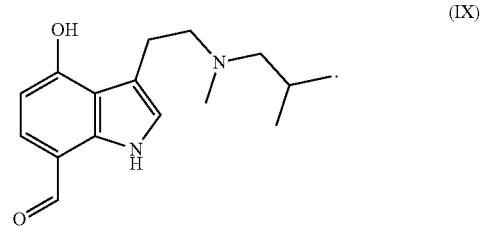 [SMILES: CC(C)CN(C)CCc1c[nH]c2c(C=O)ccc(O)c12]

(IX)

Furthermore, in one example embodiment, the psilocybin derivative according to the present disclosure can be a chemical compound having the formula (X):

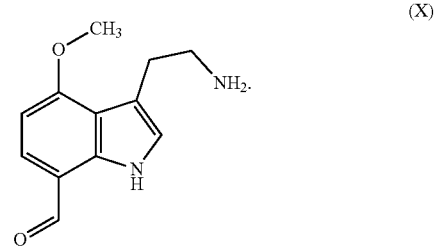 [SMILES: COc1ccc(C=O)c2[nH]cc(CCN)c12]

(X)

Furthermore, in one example embodiment, the psilocybin derivative according to the present disclosure can be a chemical compound having the formula (XI):

(XI)

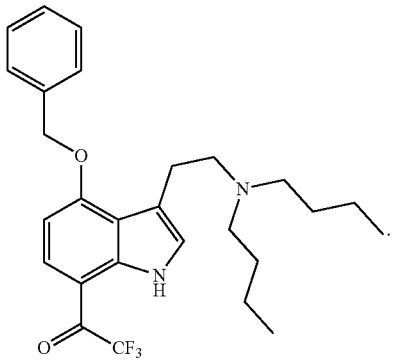

Furthermore, in one example embodiment, the psilocybin derivative according to the present disclosure can be a chemical compound having the formula (XII):

(XII)

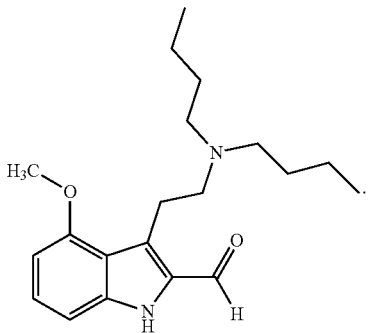

Furthermore, in one example embodiment, the psilocybin derivative according to the present disclosure can be a chemical compound having the formula (XIII):

(XIII)

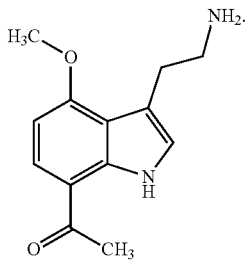

Furthermore, in one example embodiment, the psilocybin derivative according to the present disclosure can be a chemical compound having the formula (XIV):

(XIV)

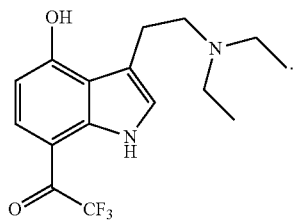

Furthermore, in one example embodiment, the psilocybin derivative according to the present disclosure can be a chemical compound having the formula (XV):

(XV)

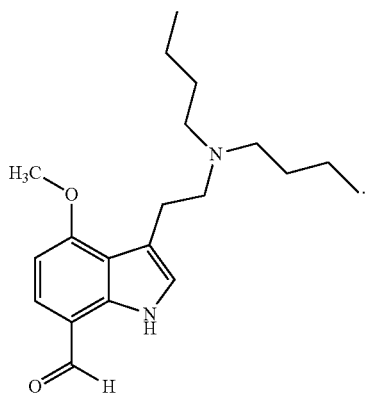

Furthermore, it is noted that the aldehyde and ketone psilocybin derivatives of the present disclosure include salts thereof, including pharmaceutically acceptable salts. Thus, the nitrogen atom of the ethyl-amino group extending in turn from the C3 atom may be protonated, and the positive charge may be balanced by, for example, chloride or sulfate ions, to thereby form a chloride salt or a sulfate salt. Furthermore, in compounds wherein $R_a$ is a phosphate group, the phosphate group may be de-protonated, and the negative charge may be balanced by, for example, sodium ions or potassium ions, to thereby form a sodium salt or a potassium salt.

Furthermore, it is noted that when $R_a$ is a phosphate group, the term aldehyde and ketone psilocybin derivative also includes compounds having the formula (VII):

(VII)

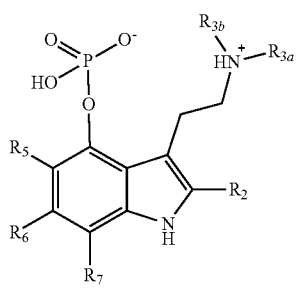

wherein at least one of $R_2$, $R_5$, $R_6$, or $R_7$ is an aldehyde or ketone group, and wherein each $R_2$, $R_5$, $R_6$, or $R_7$ which is not an aldehyde or ketone group is a hydrogen atom, wherein $R_4$ is an O-alkyl group, an O-acyl group, an O-alkaryl group, a hydroxy group, a phosphate group, a glycosyloxy group, or a hydrogen atom and wherein $R_{3A}$ and $R_{3B}$ each interpedently are a hydrogen atom, an alkyl group, acyl group or an aryl group. Further included are salts of aldehyde or ketone psilocybin derivatives having the formula (VII), such as a sodium salt, a potassium salt etc.

Thus, to briefly recap, the present disclosure provides aldehyde and ketone psilocybin derivatives. The disclosure provides, in particular, a chemical compound having the chemical formula (I):

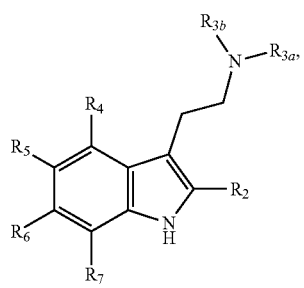

(I)

wherein, at least one of $R_2$, $R_5$, $R_6$, or $R_7$ is an aldehyde or a ketone group, and wherein each of $R_2$, $R_5$, $R_6$, or $R_7$ which is not a aldehyde group or a ketone group, is a hydrogen atom, an alkyl group, or O-alkyl group, wherein $R_4$ is an O-alkyl group, an O-acyl group, an O-alkaryl group, an O-aryl group, a hydroxy group, a phosphate group, a glycosyloxy group, or a hydrogen atom and wherein $R_{3A}$ and $R_{3B}$ each independently are a hydrogen atom, an alkyl group, acyl group or an aryl group. Ketone groups include, in selected example embodiments, ketones having the noted chemical formula (II) or (III). Aldehyde groups include, in selected example embodiments, the aldehydes having the noted chemical formulas (IV) or (V).

In one embodiment, at least one of $R_2$, $R_4$, $R_5$, $R_6$, or $R_7$ is an aldehyde or ketone group, and wherein each $R_2$, $R_5$, $R_6$, or $R_7$ which is not an aldehyde or ketone group is a hydrogen atom or a $(C_1\text{-}C_{20})$-alkyl group or $(C_1\text{-}C_{20})$—O-alkyl group. In another embodiment, each $R_2$, $R_5$, $R_6$, or $R_7$ which is not an aldehyde or ketone is a hydrogen atom, a methyl group, ethyl group, a propyl group, an O-methyl group, an O-ethyl group, or an O-propyl group.

In another embodiment, each $R_2$, $R_5$, $R_6$, or $R_7$ which is not an aldehyde or ketone group is a hydrogen atom or a $(C_1\text{-}C_{10})$-alkyl group or $(C_1\text{-}C_{10})$—O-alkyl group. In another embodiment, each $R_2$, $R_5$, $R_6$, or $R_7$ is not an aldehyde or ketone is a hydrogen atom, a methyl group, ethyl group, a propyl group, an O-methyl group, an O-ethyl group, or an O-propyl group.

In another embodiment, when $R_4$ is not an aldehyde or ketone group, $R_4$ is a hydrogen atom, a $(C_1\text{-}C_{20})$-alkyl group or $(C_1\text{-}C_{20})$—O-alkyl group, a hydroxy group, a glycosyloxy group, or a phosphate group. In another embodiment, when $R_4$ is not an aldehyde or ketone group, $R_4$ is a hydrogen atom, a $(C_1\text{-}C_{10})$-alkyl group or $(C_1\text{-}C_{10})$—O-alkyl group, a hydroxy group, a glycosyloxy group, or a phosphate group. In another embodiment, when $R_4$ is not an aldehyde or ketone group, $R_4$ is a hydrogen atom, a $(C_1\text{-}C_6)$-alkyl group or $(C_1\text{-}C_6)$—O-alkyl group, a hydroxy group, a glycosyloxy group, or a phosphate group. In another embodiment, when $R_4$ is not an aldehyde or ketone group, $R_4$ is a hydrogen atom, a methyl group, an ethyl group, a propyl group, a glycosyloxy group, a phosphate group, an O-methyl group, an O-ethyl group, or an O-propyl group.

In another embodiment, $R_{3A}$ and $R_{3B}$ are a hydrogen atom, a $(C_1\text{-}C_{20}$-alkyl group, a $(C_6\text{-}C_{14})$-aryl group, or a —C(=O)$(C_1\text{-}C_{20})$-alkyl group. In another embodiment, $R_{3A}$ and $R_{3B}$ are a hydrogen atom, a $(C_1\text{-}C_{10})$-alkyl group, a $(C_6\text{-}C_{10})$-aryl group, or a —C(=O)$(C_1\text{-}C_{10})$-alkyl group. In another embodiment, $R_{3A}$ and $R_{3B}$ are a hydrogen atom, a $(C_1\text{-}C_6)$-alkyl group, a phenyl group, or a —C(=O)$(C_1\text{-}C_6)$-alkyl group. In another embodiment, $R_{3A}$ and $R_{3B}$ are a hydrogen atom, a methyl group, an ethyl group, a propyl group, a phenyl group, —C(=O)—$CH_3$, —O(=O)—$CH_2CH_3$, or —C(=O)—$CH_2CH_2CH_3$.

In one embodiment of the disclosure, a chemical compound or salt thereof having formula (I) is included:

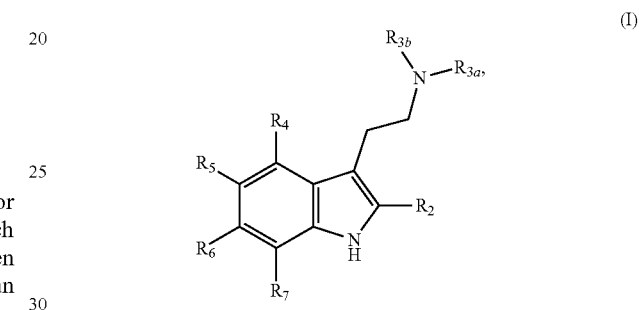

(I)

wherein, at least one of $R_2$, $R_5$, $R_6$, or $R_7$ is an aldehyde or a ketone group, and wherein each of $R_2$, $R_5$, $R_6$, or $R_7$ which is not a aldehyde group or a ketone group, is a hydrogen atom, an alkyl group, or O-alkyl group, wherein $R_4$ is an O-alkyl group, an O-acyl group, an O-alkaryl group, an O-aryl group, a hydroxy group, a phosphate group, a glycosyloxy group, or a hydrogen atom and wherein $R_{3A}$ and $R_{3B}$ each independently are a hydrogen atom, an alkyl group, acyl group or an aryl group.

In one embodiment, $R_2$, $R_5$, $R_6$, and $R_7$ are independently or simultaneously H, $(C_1\text{-}C_{20})$-alkyl group or $(C_1\text{-}C_{20})$—O-alkyl group or an aldehyde or ketone group. In one embodiment, $R_2$, $R_5$, $R_6$, and $R_7$ are independently or simultaneously H, $(C_1\text{-}C_{10})$-alkyl group or $(C_1\text{-}C_{10})$—O-alkyl group or an aldehyde or ketone group. In one embodiment, $R_2$, $R_5$, $R_6$, and $R_7$ are independently or simultaneously H, $(C_1\text{-}C_6)$-alkyl group or $(C_1\text{-}C_6)$—O-alkyl group or an aldehyde or ketone group. In one embodiment, $R_2$, $R_5$, $R_6$, and $R_7$ are independently or simultaneously H, methyl, ethyl, propyl, O-methyl, O-ethyl, O-propyl, or an aldehyde or ketone group.

In one embodiment, $R_4$ is H, $(C_1\text{-}C_{20})$-alkyl group or $(C_1\text{-}C_{20})$—O-alkyl group, or an aldehyde or ketone group, a glycosyloxy group, or a phosphate group. In one embodiment, $R_4$ is H, $(C_1\text{-}C_{10})$-alkyl group or $(C_1\text{-}C_{10})$—O-alkyl group, an aldehyde or ketone group, a glycosyloxy group, or a phosphate group. In one embodiment, $R_4$ is H, $(C_1\text{-}C_6)$-alkyl group or $(C_1\text{-}C_6)$—O-alkyl group, a glycosyloxy group, a hydroxy group, or a phosphate group. In one embodiment, $R_4$ is H, methyl, ethyl, propyl, O-methyl, O-ethyl, O-propyl, $(C_6\text{-}C_{14})$—O-aryl group, or an aldehyde or ketone group, a glycosyloxy group, a hydroxy group, or a phosphate group.

In another embodiment, $R_{3A}$ and $R_{3B}$ are a hydrogen atom, a $(C_1\text{-}C_{20}$-alkyl group, a $(C_6\text{-}C_{14})$-aryl group, or a —C(=O)$(C_1\text{-}C_{20})$-alkyl group. In another embodiment, $R_{3A}$ and $R_{3B}$ are a hydrogen atom, a (C1-$C_{10}$)-alkyl group, a ($C_6$-$C_{10}$)-aryl group, or a —O(=O)($C_1$-$C_{10}$)-alkyl group or O-alkyl group. In another embodiment, $R_{3A}$ and $R_{3B}$ are a hydrogen atom, a ($C_1$-$C_6$)-alkyl group, a phenyl group, or a —C(=O) ($C_1$-$C_6$)-alkyl group. In another embodiment, $R_{3A}$ and $R_{3B}$ are a hydrogen atom, a methyl group, an ethyl group, a propyl group, a phenyl group, —C(=O)—$OH_3$, —C(=O)—$CH_2CH_3$, or —C(=O)—$CH_2CH_2CH_3$.

The aldehyde and ketone psilocybin derivatives of the present disclosure may be used to prepare a pharmaceutical or recreational drug formulation. Thus in one embodiment, the present disclosure further provides in another aspect, pharmaceutical and recreational drug formulations comprising aldehyde and ketone psilocybin derivatives. Accordingly, in one aspect, the present disclosure provides in a further embodiment a pharmaceutical or recreational drug formulation comprising a chemical compound having the chemical formula (I):

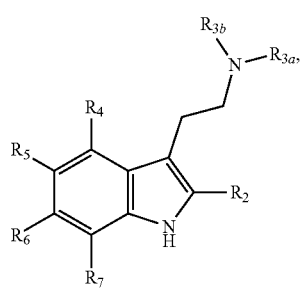

wherein, at least one of $R_2$, $R_5$, $R_6$, or $R_7$ is an aldehyde or a ketone group, and wherein each of $R_2$, $R_5$, $R_6$, or $R_7$ which is not a aldehyde group or a ketone group, is a hydrogen atom, an alkyl group, or O-alkyl group, wherein $R_4$ is an O-alkyl group, an O-acyl group, an O-aryl group, an O-alkaryl group, a hydroxy group, a phosphate group, a glycosyloxy group, or a hydrogen atom and wherein $R_{3A}$ and $R_{3B}$ each independently are a hydrogen atom, an alkyl group, acyl group or an aryl group, together with a diluent, carrier or excipient.

The dose when using the compounds of the present disclosure can vary within wide limits, and as is customary and is known to those of skill in the art, the dose can be tailored to the individual conditions in each individual case. The dose depends, for example, on the nature and severity of the illness to be treated, on the condition of the patient, on the compound employed or on whether an acute or chronic disease state is treated, or prophylaxis is conducted, on the mode of delivery of the compound, or on whether further active compounds are administered in addition to the compounds of the present disclosure. Representative doses of the present invention include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to about 100 mg, about 0.001 mg to about 50 mg, and about 0.001 mg to about 25 mg. Representative doses of the present disclosure include, but are not limited to, about 0.0001 to about 1,000 mg, about 10 to about 160 mg, about 10 mg, about 20 mg, about 40 mg, about 80 mg or about 160 mg. Multiple doses may be administered during the day, especially when relatively large amounts are deemed to be needed, for example 2, 3 or 4, doses. Depending on the subject and as deemed appropriate from the patient's physician or care giver it may be necessary to deviate upward or downward from the doses described herein.

The pharmaceutical or recreational drug formulations may be prepared as liquids, tablets, capsules, microcapsules, nanocapsules, trans-dermal patches, gels, foams, oils, aerosols, nanoparticulates, powders, creams, emulsions, micellar systems, films, sprays, ovules, infusions, teas, decoctions, suppositories, etc. and include a pharmaceutically acceptable salt or solvate of the aldehyde and ketone psilocybin compound together with an excipient. The term "excipient" as used herein means any ingredient other than the chemical compound of the disclosure. As will readily be appreciated by those of skill in art, the selection of excipient may depend on factors such as the particular mode of administration, the effect of the excipient on solubility of the chemical compounds of the present disclosure and methods for their preparation will be readily apparent to those skilled in the art. Such compositions and methods for their preparation may be found, for example, in "Remington's Pharmaceutical Sciences", 22nd Edition (Pharmaceutical Press and Philadelphia College of Pharmacy at the University of the Sciences, 2012).

The pharmaceutical and drug formulations comprising the aldehyde and ketone psilocybin derivatives of the present disclosure may be administered orally. Oral administration may involve swallowing, so that the compound enters the gastrointestinal tract, or buccal or sublingual administration may be employed by which the compound enters the blood stream directly from the mouth. Formulations suitable for oral administration include both solid and liquid formulations.

Solid formulations include tablets, capsules (containing particulates, liquids, microcapsules, or powders), lozenges (including liquid-filled lozenges), chews, multi- and nano-particulates, gels, solid solutions, liposomal preparations, microencapsulated preparations, creams, films, ovules, suppositories, and sprays.

Liquid formulations include suspensions, solutions, syrups, and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch, and dibasic calcium phosphate dihydrate.

Tablets may also optionally comprise surface active agents, such as sodium lauryl sulfate and polysorbate 80. When present, surface active agents may comprise from 0.2% (w/w) to 5% (w/w) of the tablet.

Tablets may further contain lubricants such as magnesium stearate, calcium stearate, zinc stearate, sodium stearyl fumarate, and mixtures of magnesium stearate with sodium lauryl sulphate. Lubricants generally comprise from 0.25% (w/w) to 10% (w/w), from 0.5% (w/w) to 3% (w/w) of the tablet.

In addition to the aldehyde and ketone psilocybin derivative, tablets may contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1% (w/w) to 25% (w/w) or from 5% (w/w) to 20% (w/w) of the dosage form.

Other possible auxiliary ingredients include anti-oxidants, colourants, flavouring agents, preservatives, and taste-masking agents.

For tablet dosage forms, depending on the desired effective amount of the chemical compound, the chemical compound of the present disclosure may make up from 1% (w/w) to 80% (w/w) of the dosage form, more typically from 5% (w/w) to 60% (w/w) of the dosage form.

Exemplary tablets contain up to about 80% (w/w) of the chemical compound, from about 10% (w/w) to about 90% (w/w) binder, from about 0% (w/w) to about 85% (w/w) diluent, from about 2% (w/w) to about 10% (w/w) disintegrant, and from about 0.25% (w/w) to about 10% (w/w) lubricant.

The formulation of tablets is discussed in "Pharmaceutical Dosage Forms: Tablets", Vol. 1- Vol. 3, by CRC Press (2008).

The pharmaceutical and recreational drug formulations comprising the aldehyde and ketone psilocybin derivatives of the present disclosure may also be administered directly into the blood stream, into muscle, or into an internal organ. Thus, the pharmaceutical and recreational drug formulations can be administered parenterally (for example, by subcutaneous, intravenous, intraarterial, intrathecal, intraventricular, intracranial, intramuscular, or intraperitoneal injection). Parenteral formulations are typically aqueous solutions which may contain excipients such as salts, carbohydrates and buffering agents (in one embodiment, to a pH of from 3 to 9), but, for some applications, they may be more suitably formulated as a sterile non-aqueous solution or as a dried form to be used in conjunction with a suitable vehicle such as sterile water.

Formulations comprising the aldehyde and ketone psilocybin derivatives of the present disclosure for parenteral administration may be formulated to be immediate and/or modified release. Modified release formulations include delayed-, sustained-, pulsed-, controlled-, targeted and programmed release. Thus the chemical compounds of the disclosure may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The pharmaceutical or recreational drug formulations of the present disclosure also may be administered topically to the skin or mucosa, i.e., dermally or transdermally. Example pharmaceutical and recreational drug formulations for this purpose include gels, hydrogels, lotions, solutions, creams, ointments, dusting powders, cosmetics, oils, eye drops, dressings, foams, films, skin patches, wafers, implants, sponges, fibres, bandages and microemulsions. Liposomes may also be used. Example carriers include alcohol, water, mineral oil, liquid petrolatum, white petrolatum, glycerin, polyethylene glycol and propylene glycol. Penetration enhancers may be incorporate (see: for example, Finnin, B. and Morgan, T. M., 1999 J. Pharm. Sci, 88 (10), 955-958).

Other means of topical administration include delivery by electroporation, iontophoresis, phonophoresis, sonophoresis and microneedle or needle-free (e.g., Powderject™, Bioject™, etc.) injection.

Pharmaceutical and recreational drug formulations for inhalation or insufflation include solutions and suspensions in pharmaceutically acceptable, aqueous, or organic solvents, or mixtures thereof, and powders. The liquid or solid pharmaceutical compositions can contain suitable pharmaceutically acceptable excipients. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally, or nasally, from devices that deliver the formulation in an appropriate manner.

In further embodiments, in which the aldehyde psilocybin derivative compounds of present disclosure are used as a recreational drug, the compounds may be included in compositions such as a food or food product, a beverage, a food seasoning, a personal care product, such as a cosmetic, perfume or bath oil, or oils (both for topical administration as massage oil, or to be burned or aerosolized). The chemical compounds of the present disclosure may also be included in a "vape" product, which may also include other drugs, such as nicotine, and flavorings.

In light of the foregoing, in another aspect the present disclosure provides, in at least one embodiment, a use of a chemical compound having the chemical formula (I):

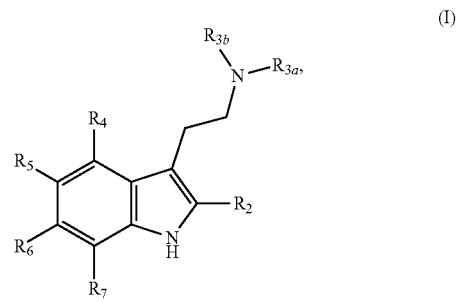

(I)

wherein, at least one of $R_2$, $R_5$, $R_6$, or $R_7$ is an aldehyde group or a ketone group, and wherein each $R_2$, $R_5$, $R_6$, or $R_7$ which is not an aldehyde group or a ketone group, is a hydrogen atom, an alkyl group, or O-alkyl group, wherein $R_4$ is an O-alkyl group, an O-acyl group, an O-aryl group, an O-alkaryl group, a hydroxy group, a phosphate group, a glycosyloxy group, or a hydrogen atom and wherein $R_{3A}$ and $R_{3B}$ each independently are a hydrogen atom, an alkyl group, acyl group or an aryl group, in the manufacture of a pharmaceutical or recreational drug formulation.

In at least one embodiment, the manufacture can comprise formulating the chemical compound with an excipient, diluent, or carrier.

Furthermore, in another aspect the present disclosure provides, in at least one embodiment, a use of a chemical compound having the chemical formula (I):

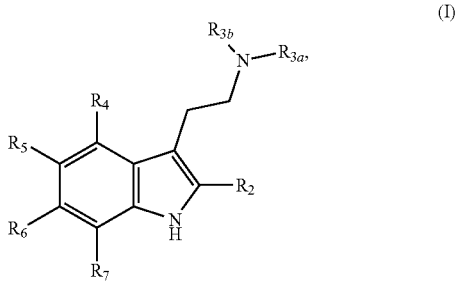

(I)

wherein, at least one of $R_2$, $R_5$, $R_6$, or $R_7$ is an aldehyde group or a ketone group, and wherein each $R_2$, $R_5$, $R_6$, or $R_7$ which is not an aldehyde group or a ketone group is a hydrogen atom, an alkyl group, or O-alkyl group, wherein $R_4$ is an O-alkyl group, an O-acyl group, an O-aryl group, an O-alkaryl group, a hydroxy group, a phosphate group, a glycosyloxy group, or a hydrogen atom and wherein $R_{3A}$ and $R_{3B}$ each independently are a hydrogen atom, an alkyl group, acyl group or an aryl group, together with a diluent, carrier, or excipient as a pharmaceutical or recreational drug formulation.

The pharmaceutical formulations comprising the chemical compounds of the present disclosure may be used to treat a subject, and in particular to treat a psychiatric disorder in a subject. Accordingly, the present disclosure includes in a further embodiment, a method for treating a psychiatric disorder, the method comprising administering to a subject in need thereof a pharmaceutical formulation comprising a chemical compound having the chemical formula (I):

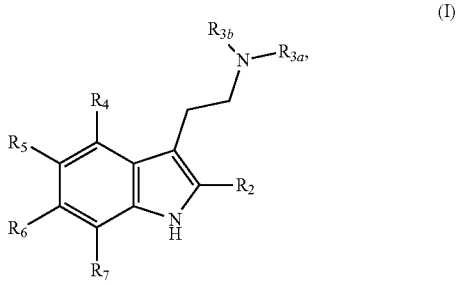

(I)

wherein, at least one of $R_2$, $R_5$, $R_6$, or $R_7$ is an aldehyde or a ketone group, and wherein each of $R_2$, $R_5$, $R_6$, or $R_7$ which is not a aldehyde group or a ketone group, is a hydrogen atom, an alkyl group, or O-alkyl group, wherein $R_4$ is an O-alkyl group, an O-acyl group, an O-aryl group, an O-alkaryl group, a hydroxy group, a phosphate group, a glycosyloxy group, or a hydrogen atom and wherein $R_{3A}$ and $R_{3B}$ each independently are a hydrogen atom, an alkyl group, acyl group or an aryl group, together with a diluent, carrier, or excipient.

Psychiatric disorders that may be treated include, for example, neurodevelopmental disorders such as intellectual disability, global development delay, communication disorders, autism spectrum disorder, and attention-deficit hyperactivity disorder (ADHD); bipolar and related disorders, such as mania, and depressive episodes; anxiety disorder, such as generalized anxiety disorder (GAD), agoraphobia, social anxiety disorder, specific phobias (natural events, medical, animal, situational, for example), panic disorder, and separation anxiety disorder; stress disorders, such as acute stress disorder, adjustment disorders, post-traumatic stress disorder (PTSD), and reactive attachment disorder; dissociative disorders, such as dissociative amnesia, dissociative identity disorder, and depersonalization/derealization disorder; somatoform disorders, such as somatic symptom disorders, illness anxiety disorder, conversion disorder, and factitious disorder; eating disorders, such as anorexia nervosa, bulimia nervosa, rumination disorder, pica, and binge-eating disorder; sleep disorders, such as narcolepsy, insomnia disorder, hypersomnolence, breathing-related sleep disorders, parasomnias, and restless legs syndrome; disruptive disorders, such as kleptomania, pyromania, intermittent explosive disorder, conduct disorder, and oppositional defiant disorder; depressive disorders, such as disruptive mood dysregulation disorder, major depressive disorder, persistent depressive disorder (dysthymia), premenstrual dysphoric disorder, substance/medication-induced depressive disorder, postpartum depression, and depressive disorder caused by another medical condition, for example, psychiatric and existential distress within life-threatening cancer situations (ACS Pharmacol. Transl. Sci. 4: 553-562; J Psychiatr Res 137: 273-282); substance-related disorders, such as alcohol-related disorders, *cannabis* related disorders, inhalant-use related disorders, stimulant use disorders, and tobacco use disorders; neurocognitive disorders, such as delirium; schizophrenia; compulsive disorders, such as obsessive compulsive disorders (OCD), body dysmorphic disorder, hoarding disorder, trichotillomania disorder, excoriation disorder, substance/medication induced obsessive-compulsive disorder, and obsessive-compulsive disorder related to another medical condition; and personality disorders, such as antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder.

In an aspect, the compounds of the present disclosure may be used to be contacted with a $5\text{-HT}_{2A}$ receptor to thereby modulate the $5\text{-HT}_{2A}$ receptor. Such contacting includes bringing a compound of the present disclosure and $5\text{-HT}_{2A}$ receptor together under in vitro conditions, for example, by introducing the compounds in a sample containing a $5\text{-HT}_{2A}$ receptor, for example, a sample containing purified $5\text{-HT}_{2A}$ receptors, or a sample containing cells comprising $5\text{-HT}_{2A}$ receptors. In vitro conditions further include the conditions described in Example 1 hereof. Contacting further includes bringing a compound of the present disclosure and $5\text{-HT}_{2A}$ receptor together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject. Upon having contacted the $5\text{-HT}_{2A}$ receptor, the compound may activate the $5\text{-HT}_{2A}$ receptor or inhibit the $5\text{-HT}_{2A}$ receptor.

Thus, in a further aspect, the condition that may be treated in accordance herewith can be any $5\text{-HT}_{2A}$ receptor mediated disorder. Such disorders include, but are not limited to schizophrenia, psychotic disorder, attention deficit hyperactivity disorder, autism, and bipolar disorder.

In an aspect, the compounds of the present disclosure may be used to be contacted with a $5\text{-HT}_{1A}$ receptor to thereby modulate the $5\text{-HT}_{1A}$ receptor. Such contacting includes bringing a compound of the present disclosure and $5\text{-HT}_{1A}$ receptor together under in vitro conditions, for example, by introducing the compounds in a sample containing a 5-$HT_{1A}$ receptor, for example, a sample containing purified 5-$HT_{1A}$ receptors, or a sample containing cells comprising 5-$HT_{1A}$ receptors. In vitro conditions further include the conditions described in Example 3 hereof. Contacting further includes bringing a compound of the present disclosure and 5-$HT_{1A}$ receptor together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject. Upon having contacted the 5-$HT_{2A}$ receptor, the compound may activate the 5-$HT_{1A}$ receptor or inhibit the 5-$HT_{1A}$ receptor.

Thus, in a further aspect, the condition that may be treated in accordance herewith can be any 5-$HT_{1A}$ receptor mediated disorder. Such disorders include, but are not limited to schizophrenia, psychotic disorder, attention deficit hyperactivity disorder, autism, and bipolar disorder.

Turning now to methods of making the aldehyde and ketone psilocybin derivatives of the present disclosure, it is initially noted that the aldehyde and ketone psilocybin derivatives of the present disclosure may be prepared in any suitable manner, including by any organic chemical synthesis methods, biosynthetic methods, or a combination thereof.

One suitable method of making the aldehyde and ketone psilocybin derivatives of the present disclosure initially involves selecting and obtaining or preparing a reactant psilocybin derivative compound and selecting and obtaining or preparing a compound selected from an aldehyde or ketone containing compound.

Suitable reactant psilocybin derivative compounds include compounds comprising an indole prototype structure (see: FIG. 2), including, for example, a chemical compound having chemical formula (VI):

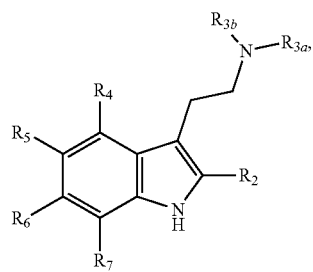

(VI)

wherein, at least one of $R_2$, $R_5$, $R_6$, or $R_7$ is a hydrogen atom, wherein $R_4$ is an O-alkyl group, an O-acyl group, an O-aryl group, an O-alkaryl group, a hydroxy group, a phosphate group, a glycosyloxy group, or a hydrogen atom and wherein $R_{3A}$ and $R_{3B}$ each independently are a hydrogen atom, an oxygen atom an alkyl group, acyl group or an aryl group. Reactant psilocybin derivative compound (VI) comprises a plurality of compounds, some examples of which will next be described.

In one example embodiment, in the compound having formula (VI) $R_{3A}$ and $R_{3B}$ can both be an oxygen atom, or $R_{3a}$ and $R_{3b}$ can both be a hydrogen atom.

Figure 9A:
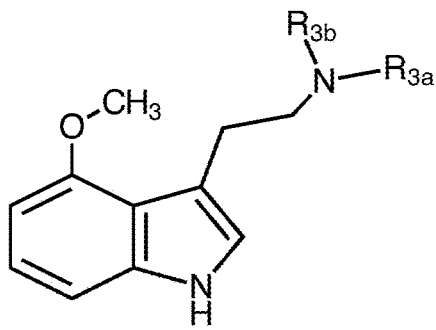
FIGS. 9A, 9B, 9C, 9D, 9E, 9F, 9G, and 9H depict the chemical structures of certain example psilocybin derivatives, notably O-alkylated psilocybin derivatives, notably a 4-O-methyl-psilocybin derivative (FIG. 9A), a 4-O-ethyl-psilocybin derivative (FIG. 9B), a 4-acetyl-psilocybin derivative (FIG. 9C), a 4-propionoyl-psilocybin derivative (FIG. 9D), a 4-hydroxy-psilocybin derivative (FIG. 9E), a 4-phospho-psilocybin derivative (FIG. 9F), a 4-glycosyl-psilocybin derivative (FIG. 9G), and a 4-psilocybin derivative (FIG. 9H).
Figure 9B:
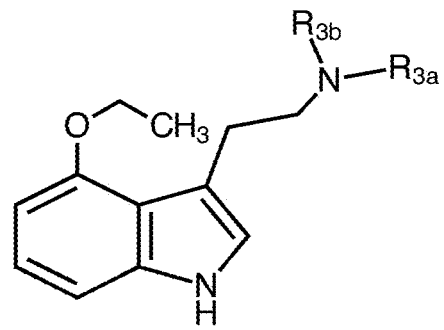

In one example embodiment, the reactant psilocybin derivative can be selected to be a chemical compound wherein $R_4$ is an O-alkyl group, $R_2$, $R_5$, $R_6$, and $R_7$ are a hydrogen atom, and $R_{3A}$ and $R_{3B}$ are a hydrogen atom, an alkyl group, an acyl group, or an aryl group, such as, for example, the reactant psilocybin derivative shown in FIGS. 9A and 9B.

Figure 9C:
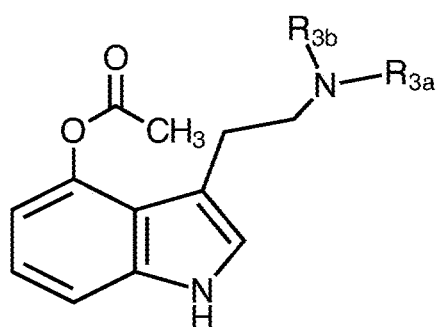
Figure 9D:
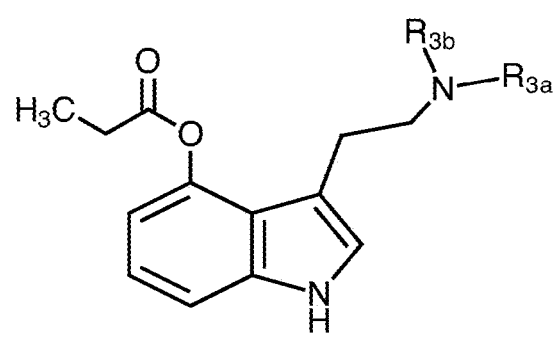

In one example embodiment, the reactant psilocybin derivative can be selected to be a chemical compound wherein $R_4$ is an O-acyl group, $R_2$, $R_5$, $R_6$, and $R_7$ are a hydrogen atom, and $R_{3A}$ and $R_{3B}$ are a hydrogen atom, an alkyl group, an acyl group, or an aryl group, such as, for example, the reactant psilocybin derivative shown in FIGS. 9C and 9D.

Figure 9E:
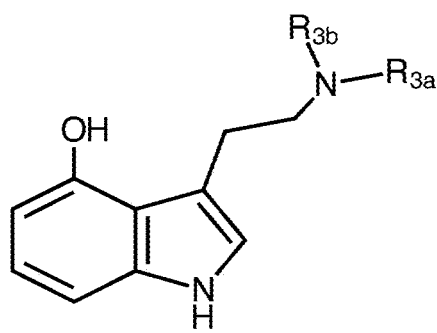

In one example embodiment, the reactant psilocybin derivative can be selected to be a chemical compound wherein $R_4$ is a hydroxyl group, $R_2$, $R_5$, $R_6$, and $R_7$ are a hydrogen atom, and $R_{3A}$ and $R_{3B}$ are a hydrogen atom, an alkyl group, an acyl group, or an aryl group, such as, for example, the reactant psilocybin derivative shown in FIG. 9E.

Figure 9F:
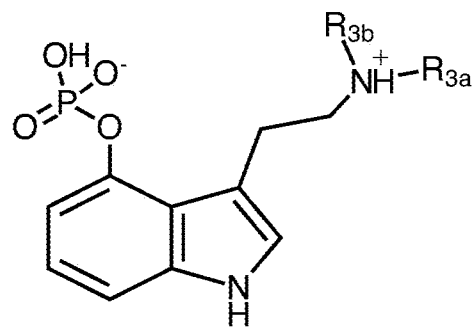

In one example embodiment, the reactant psilocybin derivative can be selected to be a chemical compound wherein $R_4$ is a phosphate group, $R_2$, $R_5$, $R_6$, and $R_7$ are a hydrogen atom, and $R_{3A}$ and $R_{3B}$ are a hydrogen atom, an alkyl group, an acyl group, or an aryl group, such as, for example, the reactant psilocybin derivative shown in FIG. 9F.

Figure 9G:
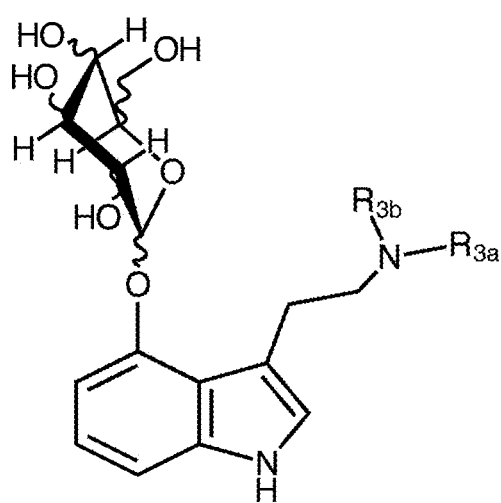

In one example embodiment, the reactant psilocybin derivative can be selected to be a chemical compound wherein $R_4$ is a glycosyloxy group, $R_2$, $R_5$, $R_6$, and $R_7$ are a hydrogen atom, and $R_{3A}$ and $R_{3B}$ are a hydrogen atom, an alkyl group, an acyl group, or an aryl group, such as, for example, the reactant psilocybin derivative shown in FIG. 9G.

Figure 9H:
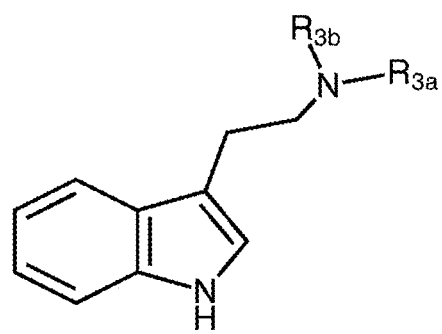

In one example embodiment, the reactant psilocybin derivative can be selected to be a chemical compound wherein $R_4$ is a hydrogen atom, $R_2$, $R_5$, $R_6$, and $R_7$ are a hydrogen atom, and $R_{3A}$ and $R_{3B}$ are a hydrogen atom, an alkyl group, an acyl group, or an aryl group, such as, for example, the reactant psilocybin derivative shown in FIG. 9H.

The reactant psilocybin derivative compounds may be provided in a more or less chemically pure form, for example, in the form of a psilocybin derivative preparation having a purity of at least about 95%, at least about 96%, at least about 97%, at least about 98%, at least about 99%, or at least 99.9%. The psilocybin derivative may be chemically synthesized, or obtained from a fine chemical manufacturer.

The aldehyde or ketone group containing compound may be provided in a more or less chemically pure form, for example, having a purity of at least about 95%, at least about 96%, at least about 97%, at least about 98%, at least about 99%, or at least 99.9%. The aldehyde or ketone group containing compound may be synthesized or purified, or can be conveniently obtained from a fine chemical manufacturer.

Thus, initially, in an aspect hereof, a reactant psilocybin derivative is provided, and the reactant psilocybin derivative is employed to react in a chemical reaction resulting in the formation of an aldehyde or ketone psilocybin derivative compound.

Figure 10A:
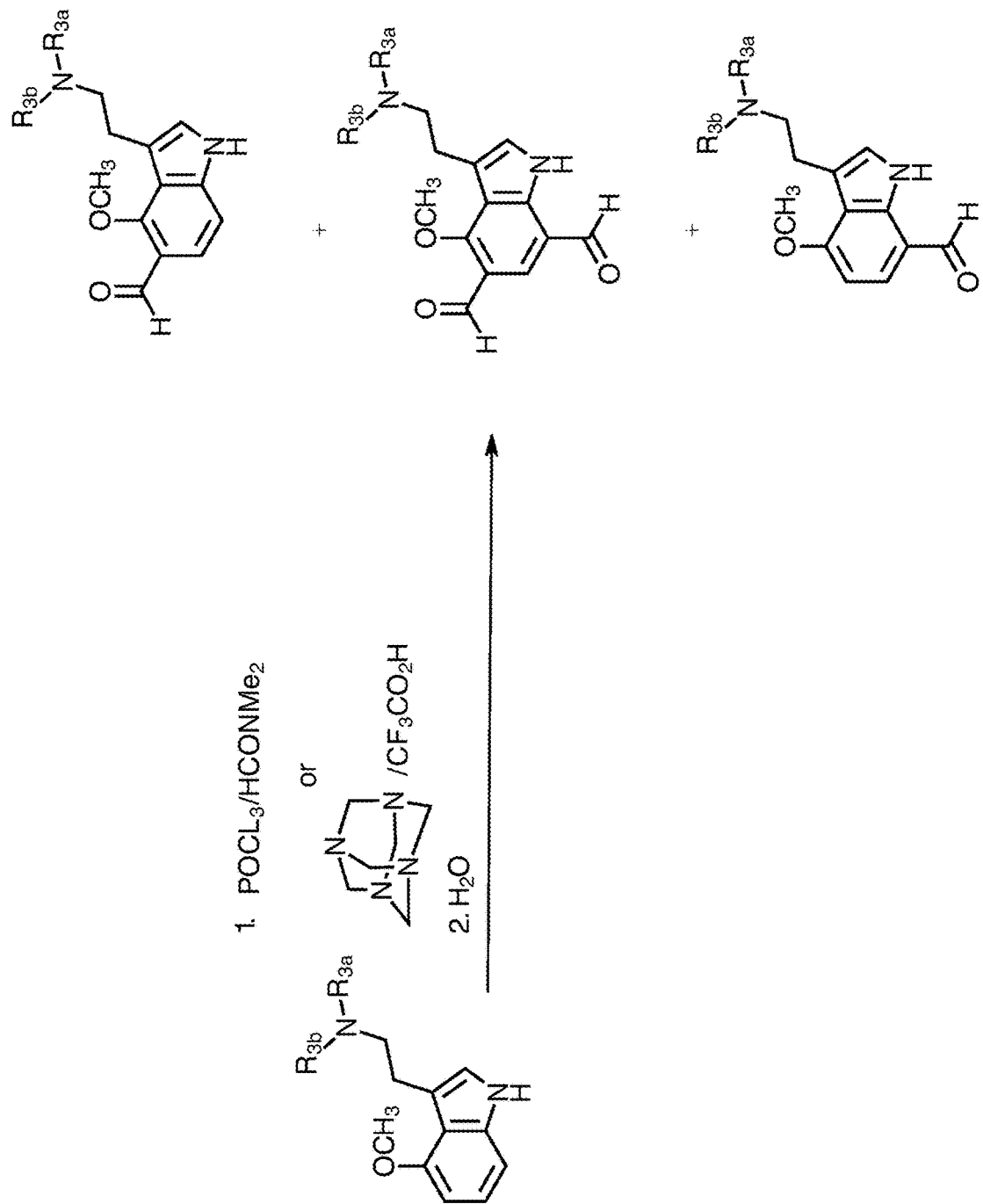
FIGS. 10A, 10B, 10C, 10D, 10E and 10F depict certain example reactions for forming aldehyde psilocybin derivatives.

Referring now to FIG. 10A, shown therein is an example of a chemical reaction wherein a 4-O-methyl-psilocybin derivative (FIG. 9A) is reacted either with a Vilsmeier-Haack reagent (formed by the addition of $POCl_3$ into DMF) or with a hexamine in the presence of an acid (Sommelet reaction), followed by a hydrolysis of the intermediates from both reaction to obtain the desired 4-O-methyl-psilocybin derivatives formylated either at the $C_5$- or $C_7$-position or both the $C_5$- and $C_7$-positions.

Figure 10B:
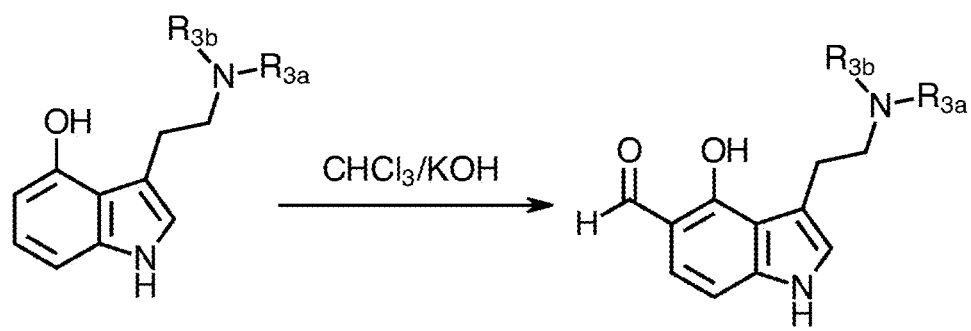

Referring now to FIG. 10B, shown therein is an example of chemical reaction wherein a 4-hydroxy-psilocybin derivative (FIG. 9E) is reacted with chloroform in the presence of a strong base like NaOH (Reimer-Tiemann reaction), to afford the desired 5-formyl-4-hydroxy-psilocybin derivatives.

Figure 10C:
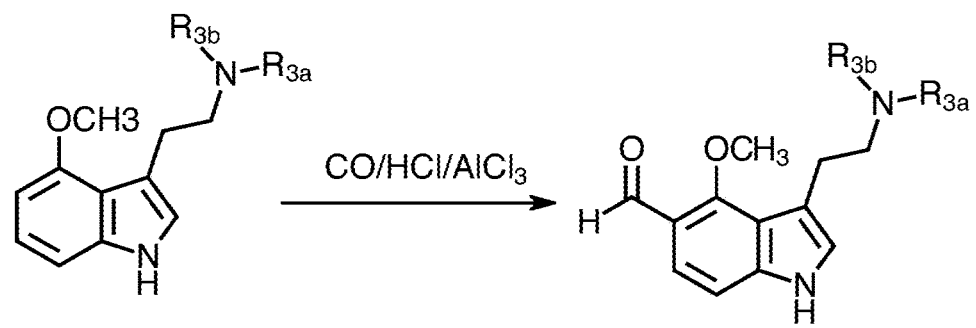

Referring now to FIG. 10C, shown therein is an example of chemical reaction wherein a 4-O-methyl-psilocybin derivative (FIG. 9A) is reacted with carbon monoxide, aluminum chloride and hydrochloric acid which results in the formation of a 6-formyl-4-O-methyl-psilocybin derivative.

Figure 10D:
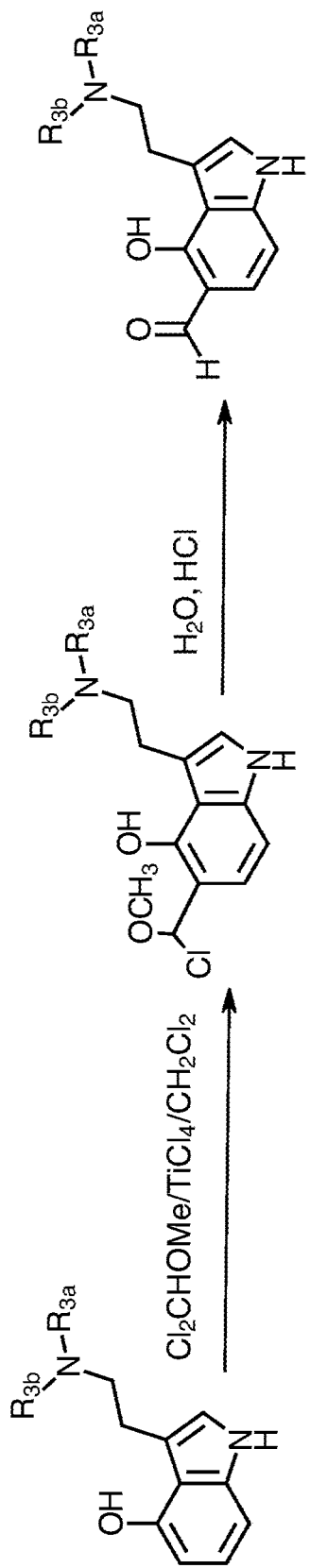

Referring now to FIG. 10D, shown therein is an example of chemical reaction wherein a 4-hydroxy-psilocybin derivative (FIG. 9E) is reacted with dichloromethyl methyl ether in the presence of a strong Lewis acid like titanium tetrachloride, followed by a hydrolysis in the presence of HCl to afford the desired 5-formyl-4-hydroxy-psilocybin derivatives (Rieche formylation).

Figure 10E:
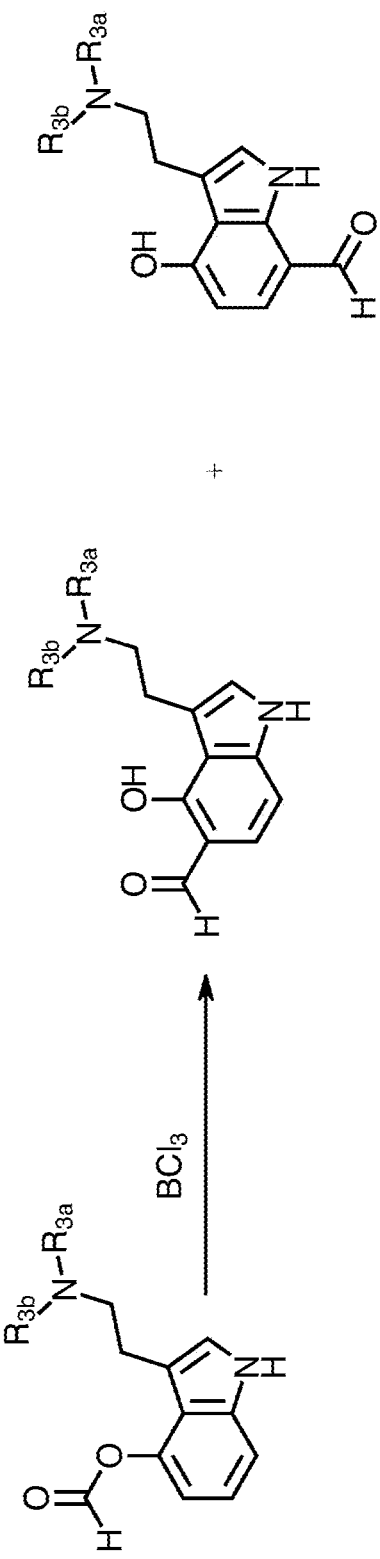

Referring now to FIG. 10E, shown therein is an example of chemical rearrangement reaction wherein a 4-O-formyl-psilocybin derivative is treated with a Lewis acid such as $BCl_3$, to afford the desired either the 5- or 7-formyl-4-hydroxy-psilocybin derivatives (Fries rearrangement).

Figure 10F:
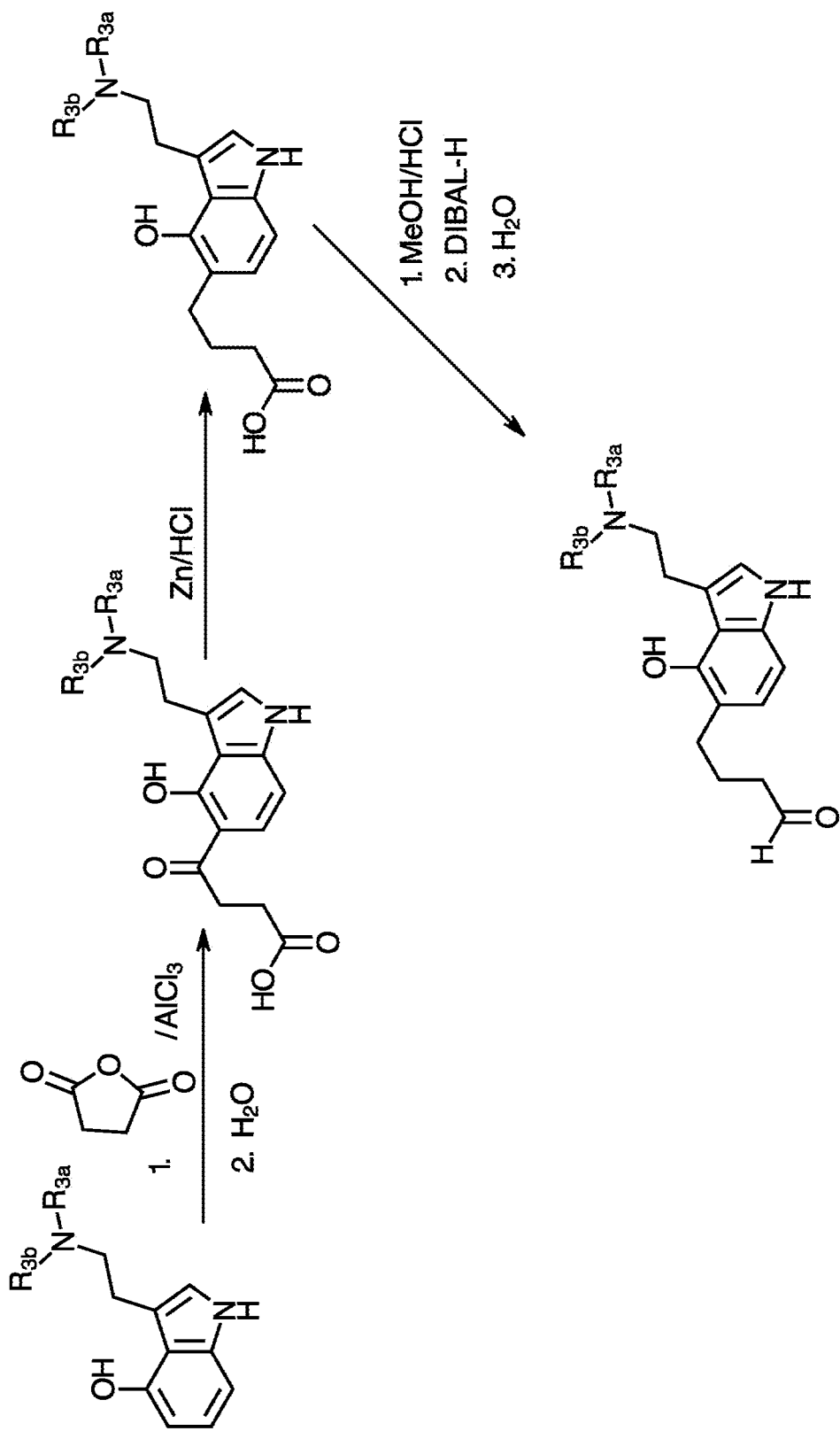

Referring now to FIG. 10F, shown therein is an example of a chemical reaction wherein a 4-O-hydroxy-psilocybin derivative (9E) is treated with a cyclic anhydride, such as succinic anhydride, in the presence of a Lewis acid such as $AlCl_3$, to afford the desired Friedel-Crafts acylation product which undergoes a reduction with zinc and HCl to form the intermediate acid; the acid was further esterified in methanol in the presence of a strong acid (HCl), followed by a controlled reduction with diisobutylaluminum hydride to formed the desired 4-hydroxy-psilocybin bearing a formyl group on the side chain (5-(4-oxobutyl)-4-hydroxy-psilocybin derivatives.

Figure 11A:
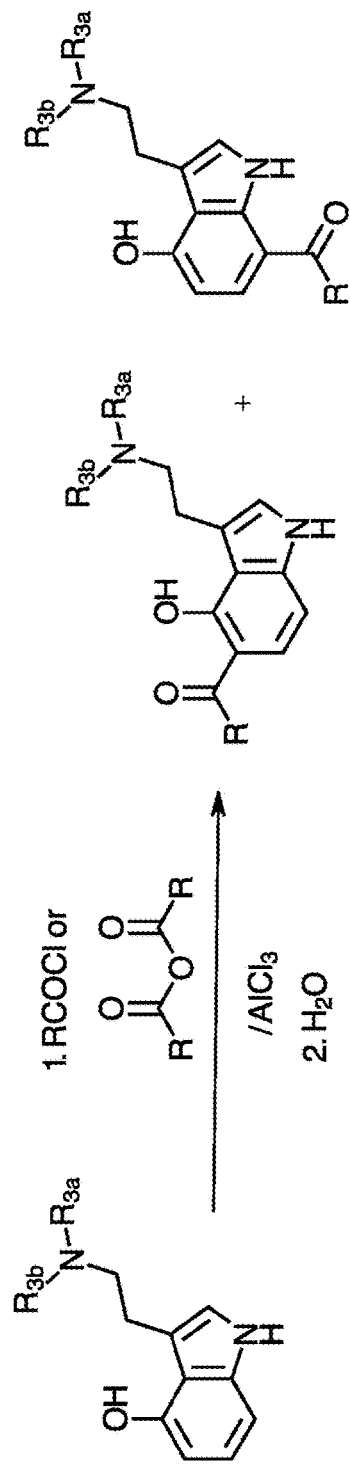
FIGS. 11A, 11B, and 11C depict certain example reactions for forming ketone psilocybin derivatives.

Referring now to FIG. 11A, shown therein is an example of a chemical reaction wherein a 4-hydroxy-psilocybin derivative (FIG. 9E) is reacted with an acyl chloride in the presence of a Lewis acid (Friedel-Crafts acylation reaction), followed by a hydrolysis to form the desired 4-hydroxy-psilocybin derivatives acylated either at the $C_5$- or $C_7$-position or both $C_5$- and $C_7$-positions.

Figure 11B:
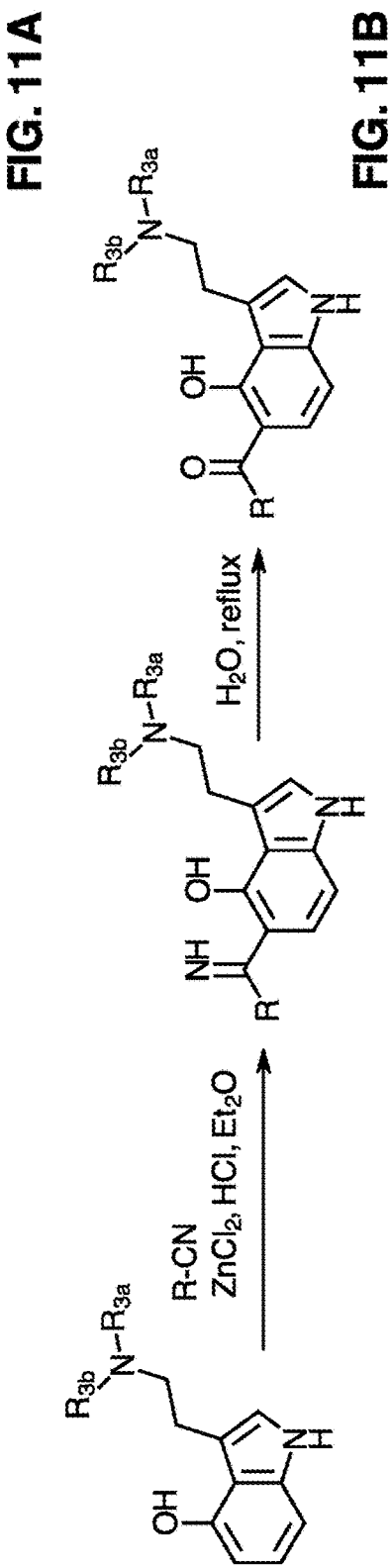

Referring now to FIG. 11B, shown therein is an example of a chemical reaction wherein a 4-hydroxy-psilocybin derivative (FIG. 9E) is reacted with an alkylnitrile or arylnitrile in the presence of zinc chloride and HCl, to form an intermediate imine, followed by a hydrolysis to obtain the desired 4-hydroxy-psilocybin derivatives acylated at the $C_5$-position.

Figure 11C:
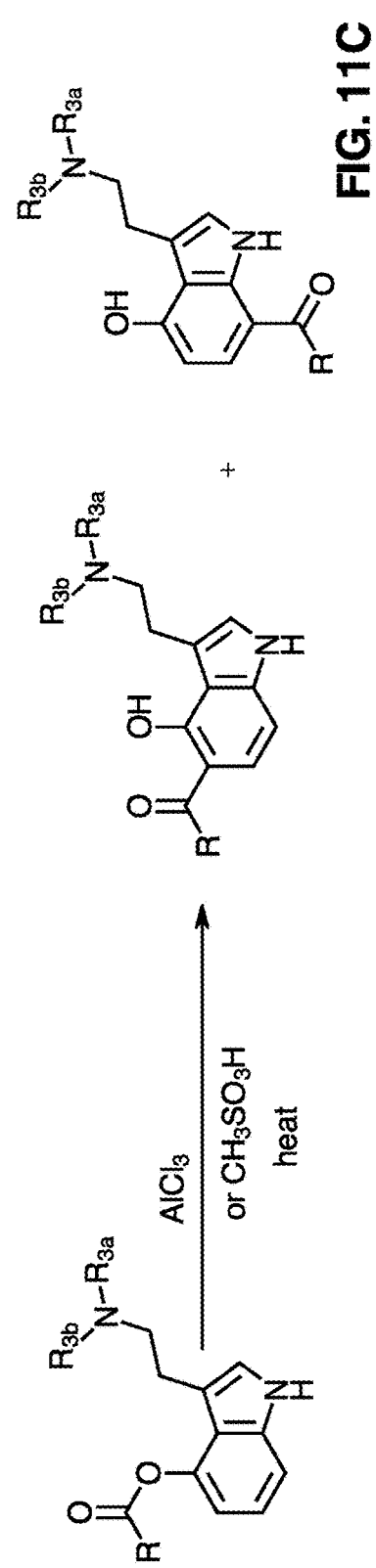

Referring now to FIG. 11C, shown therein is an example of a chemical rearrangement reaction wherein a 4-O-acyl-psilocybin derivative is heated with either a Lewis acid such as $AlCl_3$ or a Bronsted-Lowry acid such as trifluoromethanesulfophic acid, to afford the desired either the 5- or 7-acyl-4-hydroxy-psilocybin derivatives (Fries rearrangement).

Referring next to FIGS. 12A, 12B, 12C and 12F, shown therein are yet further example methods of making aldehyde and ketone derivatives of psilocybin according to the present disclosure.

Figure 12A:
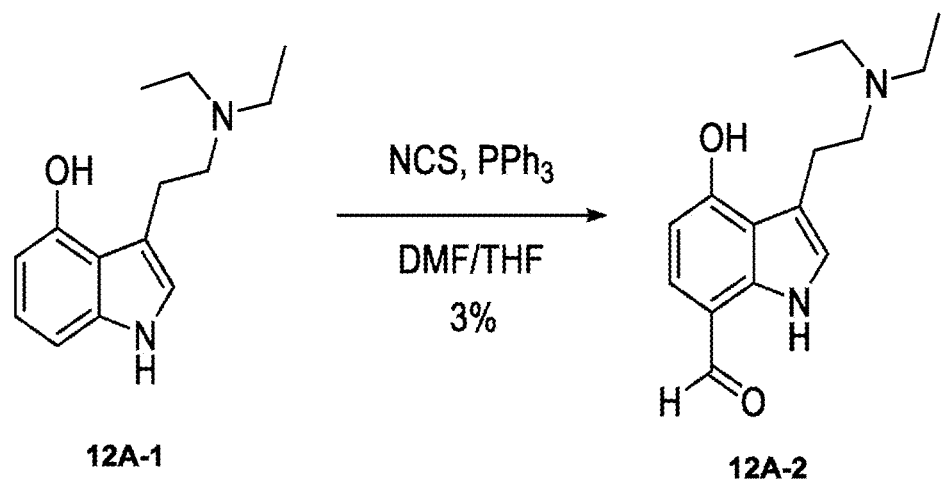
FIGS. 12A, 12B, 12C, 12D, 12E, 12F and 12G depict certain example chemical reactions for forming aldehyde (FIGS. 12A, 12B, 12C, 12E) and ketone psilocybin (FIGS. 12D, 12F and 12G) derivatives, notably
Figure 12B:
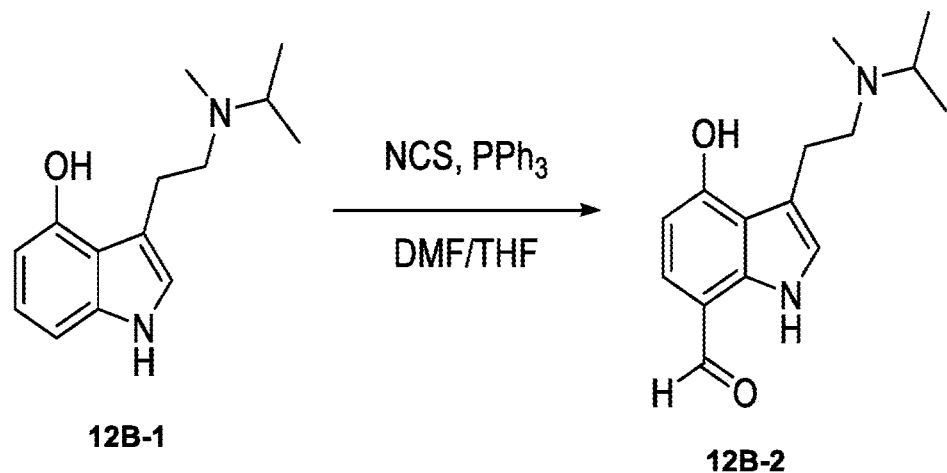
Figure 12C:
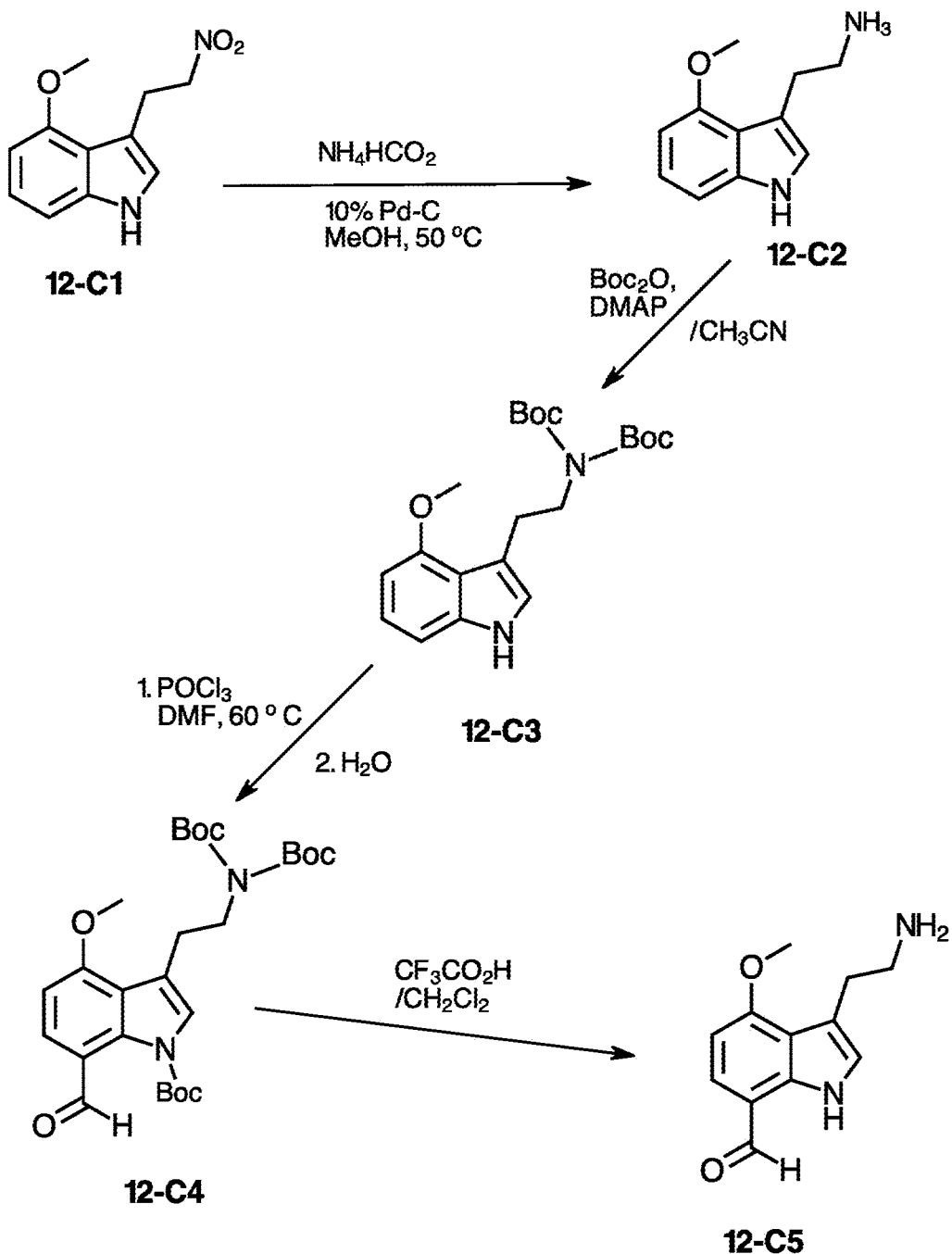

Referring to FIG. 12C shown, therein is an example multistep synthesis for form 4-O-methyl-7-formyl-psilocybin derivative 12C-5 from 4-methoxy-3-(2-nitroethyl)indole (12C-1). The nitro functionality of compound 12C-1 can first be reduced using lithium aluminum hydride to afford the corresponding compound 4-methoxytryptamine (12C-2). Compound 12C-2 can then be fully protected with Boc group using di-tert-butyl dicarbonate in anhydrous acetonitrile in the presence of 4-N,N-dimethylaminopyridine to afford the tri-Boc-protected 4-methoxytryotamine derivative 12C-3 (45% yield). Compound 12C-3 can subsequently be reacted with Vilsmeier reagent, prepared by mixing phosphoryl chloride with anhydrous DMF, followed by a hydrolysis, to then obtain the corresponding 4-methoxy-7-formyl-substituted tryptamine derivative 12C-4. Finally, the two Boc protecting groups on the side-chain N can be removed using trifluoroacetic acid in dichloromethane to provide the desired 4-O-methyl-7-formyl-psilocybin derivative 12C-5.

Figure 12D:
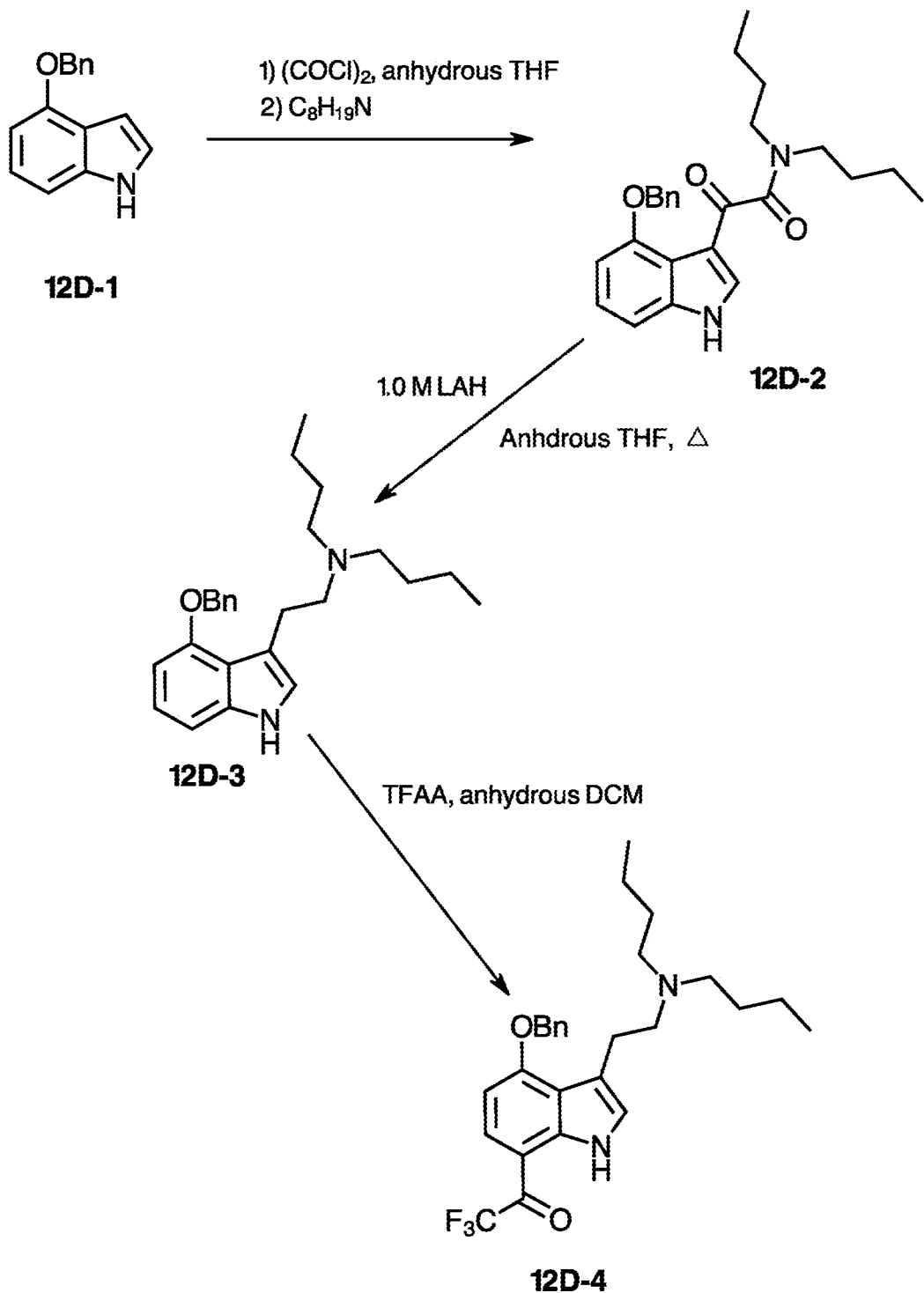
Figure 12E:
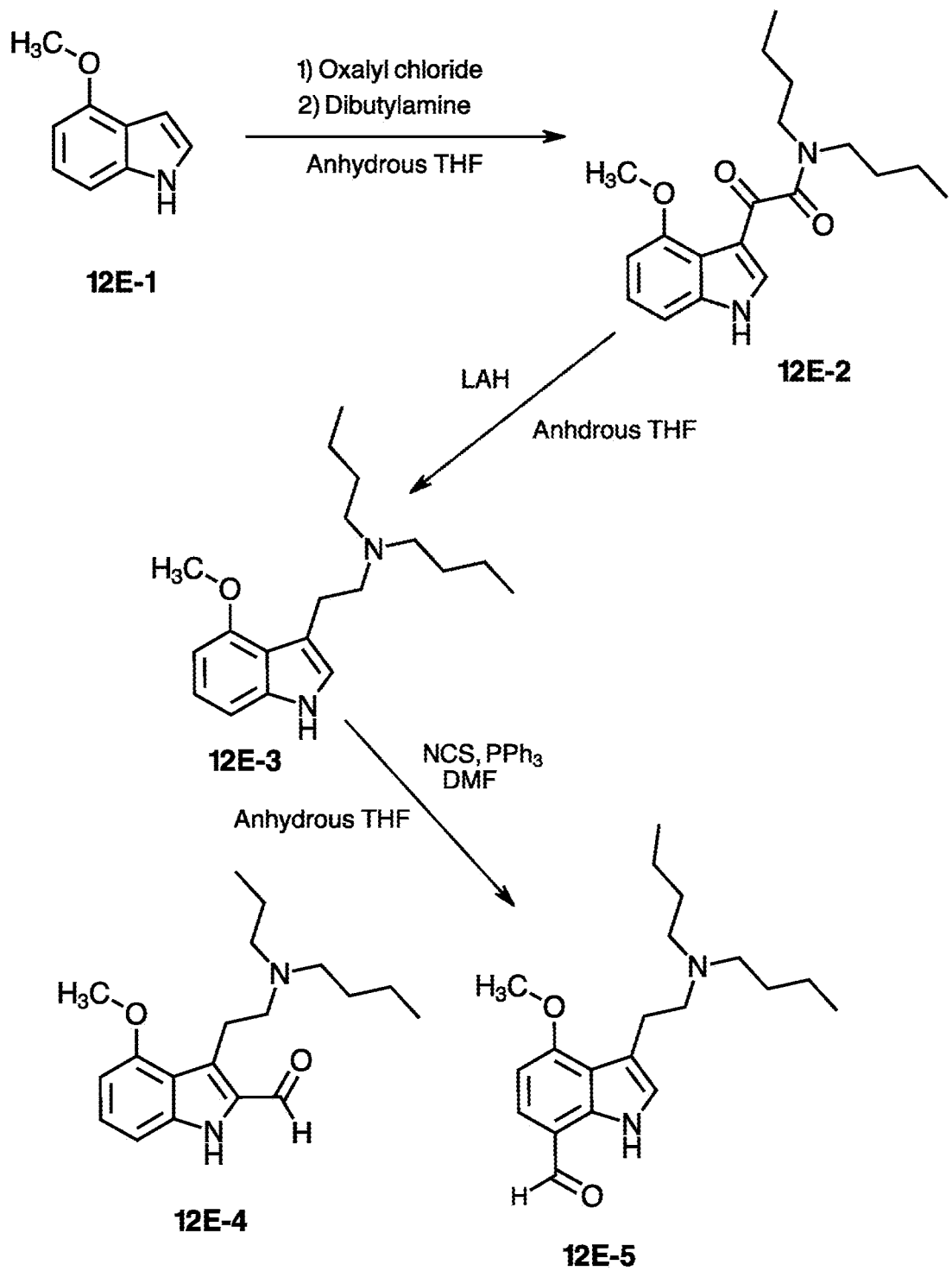
Figure 12F:
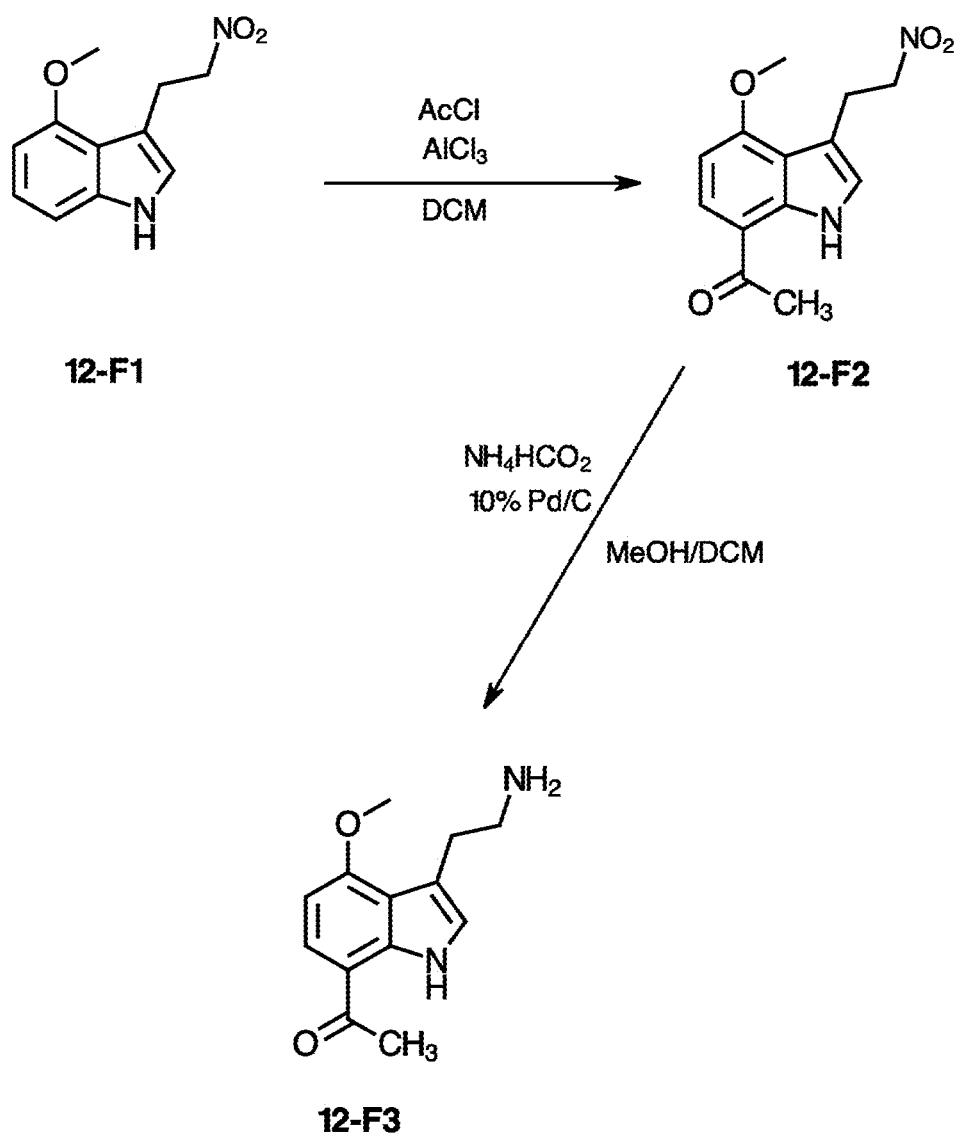

Referring to FIG. 12F shown therein is another example multistep synthesis of a 4-O-methyl-7-acetyl-psilocybin derivative 12F-3 from 4-methoxy-3-(2-nitroethyl)indole (12F-1, same as 12C-1). Compound 12F-1 can directly be subjected to a Friedel-Crafts acylation using acetyl chloride as a reagent and aluminum chloride as a catalyst. This can afford the corresponding 7-acetyl-4-methoxy-3-(2-nitroethyl)indole derivative 12F-2. The nitro functionality can subsequently be reduced by a hydrogenolysis to furnish the desired 7-acetyl-4-O-methyl psilocybin derivative 12F-3, under conditions using ammonium formate as the reagent and 10% palladium on charcoal as the catalyst.

Referring to FIG. 12A, shown therein is an example one-step synthesis of N,N-diethyl-7-formylated psilocybin derivative (12A-2) using N,N-diethyl-psilocin (12A-1) as a starting material. Compound 12A-1 can directly be subjected to a reaction with triphenylphosphine and N-chlorosuccinimide in a mixture of anhydrous DMF-THF at 60° C. The formed intermediate can then subsequently be hydrolyzed to provide directly the desired 7-formylated psilocybin product 12A-2.

Referring to FIG. 12B, shown therein is another example of a one-step synthesis of N-methyl-N-isopropyl-7-formylated psilocybin derivative (12B-2) using N-methyl-N-isopropyl-psilocin (12B-1) as a starting material. Compound 12B-1 can be subjected to a reaction with triphenylphosphine and N-chlorosuccinimide in a mixture of anhydrous DMF-THF at ~60° C., and the formed intermediate can be subjected to a hydrolysis to afford directly the corresponding 7-formylated psilocybin product 12B-2.

Thus, it will now be clear that, in an aspect hereof, the reactant psilocybin derivatives disclosed herein may be reacted with aldehyde or ketone group containing compounds to form the aldehyde and ketone psilocybin derivatives of the present disclosure. Thus, in addition to reactant psilocybin derivative shown in FIG. 9A, the example reactant psilocybin derivatives shown in FIGS. 9B-9H may also be reacted with a suitable aldehyde or ketone group containing reagent to form example aldehyde or ketone psilocybin derivatives of the present disclosure. The 4-O-methyl-psilocybin derivative depicted an FIG. 9A may be reacted to form, for example, the 4-O-methyl-5-formyl-psilocybin derivative depicted in FIG. 6A (as already noted), the 4-O-methyl-7-formyl-psilocybin derivative depicted in FIG. 7A, and the 4-O-methyl-5,7-di-formyl-psilocybin depicted in FIG. 8A.

Figure 6A:
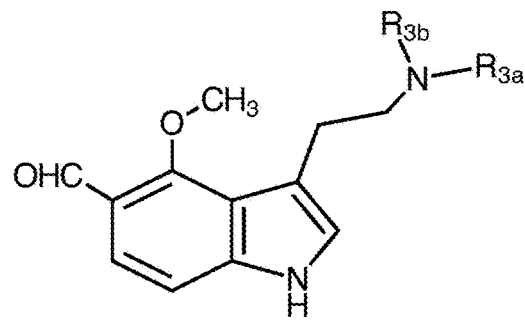
FIGS. 6A, 6B, 6C, 6D, 6E, 6F, 6G, 6H and 6I depict the chemical structures of certain example aldehyde psilocybin derivatives, notably a 4-O-methyl-5-formyl-psilocybin derivative (FIG. 6A), a 4-O-ethyl-5-formyl-psilocybin derivative (FIG. 6B), O-acylated formylated psilocybin derivatives, notably a 4-acetyl-5-formyl-psilocybin derivative (FIG. 6C), a 4-propionoyl-5-formyl-psilocybin derivative (FIG. 6D), a 4-hydroxy-5-formyl-psilocybin derivative (FIG. 6E), and a 4-phospho-5-formyl-psilocybin derivative (FIG. 6F), a 4-glycosyl-5-formyl-psilocybin derivative (FIG. 6G), a 5-formyl-psilocybin derivative (FIG. 6H), and a 4-benzyloxy-5-formyl-psilocybin derivative (FIG. 6I)
Figure 6B:
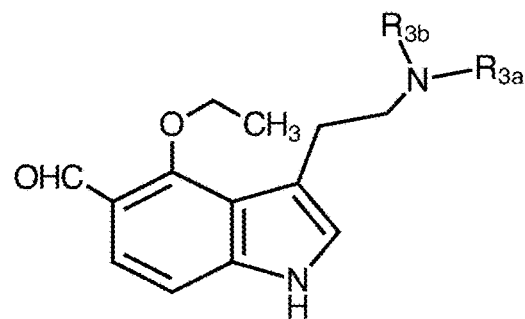
Figure 7A:
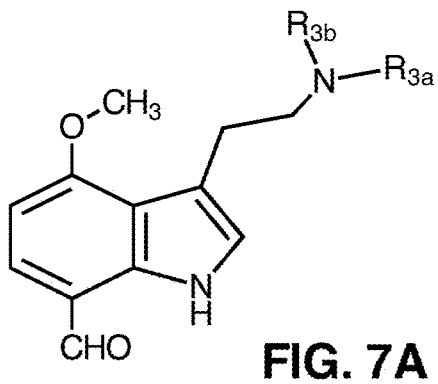
FIGS. 7A, 7B, 7C, 7D, 7E, 7F, 7G, 7H and 7I depict the chemical structures of certain example aldehyde psilocybin derivatives, notably a 4-O-methyl-7-formyl-psilocybin derivative (FIG. 7A), a 4-O-ethyl-7-formyl-psilocybin derivative (FIG. 7B), O-acylated formylated psilocybin derivatives, notably a 4-acetyl-7-formyl-psilocybin derivative (FIG. 7C), a 4-propionoyl-7-formyl-psilocybin derivative (FIG. 7D), a 4-hydroxy-7-formyl-psilocybin derivative (FIG. 7E), a 4-phospho-7-formyl-psilocybin derivative (FIG. 7F), a 4-glycosyl-7-formyl-psilocybin derivative (FIG. 7G), a 7-formyl-psilocybin derivative (FIG. 7H), and a 4-benzyloxy-7-formyl-psilocybin derivative (FIG. 7I).
Figure 7B:
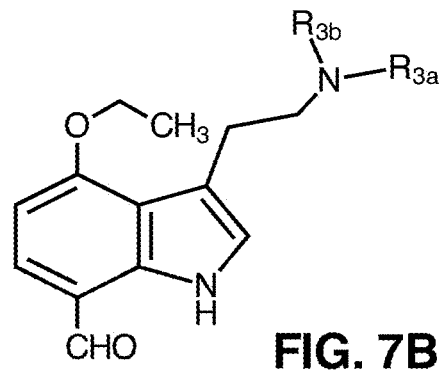
Figure 8A:
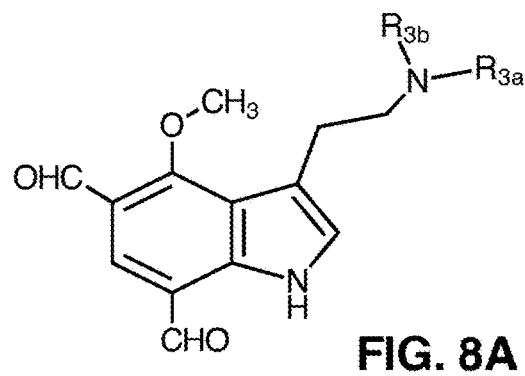
FIGS. 8A, 8B, 8C, 8D, 8E, 8F, 8G, 8H and 8I depict the chemical structures of certain example aldehyde psilocybin derivatives, notably a 4-O-methyl-5,7-di-formyl-psilocybin derivative (FIG. 8A), a 4-O-ethyl-5,7-di-formyl-psilocybin derivative (FIG. 8B), O-acylated formylated psilocybin derivatives, notably a 4-acetyl-5,7-di-formyl-psilocybin derivative (FIG. 8C), a 4-propionoyl-5,7-di-formyl-psilocybin derivative (FIG. 8D), a 4-hydroxy-5,7-di-formyl-psilocybin derivative (FIG. 8E), a 4-phospho-5,7-di-formyl-psilocybin derivative (FIG. 8F), a 4-glycosyl-5,7-di-formyl-psilocybin derivative (FIG. 8G), a 5,7-di-formyl-psilocybin derivative (FIG. 8H), and a 4-benzyloxy-5,7-di-formyl-psilocybin derivative (FIG. 8I).
Figure 8B:
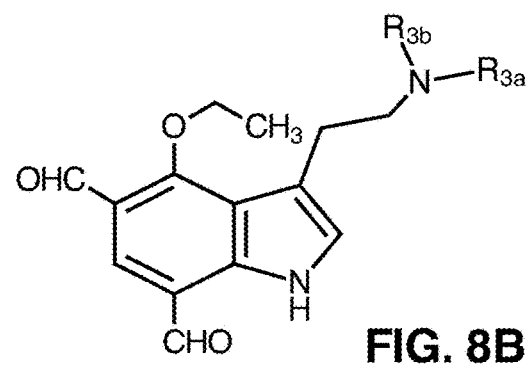

Similarly, the 4-O-ethyl-psilocybin derivative depicted an FIG. 9B may be reacted in similar reaction sequence to form, for example, the 4-O-ethyl-5-formyl-psilocybin derivative depicted in FIG. 6B, the 4-O-ethyl-7-formyl-psilocybin derivative depicted in FIG. 7B, and the 4-O-ethyl-5,7-di-formyl-psilocybin depicted in FIG. 8B.

Figure 6C:
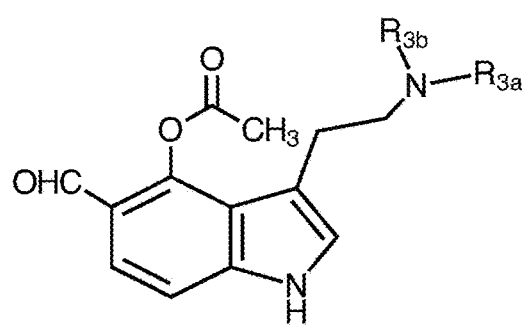
Figure 7C:
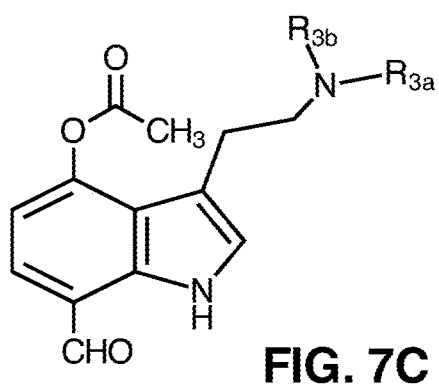
Figure 8C:
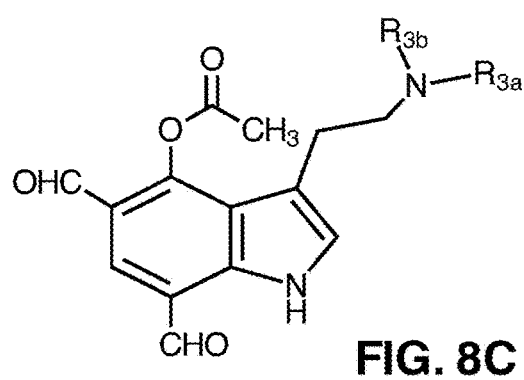
Figure 8D:
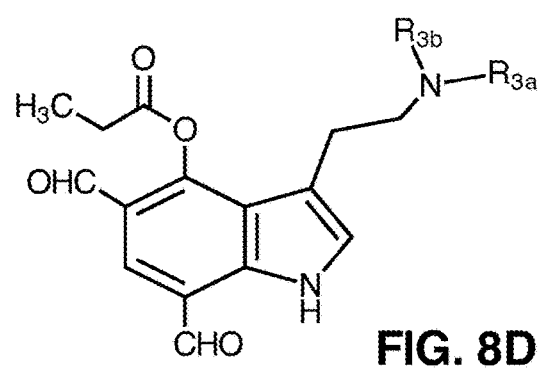
Figure 8E:
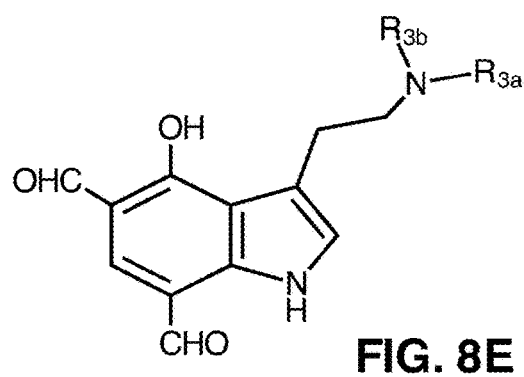
Figure 8F:
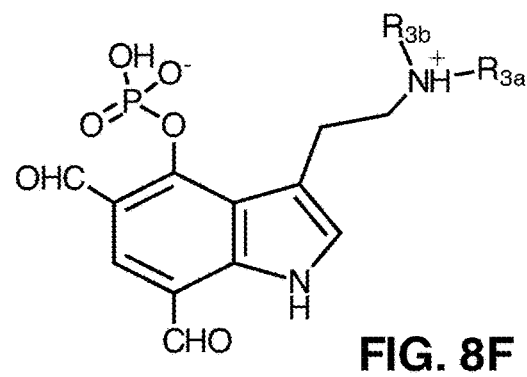
Figure 8G:
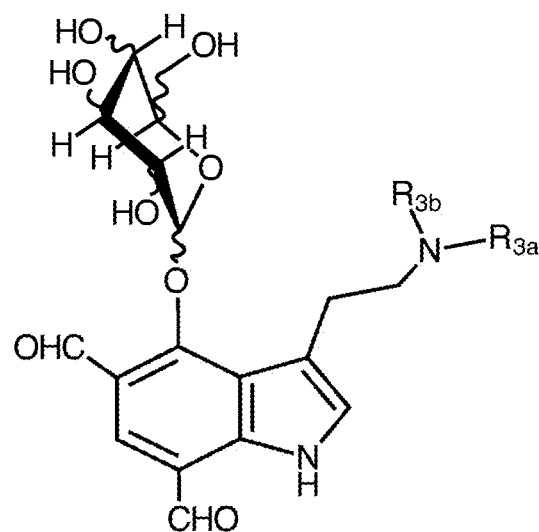
Figure 8H:
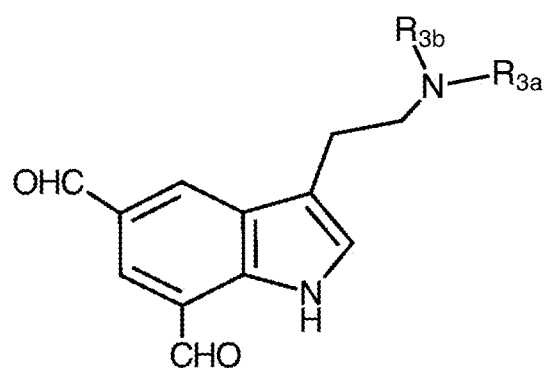
Figure 8I:
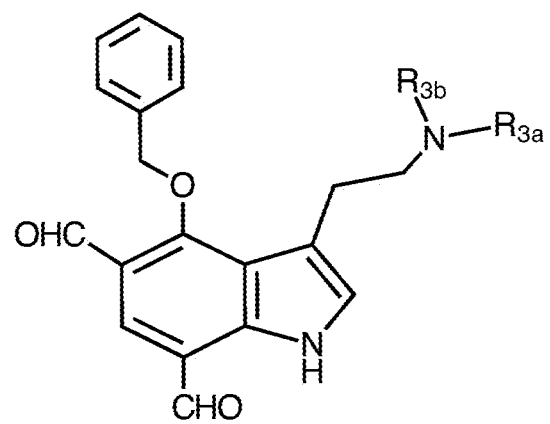

Similarly, the 4-acetyl-psilocybin derivative depicted an FIG. 9C may be reacted in similar reaction sequence to form, for example, the 4-O-acetyl-5-formyl-psilocybin derivative depicted in FIG. 6C, the 4-O-acetyl-7-formyl-psilocybin derivative depicted in FIG. 7C, and the 4-O-acetyl-5,7-di-formyl-psilocybin depicted in FIG. 8C.

Figure 6D:
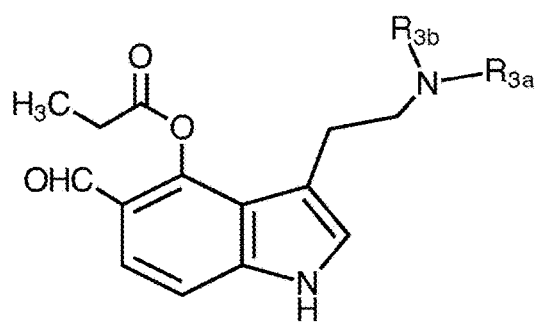
Figure 6E:
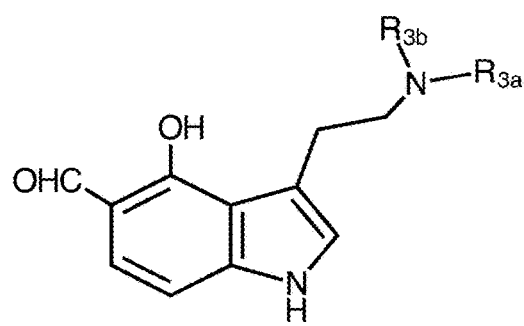
Figure 7D:
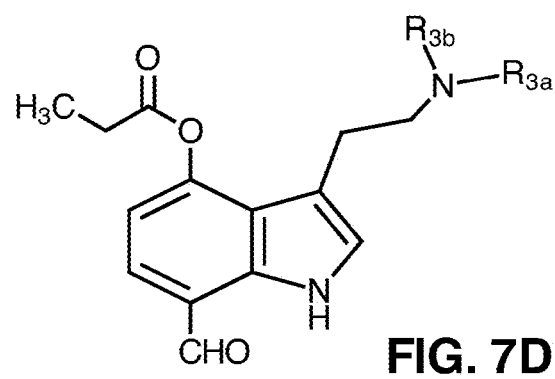
Figure 7E:
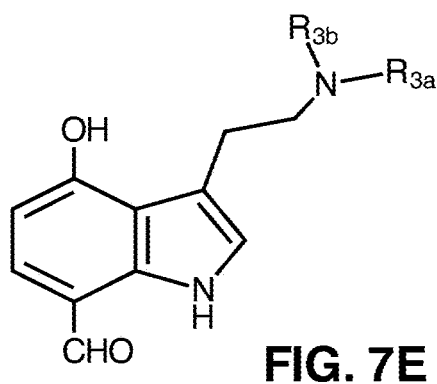
Figure 7F:
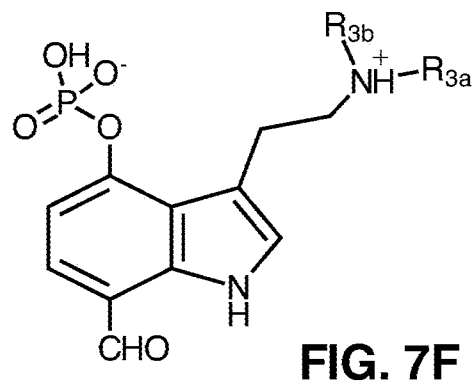
Figure 7G:
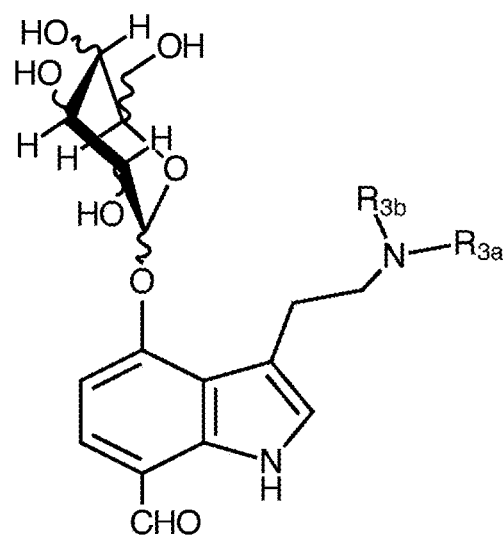
Figure 7H:
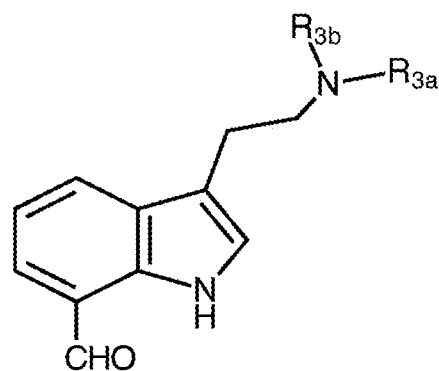
Figure 7I:
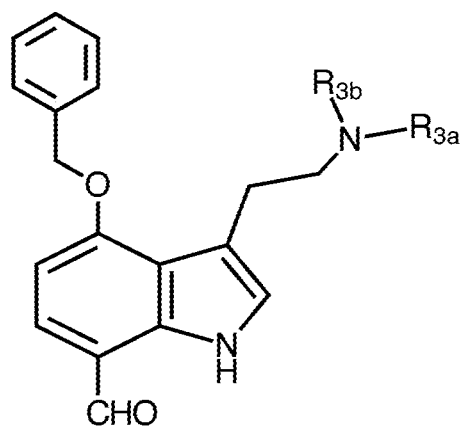

Similarly, the 4-propanoyl-psilocybin derivative depicted an FIG. 9D may be reacted in similar reaction sequence to form, for example, the 4-O-propanoyl-5-formyl-psilocybin derivative depicted in FIG. 6D, the 4-O-propanoyl-7-formyl-psilocybin derivative depicted in FIG. 7D, and the 4-O-propanoyl-5,7-di-formyl-psilocybin depicted in FIG. 7E.

Similarly, the 4-hydroxy-psilocybin derivative depicted an FIG. 9E may be reacted in similar reaction sequence to form, for example, the 4-hydroxy-5-formyl-psilocybin derivative depicted in FIG. 6E, the 4-hydroxy-7-formyl-psilocybin derivative depicted in FIG. 7E, and the 4-hydroxy-5,7-di-formyl-psilocybin depicted in FIG. 8E.

Similarly, the 4-phosphate-psilocybin derivative depicted an FIG. 9F may be reacted in similar reaction sequence to form, for example, the 4-phosphate-5-formyl-psilocybin derivative depicted in FIG. 6F, the 4-phosphate-7-formyl-psilocybin derivative depicted in FIG. 7F, and the 4-phosphate-5,7-di-formyl-psilocybin depicted in FIG. 8F.

Similarly, the 4-O-glycosyl-psilocybin derivative depicted an FIG. 9G may be reacted in similar reaction sequence to form, for example, the 4-O-glycosyl-5-formyl-psilocybin derivative depicted in FIG. 6G, the 4-O-glycosyl-7-formyl-psilocybin derivative depicted in FIG. 7G, and the 4-O-glycosyl-5,7-di-formyl-psilocybin depicted in FIG. 8G.

Similarly, the 4-hydro-psilocybin derivative depicted an FIG. 9H may be reacted to form, for example, the 4-hydro-5-formyl-psilocybin derivative depicted in FIG. 5H, the 4-hydro-7-formyl-psilocybin derivative depicted in FIG. 7H, and the 4-hydro-5,7-di-formyl-psilocybin depicted in FIG. 9H, as well as other analogs.

Similarly, referring to the reaction schemes depicted in FIGS. 12C and 12F, it is possible to use other indole derivatives that have a different substituent at C3, such as 3-(2-aminopropyl)indole or 3-(2-nitropropyl)indole derivatives. The alkyl or aryl substituent at O-4 can be expanded to other homologs, such as 4-O-ethyl, 4-O-propyl, 4-O-benzyl, 4-O-allyl, 4-O-phenyl etc. The substituent at the O-4 position can be expanded to other acyl groups such as 4-O-acetyl, 4-O-phosphoesters (phosphates), 4-O-sulfonyl ester (sulfonates), 4-O-carbonates, 4-O-carbamates, 4-O-glycosyl etc. Additionally, the substituent at C4 can be also replaced with other groups such as hydrogen, halogen, alkyl, aryl, amine, amido groups etc. By adjusting the reaction conditions (e.g., varying of reagent concentrations, temperatures), other products that had a formylation at position(s) other than the 7-positions can be formed and isolated. Furthermore, the reaction schemes, shown in FIGS. 12C and 12F can be relied upon to use other indole derivatives that contain substituent(s) at positions other than $C_4$, such as $C_2$, $C_5$, $C_6$, $C_7$ to form the corresponding formylated and acylated products.

Similarly, referring to the reaction schemes depicted in FIGS. 12A and 12B, it is possible to use other psilocin derivatives that have different substituents at the side chain N. The 4-hydroxy substituent can be expanded to other homologs, such as 4-O-substituent derivatives such as 4-O-aklyl, 4-O-acyl, 4-O-phosphoesters (phosphate), 4-O-sulfonyl ester (sulfonates), 4-O-carbonates, 4-O-carbamates, 4-O-glycosyl etc. Additionally, the substituent at C4 can be also replaced with other groups such as hydrogen, halogen, alkyl, aryl, amine, amido groups etc. By adjusting the reaction conditions (e.g., varying of reagent concentrations, temperatures), other products that had a formylation at position(s) other than the 7-positions can be formed and isolated. Furthermore, the reaction scheme can be further expanded to other indole derivatives that contain substituent(s) at positions other than $C_4$, such as $C_2$, $C_5$, $C_6$, $C_7$ to form the corresponding formylated and acylated products.

Furthermore, it is noted that the performance of the reactions, in example different embodiments, may involve substitution of hydrogen atoms by aldehyde or ketone groups of different carbon atoms, i.e., the $C_2$, $C_5$, $C_6$ and/or $C_7$ atom. In general, reaction conditions may be selected so that hydrogen atoms on different carbon atoms or combinations thereof are substituted by aldehyde groups or ketone groups. The methods can be used to prepare other mono-, di- or multi-aldehyde or ketone psilocybin derivatives.

The reactions may be conducted in any suitable reaction vessel (e.g., a tube, bottle). Suitable solvents that may be used are for example, water, alcohol (such as methanol, ethanol, tetrahydrofuran (THF), N,N-dimethylformamide (DMF), dimethylsulfoxide (DMSO), or a combination of solvents. Suitable temperatures may range from, for example, from about 20° C. to about 100° C. Furthermore, reaction times may be varied. As will readily be appreciated by those of skill in the art, the reaction conditions may be optimized, for example by preparing several psilocybin derivative reactants preparations and reacting these in different reaction vessels under different reaction conditions, for example, at different temperatures, using different solvents, using different catalysts etc., evaluating the obtained aldehyde or ketone psilocybin derivative reaction product, adjusting reaction conditions, and selecting a desired reaction condition. Further general guidance regarding appropriate reaction conditions for performing appropriate reactions may be found in, for example, W. Kantlehner, *Eur. J. Org. Chem.* 2003, 2530-2546, and P. H. Gore, *Chem. Rev.* 1955, 55, 229-281.

It will now be clear from the foregoing that novel aldehyde and ketone psilocybin derivatives are disclosed herein, as well as methods of making aldehyde and ketone psilocybin derivatives. The aldehyde and ketone compounds may be formulated for use as a pharmaceutical drug or recreational drug.

EXAMPLES

Example 1—Preparation of a first aldehyde derivative of psilocybin (a N,N-diethyl-7-formyl derivative)

Preparation of N,N-diethyl-7-formyl psilocybin derivative (12A-2) was performed according to the scheme shown in FIG. 12A using N,N-diethyl-psilocin (12A-1) as a starting material. Thus, referring to FIG. 12A, the synthesis involved the direct formylation of compound 12A-1. To a solution of triphenylphosphine (0.68 g, 2.59 mmol) in anhydrous THF (6.0 mL), was added N-chlorosuccinimide (0.34 g, 2.55 mmol), and the reaction mixture was stirred at room temperature for 30 minutes then cooled in an ice-water bath. Anhydrous DMF (0.40 mL) was added, and the reaction mixture was stirred for another 10 minutes. To the reaction mixture, was added N,N-diethyl-psilocin (12A-1, 0.20 g, 0.86 mmol), and the mixture was heated at 60° C. for 23 hours. The reaction mixture was basified with 10% NaOH to pH 9-10, and the mixture was stirred at room temperature for an hour before being neutralized with concentrated hydrochloric acid to pH 7-8. The solution was extracted with dichloromethane (2×40 mL), and the combined organic solutions was washed with brine (40 mL), dried over anhydrous $Na_2SO_4$, and concentrated in vacuo. The crude product was purified by flash chromatography on silica gel using a gradient of dichloromethane-MeOH (100:0→90:10) to afford compound 12A-2 (see: FIG. 12A) as a brown solid. Yield: 3%. $^1$H NMR (400 MHz, $CD_3OD$) δ 9.53 (s, 1H), 7.41 (d, J=8.3 Hz, 1H), 6.97 (s, 1H), 6.34 (d, J=8.3 Hz, 1H), 3.19 (s, 4H), 3.00 (q, J=7.3 Hz, 4H), 1.20 (t, J=7.3 Hz, 6H). $^{13}$C NMR (100 MHz, $CD_3OD$) δ 8.05, 22.85, 48.21, 56.00, 109.10, 111.29, 112.68, 117.93, 121.04, 134.45, 137.37, 168.87, 188.59. HRMS (ESI, positive) m/z for $C_{15}H_{21}N_2O_2$ [M+H]$^+$ calc'd. 261.1598, found 261.1595. Purity was determined to be 95%. It is noted that compound 12A-2 corresponds with the chemical compound having formula (VIII):

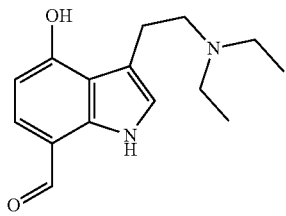

(VIII)

set forth herein.

Figure 13A:
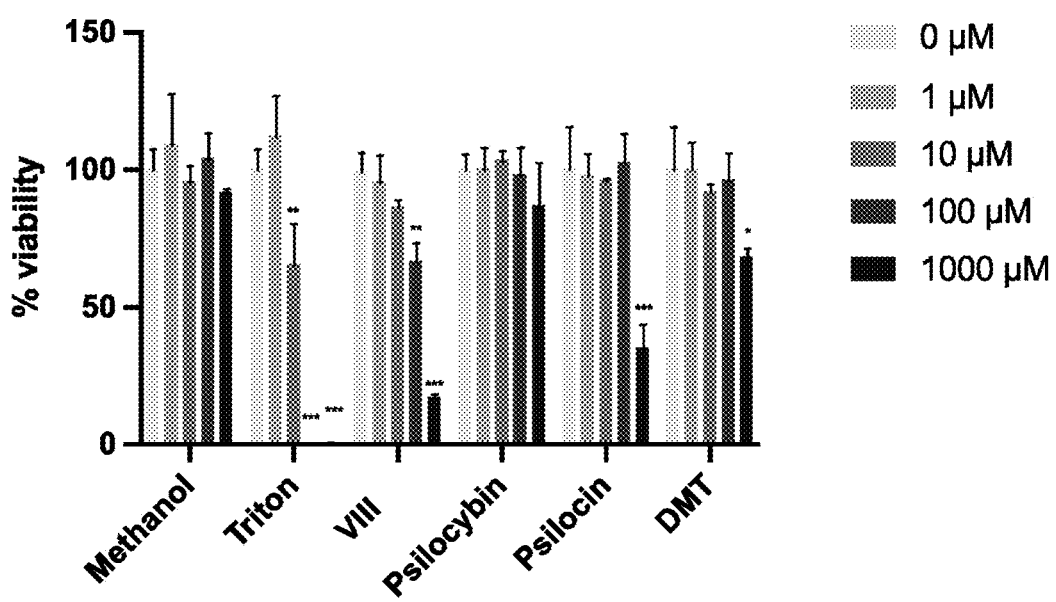
FIGS. 13A, 13B, 13C, 13D, 13E and 13F depict various graphs, obtained in the performance of experimental assays to evaluate the efficacy of an example aldehyde psilocybin derivative having the chemical formula (VIII) set forth herein, notably a cell viability assay (FIG. 13A), a saturation binding assay for [$^3$H]ketanserin at the 5-HT$_{2A}$ receptor (FIG. 13B), a competition assay for psilocin as a positive control (binding) (FIG. 13C), a competition assay for tryptophan as a negative control (no binding) (FIG. 13D), a competition assay for a aldehyde psilocybin derivative compound with formula (VIII), designated "VIII" (FIG. 13E), and a cAMP assay in the presence of constant (4 μM) forskolin but with increasing concentration of an aldehyde psilocybin compound having formula (VIII), designated "X" in +5HT$_{1A}$ cells and −5HT$_{1A}$ cells (FIG. 13F).

Assessment of Cell Viability Upon Treatment of an Aldehyde Psilocybin Derivative To establish suitable ligand concentrations for competitive binding assays, PrestoBlue assays were first performed. The PrestoBlue assay measures cell metabolic activity based on tetrazolium salt formation, and is a preferred method for routine cell viability assays (Terrasso et al., 2017, J Pharmacol Toxicol Methods 83: 72). Results of these assays were conducted using both control ligands (e.g., psilocybin, psilocin, DMT) and novel derivatives, in part as a pre-screen for any remarkable toxic effects on cell cultures up to concentrations of 1 mM. A known cellular toxin (Triton X-100, Pyrgiotakis G. et al., 2009, Ann. Biomed. Eng. 37: 1464-1473) was included as a general marker of toxicity. Drug-induced changes in cell health within simple in vitro systems such as the HepG2 cell line are commonly adopted as first-line screening approaches in the pharmaceutical industry (Weaver et al., 2017, Expert Opin Drug Metab Toxicol 13: 767). HepG2 is a human hepatoma that is most commonly used in drug metabolism and hepatotoxicity studies (Donato et al., 2015, Methods Mol Biol 1250: 77). Herein, HepG2 cells were cultured using standard procedures using the manufacture's protocols (ATCC, HB-8065). Briefly, cells were cultured in Eagle's minimum essential medium supplemented with 10% fetal bovine serum and grown at 37° C. in the presence of 5% $CO_2$. To test the various compounds with the cell line, cells were seeded in a clear 96-well culture plate at 20,000 cells per well. After allowing cells to attach and grow for 24 hours, compounds were added at 1 µM, 10 µM, 100 µM, and 1 mM. Methanol was used as vehicle, at concentrations 0.001, 0.01, 0.1, and 1%. As a positive control for toxicity, TritonX concentrations used were 0.0001, 0.001, 0.01 and 0.1%. Cells were incubated with compounds for 48 hours before accessing cell viability with the PrestoBlue assay following the manufacture's protocol (ThermoFisher Scientific, P50200). PrestoBlue reagent was added to cells and allowed to incubate for 1 hour before reading. Absorbance readings were performed at 570 nm with the reference at 600 nm on a SpectraMax iD3 plate reader. Non-treated cells were assigned 100% viability. Bar graphs show the mean+1- SD, n=3. Significance was determined by 2-way ANOVA followed by Dunnett's multiple comparison test and is indicated by * (P<0.0001), (P<0.001), *(P<0.005). Data acquired for the derivative having chemical formula (VIII) is displayed as "VIII" on the x-axis of FIG. 13A Radioligand receptor binding assays.

Figure 13B:
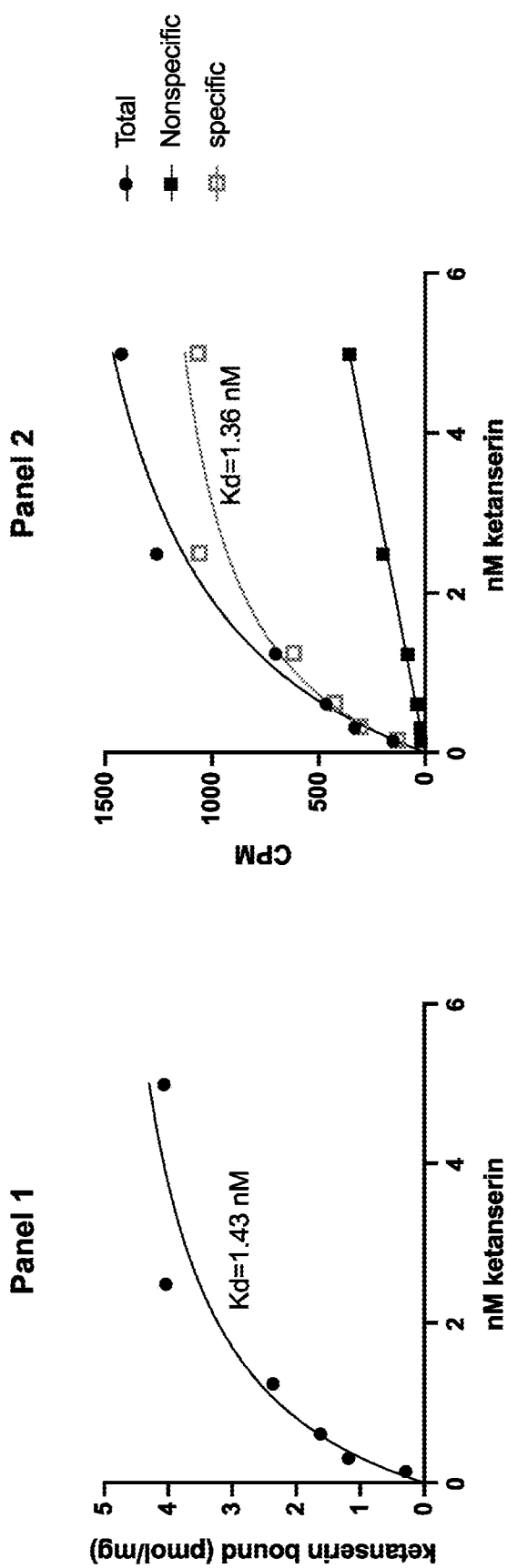
Figure 13C:
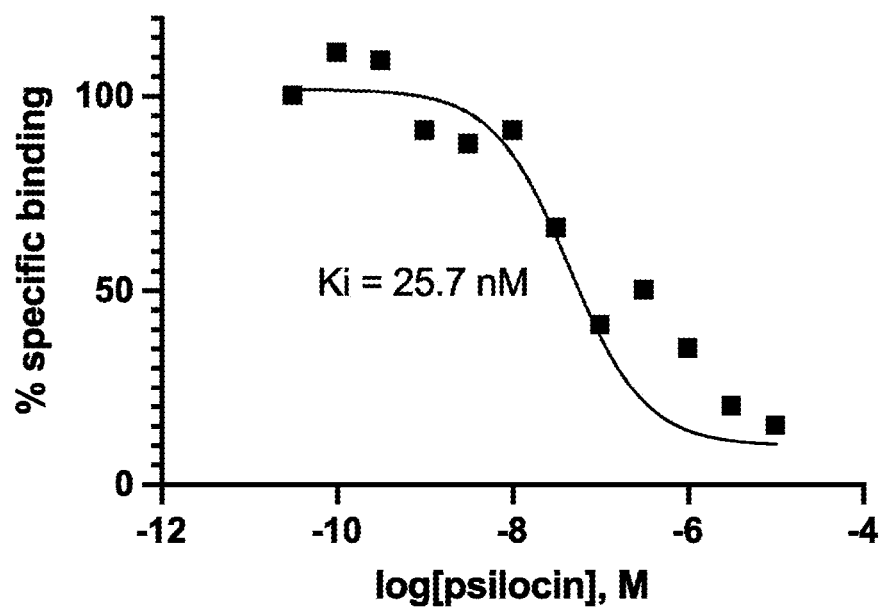
Figure 13D:
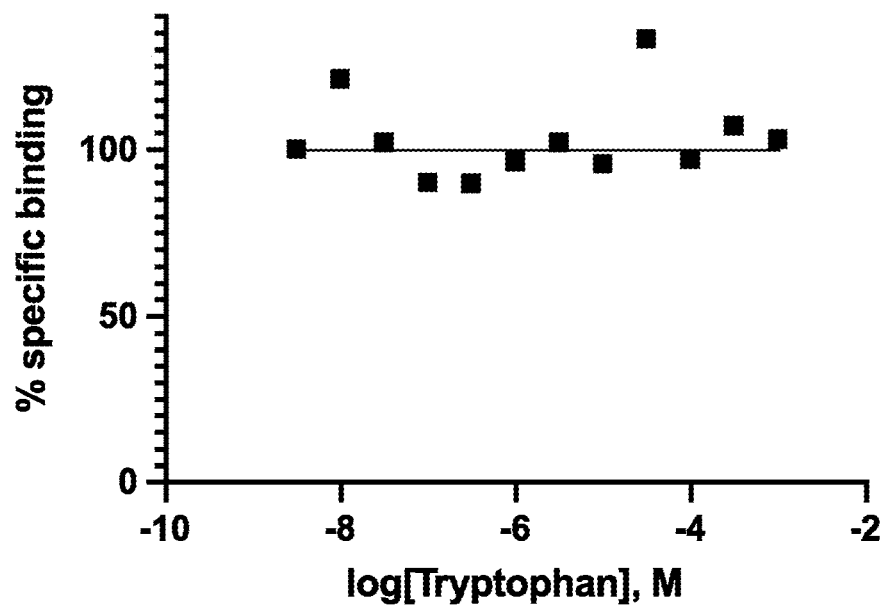
Figure 13E:
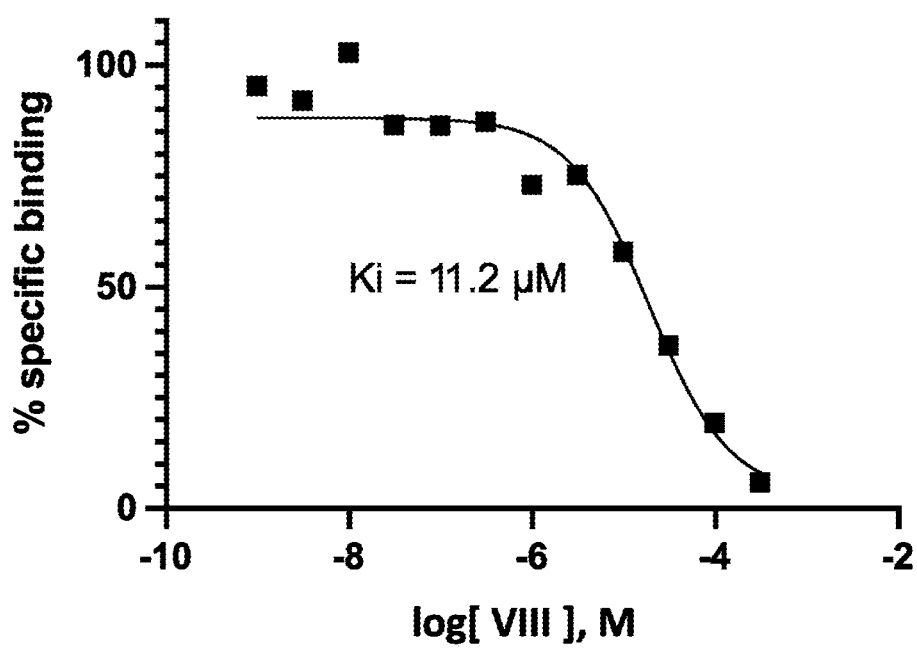

Evaluation of drug binding is an essential step to characterization of all drug-target interactions (Fang 2012, Exp Opin Drug Discov 7:969). The binding affinity of a drug to a target is traditionally viewed as an acceptable surrogate of its in vivo efficacy (Núñez et al., 2012, Drug Disc Today 17: 10). Competition assays, also called displacement or modulation binding assays, are a common approach to measure activity of a ligand at a target receptor (Flanagan 2016, Methods Cell Biol 132: 191). In these assays, standard radioligands acting either as agonists or antagonists are ascribed to specific receptors. In the case of G protein-coupled receptor 5-$HT_{2A}$, [$^3$H]ketanserin is a well-established antagonist used routinely in competition assays to evaluate competitive activity of novel drug candidates at the 5-$HT_{2A}$ receptor (Maguire et al., 2012, Methods Mol Biol 897: 31). Thus, to evaluate activity of novel psilocybin derivatives at the 5-$HT_{2A}$ receptor, competition assays using [$^3$H]ketanserin were employed as follows. SPA beads (RPNQ0010), [$^3$H] ketanserin (NET1233025UC), membranes containing 5-$HT_{2A}$ (ES-313-M400UA), and isoplate-96 microplate (6005040) were all purchased from PerkinElmer. Radioactive binding assays were carried out using Scintillation Proximity Assay (SPA). For saturation binding assays, mixtures of 10 ug of membrane containing 5-$HT_{2A}$ receptor was pre-coupled to 1 mg of SPA beads at room temperature in a tube rotator for 1 hour in binding buffer (50 mM Tris-HCl pH7.4, 4 mM $CaCl_2$), 1 mM ascorbic acid, 10 µM pargyline HCl). After pre-coupling, the beads and membrane were aliquoted in an isoplate-96 microplate with increasing amounts of [$^3$H]ketanserin (0.1525 nM to 5 nM) and incubated for two hours at room temperature in the dark with shaking. After incubation, the samples were read on a MicroBeta 2 Microplate Counter (Perkin Elmer). Determination of non-specific binding was carried out in the presence of 20 µM of spiperone (S7395-250MG, Sigma). Equilibrium binding constants for ketanserin ($K_d$) were determined from saturation binding curves using the 'one-site saturation binding analysis' method of GraphPad PRISM software (Version 9.2.0). Competition binding assays were performed using fixed (1 nM) [$^3$H]ketanserin and different concentrations of tryptophan (3 nM to 1 mM), psilocin (30 pM to 10 µM) or unlabeled test compound (3 nM to 1 mM) similar to the saturation binding assay. $K_i$ values were calculated from the competition displacement data using the competitive binding analysis from GraphPad PRISM software. Tryptophan was included as a negative control as it has no activity at the 5-$HT_{2A}$ receptor. In contrast, psilocin was used as a positive control since it has established binding activity at the 5-$HT_{2A}$ receptor (Kim et al., 2020, Cell 182: 1574). FIG. 13B depicts the saturation binding curves for [$^3$H]ketanserin at the 5-$HT_{2A}$ receptor. Panel 1 shows the specific saturation ligand binding of [$^3$H]ketanserin (from 0.1525 nM to 5 nM) to membranes containing 5-$HT_{2A}$ receptor, which was obtained after subtracting non-specific binding values (shown in Panel 2). Specific binding in counts per minute (cpm) was calculated by subtracting non-specific binding from total binding. Specific binding (pmol/mg) was calculated from pmol of [$^3$H]ketanserin bound per mg of protein in the assay. The $K_d$ was calculated by fitting the data with the one-site binding model of PRISM software (version 9.2.0). FIG. 13C shows the competition binding curve for psilocin as a positive control (binding). FIG. 13D shows the competition binding curve for tryptophan as a negative control (no binding). FIG. 13E shows competition binding curve for compound with formula (VIII), designated "VIII" in the figure.

Figure 13F:
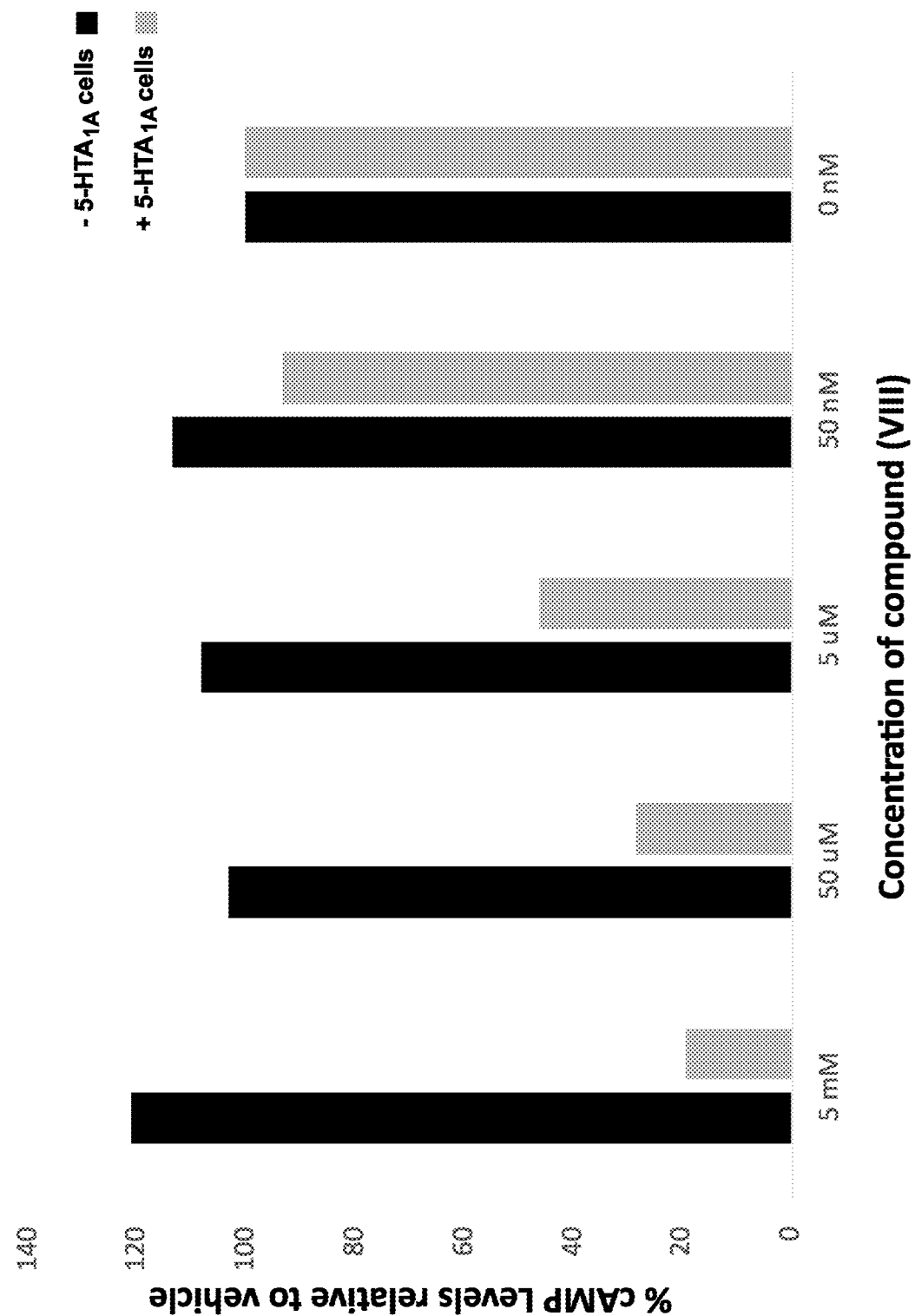

Cell Lines and Control Ligands Used to Assess Activity at 5-$HT_{1A}$ and Experimental Procedures Assessing 5-$HT_{1A}$ Modulation Cell lines, cell line maintenance, and experimental procedures assessing modulation of 5-$HT_{1A}$ were performed as described in Example 3, except that compound (VIII) was evaluated in place of compound (X). FIG. 13F illustrates increased % cAMP levels in the presence of fixed (4 mM) forskolin as dosages of compound (VIII) decrease, revealing 5-$HT_{1A}$ modulation activity of compound (VIII) in +5$HT_{1A}$ cell cultures. Conversely, this trend of increasing % cAMP levels with decreasing compound (VIII) is not observed in −5$HT_{1A}$ cell cultures. It is noted that compound (VIII) is depicted as "VIII" along the x-axis.

Example 2—Preparation of a Second Aldehyde Derivative of Psilocybin (a N-Methyl-N-Isopropyl-7-Formyl Derivative)

Preparation of N-methyl-N-isopropyl-7-formyl psilocybin derivative (12B-2) was performed according to the scheme shown in FIG. 12B using N-methyl-N-isopropyl-psilocin (12B-1) as a starting material. Thus, referring to FIG. 12B, the synthesis involved the direct formylation of compound 12B-1. To a solution of triphenylphosphine (2.04 g, 7.77 mmol) in anhydrous THF (18.0 mL) was added N-chlorosuccinimide (1.02 g, 7.64 mmol), and the reaction mixture was stirred at room temperature for 30 minutes then cooled in an ice-water bath. Anhydrous DMF (1.2 mL) was added, and the reaction mixture was stirred for another 10 minutes. To the reaction mixture, was added 4-hydroxy-N-methyl-N-isopropyltryptamine (12B-1, 0.60 g, 2.58 mmol), and the reaction mixture was heated at 61° C. for 23 hours. The reaction mixture was basified with 10% NaOH to pH 9-10, and the reaction mixture was stirred at room temperature for an hour before being neutralized with concentrated hydrochloric acid to pH 7-8. The reaction mixture was extracted with dichloromethane (2×60 mL), and the combined organic solutions was washed with brine (60 mL), dried over anhydrous $Na_2SO_4$, and concentrated in vacuo. The crude product was purified by flash chromatography on silica gel using a gradient of dichloromethane-MeOH (100:0→90:10) to afford compound 12B-2 (see: FIG. 12B) as a brown oil. Yield: 8%. $^1$H NMR (400 MHz, CD3OD) δ 9.54 (s, 1H), 7.41 (d, J=8.3 Hz, 1H), 6.98 (s, 1H), 6.35 (d, J=8.3 Hz, 1H), 3.30-3.24 (m, 1H), 3.19-3.12 (m, 4H), 2.68 (s, 3H), 1.17 (d, J=6.7 Hz, 6H). HRMS (ESI, positive) m/z for $C_{15}H_{21}N_2O_2[M+H]^+$ calc'd. 261.1598, found 261.1594. Purity was determined to be 95%. It is noted that compound 12B-2 corresponds with the chemical compound having formula (IX):

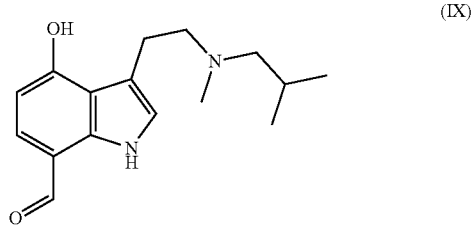 [SMILES: CC(C)CN(C)CCc1c[nH]c2c(C=O)ccc(O)c12]

(IX)

set forth herein.

Example 3—Preparation of a Third Aldehyde Derivative of Psilocybin (a 4-O-Methyl-7-Formyl Derivative)

Preparation of 4-O-methyl-7-formyl psilocybin derivative was performed according to the scheme shown in FIG. 12C using 4-O-methyl-3-(2-nitroethyl)indole (12C-1) as a starting material. Thus, referring to FIG. 12C, the first step involved the reduction of nitro functionality in 4-O-methyl-3-(2-nitroethyl)indole (12C-1). A solution of 1.0 M of lithium aluminum in THF (4.6 mL, 4.6 mmol) was added to a cooled solution of 4-methoxy-3-(2-nitroethyl)indole (12C-1, 202 mg, 0.92 mmol) in anhydrous THF (9.2 mL). The reaction mixture was warmed to room temperature then heated to reflux. After three hours, the reaction mixture was cooled in an ice-water bath and was quenched with 10% water/THF until no more hydrogen gas evaluation. The precipitate was filtered, and the filtrate was dried over anhydrous $Na_2SO_4$. The organic solvent was concentrated under reduced pressure to afford the desired 4-methoxy psilocybin derivative (see: FIG. 12C, 12C-2) as an orange solid, which was used in the next step without further purification. Yield: 73%. The $^1$H NMR spectrum agreed with previously reported procedure (Kerschgens, I.; Claveau, E.; Wanner, M.; Ingemann, S.; Maarseveen, J. H.; Hiemstra, H. Chem. Commun. 2012, 48, 12243-12245.). $^1$H NMR (400 MHz, $CDCl_3$) δ 8.13 (bs, 1H), 7.08 (t, J=7.9 Hz, 1H), 6.96 (d, J=8.1 Hz, 1H), 6.90-6.85 (m, 1H), 6.49 (d, J=7.8 Hz, 1H), 3.91 (s, 3H), 3.01 (m, 4H).

The second step involved the full protection of side chain amino group and also the indole N of compound 12C-2 using Boc. To a solution of crude 4-methoxy psilocybin derivative (12C-2, 128 mg, 0.67 mmol) in anhydrous acetonitrile (4.3 mL) was added Di-tert-butyl dicarbonate (730 mg, 3.34 mmol) and DMAP (41.0 mg, 0.33 mmol). The reaction mixture was stirred at room temperature overnight. The reaction mixture was diluted with water (20 mL) and extracted in dichloromethane (3×20 mL). The combined organic solution was washed with brine (30 mL), dried over anhydrous $Na_2SO_4$, and concentrated under reduced pressure. The crude mixture was purified by flash column chromatography on silica gel (eluted with a gradient of hexanes-dichloromethane, 100:0→0:100) to afford the N1,N,N-triBoc protected 4-methoxy psilocybin derivative 12C-3 (see: FIG. 12C) as a yellow oil. Yield: 45%. $^1$H NMR (400 MHz, $CDCl_3$) δ 7.74 (d, J=8.4 Hz, 1H), 7.22-7.16 (m, 2H), 6.64 (d, J=7.9 Hz, 1H), 3.96-3.89 (m, 5H), 3.08 (t, J=6.7 Hz, 2H), 1.63 (s, 9H), 1.39 (s, 18H). $^{13}$C NMR (100 MHz, $CDCl_3$) δ 154.4, 152.7, 149.7, 137.2, 125.1, 122.2, 120.0, 118.0, 108.3, 103.2, 83.3, 81.8, 55.2, 46.9, 28.2, 27.9, 26.6. HRMS (ESI, positive) m/z for $C_{16}H_{23}N_2O_3[M-2Boc+H]^+$ calcd. 291.1703, found 291.1705.

The third step involved the 7-formylation of compound 12C-3 using Vilsmeier reagent. To a flask containing anhydrous DMF (4.0 mL) was added $POCl_3$ (372 μL, 4.08 mmol, 10 eq.), and the mixture was stirred at room temperature for 10 min. The obtained mixture was then added to a solution of compound 12C-3 (200 mg, 0.408 mmol) in anhydrous DMF (8.0 mL), and the mixture was heated at 60° C. for overnight. TLC showed all starting material was consumed. The reaction mixture was quenched by a solution of sat. $NaHCO_3$. The mixture was extracted with EtOAc (~50 mL), the organic layer was dried over anhydrous Na2SO4 and concentrated under reduced pressure. The crude product was purified by flash chromatography on silica gel using a gradient of dichloromethane-MeOH (100:0→90:10) to afford compound 12A-4 as a pale yellow solid (63 mg, 38% yield). $^1$H NMR (400 MHz, CDCl$_3$) δ 9.24 (s, 1H), 7.77 (d, J=8.3 Hz, 1H, NH), 7.22 (dd, 2H), 6.68 (d, J=8.3 Hz, 1H), 3.98 (m, 5H), 3.05 (td, 2H), 1.66 (s, 9H), 1.33 (s, 9H).

The fourth step involved the removal of the Boc protecting groups on the side chain. To a solution of aldehyde derivative 12C-4 (5.4 mg, 0.013 mmol, see: FIG. 12C) obtained above in a mixture of anhydrous dichloromethane-trifluoroacetic acid (1:1, v/v). The mixture was stirred at rt for 2 hours. The reaction was monitored by TLC (10% MeOH in DCM). The reaction was quenched by NaHCO$_3$ and concentrated by rotavap. The crude product was then purified on silica gel column by combi-flash chromatography system using a gradient of dichloromethane-methanol (100:0→100 to 10) to provide the desired product 12C-5 (1.8 mg, 64% yield, see: FIG. 12C) as a pale-yellow solid. $^1$H NMR (400 MHz, CD3OD) δ 8.02 (s, 1H, CHO), 7.18 (s, 1H, =CH), 6.99 (d, 1H, Ar—H), 6.94 (d, 1H, Ar—H), 6.47 (d, 1H, =CH), 3.93 (m, 3H, OCH$_3$), 3.55 (t, 2H, CH$_2$), 3.06 (t, 2H, CH$_2$). HRMS (ESI, positive) m/z for C$_{12}$H$_{15}$N$_2$O$_2$ [M+H]$^+$ calcd. 219.1128, found 219.1130.

It is noted that compound 12C-5 corresponds with the chemical compound having formula (X):

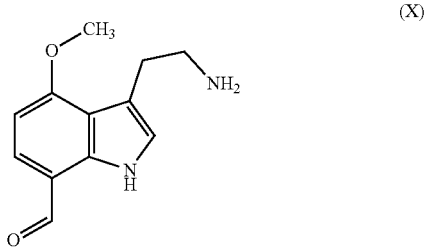 [SMILES: COc1ccc(C=O)c2[nH]cc(CCN)c12]

(X)

set forth herein.

Assessment of Cell Viability Upon Treatment of Aldehyde Psilocybin Derivative

Cell viability was assessed as described for Example 1, except the compound with formula (X) was evaluated in place of the compound with formula (VIII). FIG. 14A shows PrestoBlue assay results for compound with formula (X), depicted on the x-axis as "X".

Radioligand receptor binding assays.

Activity at 5-HT$_{2A}$ receptor was assessed as described for Example 1, except the compound with formula (X) was evaluated in place of the compound with formula (VIII). FIG. 14B shows radioligand competition assay results for compound with formula (X), depicted on the x-axis simply as "X".

Cell lines and control ligands used to assess activity at 5-HT$_{1A}$.

CHO-K1/Gα15 (GenScript, M00257) (−5-HT$_{1A}$) and CHO-K1/5-HT$_{1A}$/Gα$_{15}$ (GenScript, M00330) (+5-HT$_{1A}$) cells lines were used. Briefly, CHO-K1/Gα$_{15}$ is a control cell line that constitutively expresses Gα$_{15}$ which is a promiscuous G$_q$ protein. This control cell line lacks any transgene encoding 5-HT$_{1A}$ receptors, but still responds to forskolin; thus, cAMP response to forskolin should be the same regardless of whether or not 5-HT$_{1A}$ agonists are present. Conversely, CHO-K1/5-HT$_{1A}$/Gα$_{15}$ cells stably express 5-HT$_{1A}$ receptor in the CHO-K1 host background. Notably, Gα15 is a promiscuous G protein known to induce calcium flux response, present in both control and 5-HT$_{1A}$ cell lines. In +5-HT$_{1A}$ cells, Gα$_{15}$ may be recruited in place of G$_{αi/o}$; which could theoretically dampen cAMP response (Rojas and Fiedler 2016, Front Cell Neurosci 10: 272). Thus, we included two known 5-HT$_{1A}$ agonists, DMT (Cameron and Olson 2018, ACS Chem Neurosci 9: 2344) and serotonin (Rojas and Fiedler 2016, Front Cell Neurosci 10: 272) as positive controls to ensure sufficient cAMP response was observed, thereby indicating measurable recruitment of G$_{αi/o}$ protein to activated 5-HT$_{1A}$ receptors. In contrast, tryptophan is not known to activate, or modulate in any way, 5-HT$_{1A}$ receptors, and was thus used as a negative control. Cells were maintained in complete growth media as recommended by supplier (GenScript) which is constituted as follows: Ham's F12 Nutrient mix (HAM's F12, GIBCO #11765-047) with 10% fetal bovine serum (FBS) (Thermo Scientific #12483020), 200 µg/ml zeocin (Thermo Scientific #R25005) and/or 100 µg/ml hygromycin (Thermo Scientific #10687010). The cells were cultured in a humidified incubator with 37° C. and 5% CO$_2$. Cells maintenance was carried out as recommended by the cell supplier. Briefly, vials with cells were removed from the liquid nitrogen and thawed quickly in 37° C. water bath. Just before the cells were completely thawed the vial's outside was decontaminated by 70% ethanol spray. The cell suspension was then retrieved from the vial and added to warm (37° C.) complete growth media, and centrifuged at 1,000 rpm for 5 minutes. The supernatant was discarded, and the cell pellet was then resuspended in another 10 ml of complete growth media, and added to the 10 cm cell culture dish (Greiner Bio-One #664160). The media was changed every third day until the cells were about 90% confluent. The ~90% confluent cells were then split 10:1 for maintenance or used for experiment.

Evaluation of 5-HT$_{1A}$ Receptor Modulation

As 5-HT$_{1A}$ activation inhibits cAMP formation, the ability of test molecules to modulate the 5-HT$_{1A}$ receptor response was measured via changes in the levels of cAMP produced due to application of 4 µM forskolin. The change in intracellular cAMP levels due to the treatment of novel molecules was measured using cAMP-Glo Assay kit (Promega # V1501). Briefly, +5-HT$_{1A}$ cells were seeded on 1-6 columns and base −5-HT$_{1A}$ cells were seeded on columns 7-12 of the white walled clear bottom 96-well plate (Corning, #3903). Both cells were seeded at the density of 30,000 cells/well in 100 µl complete growth media and cultured 24 hrs in humidified incubator at 37° C. and 5% CO$_2$. On the experiment day, the media of cells was replaced with serum/antibiotic free culture media. Then the cells were treated for 20 minutes with test molecules dissolved in induction medium (serum/antibiotic free culture media containing 4 µM forskolin, 500 µM IBMX (isobutyl-1-methylxanthine, Sigma-Aldrich, Cat. #17018) and 100 µM (RO 20-1724, Sigma-Aldrich, Cat. #68279)). Forskolin induced cAMP formation whereas IBMX and RO 20-1724 inhibited the degradation of cAMP. PKA was added to the lysate, mixed, and subsequently the substrate of the PKA was added. PKA was activated by cAMP, and the amount of ATP consumed due to PKA phosphorylation directly corresponded to cAMP levels in the lysate. Reduced ATP caused reduced conversion of luciferin to oxyluciferin, conferring diminished luminescence as the result of 5-HT$_{1A}$ activation. Conversely, enhanced luminescence was expected in cases where 5-HT$_{1A}$ receptor modulation—imparted by a test molecule—caused downstream increases in ATP, thus imparting enhanced conversion of luciferin to oxyluciferin. FIG. 14C shows increased luminescence resulting from decreased dosages of forskolin (and decreased cAMP) in +5HT$_{1A}$ cell culture. FIG. 14D illustrates reduced luminescence (i.e., increased cAMP) in the presence of fixed (4 µM) forskolin as dosages of DMT decrease, revealing 5-HT$_{1A}$ activity of DMT. FIG. 14E illustrates no trend in luminescence (i.e., no trend in cAMP levels) in the presence of fixed (4 μM) forskolin, as dosages of tryptophan decrease, revealing a lack of 5-HT$_{1A}$ modulation for tryptophan. FIG. 14F illustrates increased % cAMP levels in the presence of fixed (4 μM) forskolin as dosages of serotonin decrease, revealing 5-HT$_{1A}$ binding activity of serotonin in +5HT$_{1A}$ cell cultures. Conversely, this trend of increasing % cAMP levels with decreasing serotonin is not observed in −5HT$_{1A}$ cell cultures.

FIG. 14G illustrates decreased % cAMP levels in the presence of fixed (4 μM) forskolin as dosages of compound (X) decrease, revealing ability of compound (X) to modulate 5-HT$_{1A}$ response in +5HT$_{1A}$ cell cultures. Conversely, this trend of decreasing % cAMP levels with decreasing compound (X) is not observed in −5HT$_{1A}$ cell cultures. It is noted that compound (X) is depicted as "X" along the x-axis. For FIGS. 14C-14E, error bars represent results of three experiments (n=3).

Example 4—Preparation of a First Ketone Derivative of Psilocybin

Preparation of a ketone psilocybin derivative was performed according to the scheme shown in FIG. 12D. Thus, referring to FIG. 12D, the first step was carried out as follows: to a cooled solution of 4-benzyloxyindole (compound 12D-1 (see: FIG. 12D) 1.50 g, 6.72 mmol) in anhydrous THF (7.5 mL) was added oxalyl chloride (0.70 mL, 8.27 mmol). The reaction mixture was stirred in an ice-water bath for 2 hours. Dibutylamine (1.35 mL, 8.01 mmol) was added, and the resulting mixture was stirred in an ice-water bath for another hour. The reaction was quenched with 2N NaOH (20 mL), extracted with ethyl acetate (3×20 mL), dried over anhydrous Na$_2$SO$_4$, and concentrated in vacuo. The crude product was purified by flash column chromatography on silica gel using a gradient of hexanes-EtOAc (100:00 to 100:00) to afford compound 12D-2 (see: FIG. 12D) as a brown oil. $^1$H NMR (400 MHz, CDCl$_3$) 9.89 (s, 1H), 7.63 (dd, J=3.3, 1.1 Hz, 1H), 7.62-7.54 (m, 2H), 7.40-7.23 (m, 4H), 7.05 (t, J=8.1 Hz, 1H), 6.91 (d, J=8.1 Hz, 1H), 6.64 (d, J=7.9 Hz, 1H), 5.25 (s, 2H), 3.37 (t, J=7.6 Hz, 2H), 3.24 (d, J=7.6 Hz, 2H), 1.65-1.50 (m, 4H), 1.15 (h, J=7.4 Hz, 2H), 1.13 (h, J=7.4 Hz, 2H), 0.94 (t, J=7.3 Hz, 3H), 0.77 (t, J=7.3 Hz, 3H). 1.0 M of lithium aluminum in THF (5.70 mL) was added dropwise to a stirred solution of compound 12D-2 (0.39 g, 0.95 mmol) in anhydrous THF (8.0 mL) in an ice-water bath. The reaction mixture was heated to reflux for 2 days. Once the reaction mixture was cooled to room temperature, 10% water/THF mixture was added until hydrogen gas evaluation ceased. Anhydrous diethyl ether (10 mL) was added, and the mixture was stirred at room temperature for an hour. The precipitate was filtered, and the filtrate was dried over anhydrous Na$_2$SO$_4$. The organic solvent was concentrated under reduced pressure to afford compound 12D-3 (see: FIG. 12D) as a pale brown oil, which was used in the next step without further purification. Trifluoroacetic anhydride (0.64 mL, 4.60 mmol) was added to a mixture of compound 12D-3 (0.19 g, 0.51 mmol) in dichloromethane (7.5 mL). The reaction mixture was stirred at room temperature for 2 days then neutralized with water (20 mL). The mixture was extracted with dichloromethane (2×20 mL), dried over anhydrous Na$_2$SO$_4$, and concentrated under reduced pressure. The crude material was purified by flash column chromatography on silica gel (eluted with a gradient of DCM-MeOH, 100:00 to 80:20) to afford compound 12D-4 (see: FIG. 12D) as a yellow oil. Yield: 7%. $^1$H NMR (400 MHz, CDCl$_3$) δ 7.92 (dq, J=8.7, 1.9 Hz, 1H), 7.51-7.39 (m, 5H), 7.20 (d, J=2.3 Hz, 1H), 6.74 (d, J=8.7 Hz, 1H), 5.33 (s, 2H), 3.38-3.29 (m, 2H), 3.21-3.12 (m, 2H), 2.85-2.76 (m, 2H), 2.70-2.57 (m, 2H), 1.63-1.48 (m, 4H), 1.30-1.19 (m, 4H), 0.89 (t, J=7.3 Hz, 6H). It is noted that compound 12D-4 corresponds with the chemical compound having formula (XI):

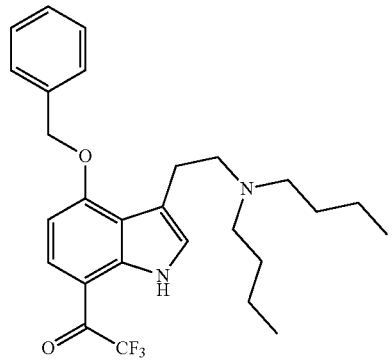

(XI)

set forth herein.

Example 5—Preparation of a Fourth and Fifth Aldehyde Derivative of Psilocybin

Preparation of two aldehyde psilocybin derivatives was performed according to the scheme shown in FIG. 12E. Thus, referring to FIG. 12E, the first step was carried out as follows: compound 12E-1 (500 mg, 2.27 mmol, 1.00 eq) was dissolved in anhydrous THF (5 mL) under argon atmosphere and cooled to 0° C. Oxalyl chloride (518 mg, 4.08 mmol, 1.80 eq) was added and the solution stirred at 0° C. for 2 hours. Dibutylamine (529 mg, 4.09 mmol, 1.80 eq) was added, then the solution was allowed to warm to room temperature and stirred for a further 2 hours. The suspended precipitate was removed through filtration, and the filtrate quenched with 2N NaOH (10 mL) and extracted with ethyl acetate (3×10 mL). The organic extracts were dried over MgSO$_4$ and concentrated in vacuo. The crude mixture was purified via column chromatography on silica gel with 20% to 40% ethyl acetate-hexanes gradient as eluent to yield the desired product 12E-2 (see: FIG. 12E) (267 mg, 0.808 mmol, 36%). $^1$H NMR (400 MHz, CDCl$_3$): δ (ppm)=9.93 (s, 1H), 7.60 (d, J=3.2 Hz, 1H), 7.15 (t, J=8.0 Hz, 1H), 6.97 (dd, J=8.2, 0.7 Hz, 1H), 6.65 (d, 1H), 3.92 (s, 3H), 3.57-3.47 (m, 2H), 3.38-3.30 (m, 2H), 1.75-1.56 (m, 4H), 1.43 (h, J=7.4 Hz, 2H), 1.22 (h, J=7.4 Hz, 2H), 1.00 (t, J=7.3 Hz, 3H), 0.84 (t, J=7.4 Hz, 3H). Compound 12E-2 (267 mg, 0.808 mmol, 1.00 eq) was dissolved in anhydrous THF (8 mL) under argon atmosphere and cooled to 0 Lithium aluminum hydride (4.9 mL, 1.0 M, 6 eq) was added dropwise and the reaction was subsequently heated to 78° C. overnight. As the solvent evaporated overnight, additional anhydrous THF (8 mL) was added to the reaction flask and the reaction mixture was heated at 78 for one more night. The reaction mixture was cooled, then quenched with 10% water-THF (5 mL) and the suspended precipitate removed via vacuum filtration. The filtrate was dried over MgSO$_4$ and the solvent was removed in vacuo to yield the desired product 12E-3 (see: FIG. 12E) as brown solids (147 mg, 0.486 mmol, 60%). $^1$H NMR (400 MHz, CDCl$_3$): δ (ppm)=8.21 (s, 1H), 7.10 (t, J=7.9 Hz, 1H), 6.97 (dd, J=8.2, 0.7 Hz, 1H), 6.89 (d, J=2.2 Hz, 1H), 6.51 (d, 1H), 3.94 (s, 3H), 3.12-3.01 (m, 2H), 2.89-2.80 (m, 2H), 2.66-2.55 (m, 4H), 1.63-1.51 (m, 4H), 1.44-1.31 (m, 4H), 0.97 (t, J=7.3 Hz, 6H). A flame dried round-bottom flask under argon atmosphere was charged with triphenylphosphine (380 mg, 1.45 mmol, 2.98 eq) and anhydrous THF (3.5 mL). N-chlorosuccinimide (200 mg, 1.50 mmol, 3.08 eq) was added and the reaction stirred at room temperature for 30 minutes. Anhydrous dimethylformamide (217 mg, 2.97 mmol, 6.11 eq) was added to the reaction flask and heated to reflux for 1 hour. Compound 12E-3 (147 mg, 0.486 mmol, 1.00 eq) in anhydrous THF (3 mL) was added, and the reaction mixture was heated to 61 overnight. Water (2.3 mL) was added, and the reaction was heated to reflux for 1 hour. The reaction mixture was cooled to room temperature, basified with 10% NaOH, and allowed to stir for 1 hour. The reaction mixture was then neutralized with concentrated HCl and extracted with DCM (4×20 mL). The combined organic extracts were washed with brine and dried over $Na_2SO_4$ followed by removal of solvent under vacuum. The crude material was purified by column chromatography on silica gel with 2% to 6% methanol-DCM as eluent. A second purification was performed by column chromatography on silica gel using 60%-100% ethyl acetate-hexanes as eluent to yield compounds 12E-4 (see: FIG. 12E) (1.3 mg, 0.00394 mmol, 0.8%) and 12E-5 (see: FIG. 12E) (3.2 mg, 0.010 mmol, 2.0%), which eluted separately as pure compounds. Compound 12E-4: $^1$H NMR (400 MHz, Methanol-d4): δ (ppm)=9.94 (s, 1H), 7.26 (t, J=8.4 Hz, 1H), 6.99 (dd, J=8.4, 0.6 Hz, 1H), 6.53 (d, J=7.8 Hz, 1H), 3.97 (s, 3H), 3.44-3.37 (m, 2H), 2.89-2.81 (m, 2H), 2.67-2.60 (m, 4H), 1.54 (tt, J=7.9, 6.0 Hz, 4H), 1.38 (dq, J=14.6, 7.4 Hz, 4H), 0.98 (t, J=7.3 Hz, 6H). Purity was determined to be 95%. It is noted that compound 12E-4 corresponds with the chemical compound having formula (XII):

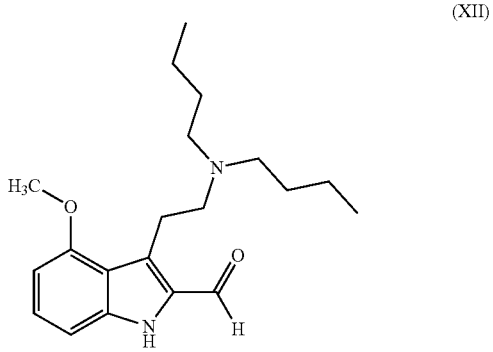 [SMILES: CCCCN(CCCC)CCc1c(C=O)[nH]c2cccc(OC)c12]

(XII)

set forth herein. Compound 12E-5: $^1$H NMR (400 MHz, Methanol-d4): δ (ppm)=9.90 (s, 1H), 7.67 (d, J=8.2 Hz, 1H), 7.09 (s, 1H), 6.76 (d, J=8.2 Hz, 1H), 4.07 (s, 3H), 3.10-3.02 (m, 2H), 2.86 (dd, J=10.2, 5.8 Hz, 2H), 2.65 (q, J=9.6, 9.0 Hz, 4H), 1.57 (tdd, J=14.3, 6.7, 3.9 Hz, 4H), 1.44-1.34 (m, 4H), 0.98 (td, J=7.3, 5.3 Hz, 6H). HRMS (ESI, positive) m/z for $C_{20}H_{30}N_2O_2$ [M+H]$^+$ calcd. 331.23800, found 331.2382. It is noted that compound 12E-5 corresponds with the chemical compound having formula (XV):

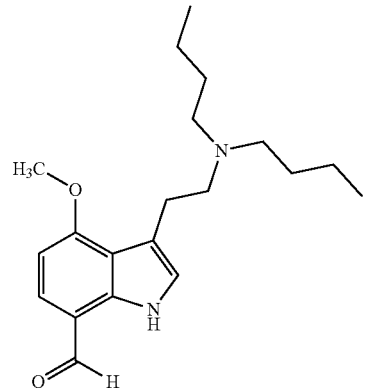

(XV)

set forth herein.

Assessment of Cell Viability Upon Treatment of Aldehyde Psilocybin Derivative

Cell viability was assessed as described for Example 1, except the compound with formula (XII) was evaluated in place of the compound with formula (VIII). FIG. 15A shows PrestoBlue assay results for compound with formula (XII), depicted on the x-axis as "XII". Compound with formula (XV) was not evaluated.

Radioligand receptor binding assays.

Activity at 5-HT$_{2A}$ receptor was assessed as described for Example 1, except the compound with formula (XII) was evaluated in place of the compound with formula (VIII). FIG. 15B shows radioligand competition assay results for compound with formula (XII), depicted on the x-axis simply as "XII". Compound with formula (XV) was not evaluated.

Cell Lines and Control Ligands Used to Assess Activity at 5-HT$_{1A}$ and Experimental Procedures Assessing 5-HT$_{1A}$ Modulation Cell lines, cell line maintenance, and experimental procedures assessing modulation of 5-HT$_{1A}$ were performed as described in Example 3, except that compound (XII) was evaluated in place of compound (X). FIG. 15C illustrates decreased % cAMP levels in the presence of fixed (4 mM) forskolin as dosages of compound (XII) decrease, revealing 5-HT$_{1A}$ modulation activity of compound (XII) in +5HT$_{1A}$ cell cultures. Conversely, this trend of decreasing % cAMP levels with decreasing compound (XII) is not observed in −5HT$_{1A}$ cell cultures. It is noted that compound (XII) is depicted as "XII" along the x-axis. Compound with formula (XV) was not evaluated.

Example 6—Preparation of a Second Ketone Derivative of Psilocybin (a 4-O-Methyl-7-Acetyl Derivative)

Preparation of 4-O-methyl-7-acetyl psilocybin derivative (12F-3) was performed according to the scheme shown in FIG. 12F using 4-O-methyl-3-(2-nitroethyl)indole (12F-1, same as 12C-1) as a starting material. Thus, referring to FIG. 12F, the first synthesis involved a Lewis acid-catalyzed Friedel-Craft acylation of compound 12F-1. A flame-dried round-bottom flask under argon atmosphere was charged with aluminum trichloride (133 mg, 1.00 mmol, 2.20 eq) and anhydrous dichloromethane (2.5 mL) and cooled to 0° C. Acetyl chloride (36 µL, 0.50 mmol, 1.10 eq) was added and the mixture was allowed to stir for 30 minutes. A solution of compound 12F-1 (same as 12C-1, 100 mg, 0.45 mmol) in anhydrous dichloromethane (2.5 mL) was added dropwise to the mixture, and the reaction was allowed to warm up to room temperature and the reaction was continued overnight. The reaction mixture was poured over ice-water (10.0 mL) and the pH was adjusted to 8-9 with saturated sodium bicarbonate. The organic phase was isolated, and the aqueous phase extracted with dichloromethane (20 mL). The combined organic phases were washed with brine, dried with $Na_2SO_4$, and concentrated under vacuum. The crude mixture was purified by column chromatography on silica gel using a gradient of 10%→30% ethyl acetate-hexanes to afford the desired compound 12F-2 (see: FIG. 12F) as a tan powder (40 mg, 0.15 mmol, 34%). $^1$H NMR (400 MHz, $CDCl_3$): δ (ppm)=10.38 (s, 1H), 7.75 (d, J=8.4 Hz, 1H), 7.02 (d, J=2.2 Hz, 1H), 6.54 (d, J=8.4 Hz, 1H), 4.69 (t, J=7.2 Hz, 2H), 4.02 (s, 3H), 3.55 (td, J=7.2, 0.8 Hz, 2H), 2.62 (s, 3H). HRMS (ESI, positive) m/z for $C_{13}H_{14}N_2O_4[M+]^+$ calcd. 263.10263, found 263.1028.

The second step involved the reduction of nitro functionality of the side chain in compound 12F-2. To a solution of compound 12F-2 (40 mg, 0.15 mmol, 1.0 eq) in a methanol (5.00 mL)-dichloromethane (2.0 mL) solution was added 10% palladium on activated carbon (19 mg, 0.0098 mmol, 0.065 eq) followed by ammonium formate (92 mg, 3.1 mmol, 20 eq). This mixture was allowed to stir at 40 for 5 hours. More ammonium formate (92 mg, 3.1 mmol, 20 eq) was added and the mixture heated to 65° C. for 18 hours. After cooling to room temperature, a syringe filter was used to remove the catalyst and the filtrate was concentrated under vacuum. The crude product was purified by column chromatography on C18 silica gel using 80% acetonitrile–water+0.1% formic acid as the eluent to afford compound 12F-3 (see: FIG. 12F) as an off-white solid (8.5 mg, 0.037 mmol, 24%). $^1$H NMR (400 MHz, $CD_3OD$) δ 7.85 (d, J=8.4 Hz, 1H), 7.05 (s, 1H), 6.63 (d, J=8.5 Hz, 1H), 4.02 (s, 3H), 3.06-2.98 (m, 2H), 2.92 (t, J=6.7 Hz, 2H), 2.62 (s, 3H). HRMS (ESI, positive) m/z for $C_{13}H_{16}N_2O_2[M+H]^+$ calcd. 233.12845, found 233.1283.

It is noted that compound 12F-3 corresponds with the chemical compound having formula (XIII):

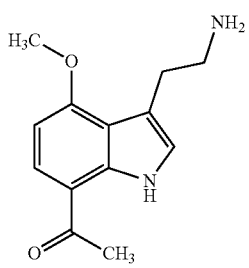

(XIII)

set forth herein.

Assessment of Cell Viability Upon Treatment of Aldehyde Psilocybin Derivative

Cell viability was assessed as described for Example 1, except the compound with formula (XIII) was evaluated in place of the compound with formula (VIII). FIG. 16A shows PrestoBlue assay results for compound with formula (XIII), depicted on the x-axis as "XIII".

Radioligand receptor binding assays.

Activity at $5\text{-HT}_{2A}$ receptor was assessed as described for Example 1, except the compound with formula (XIII) was evaluated in place of the compound with formula (VIII).

FIG. 16B shows radioligand competition assay results for compound with formula (XIII), depicted on the x-axis as "XIII".

Example 7—Preparation of a Third Ketone Derivative of Psilocvbin

Figure 12G:
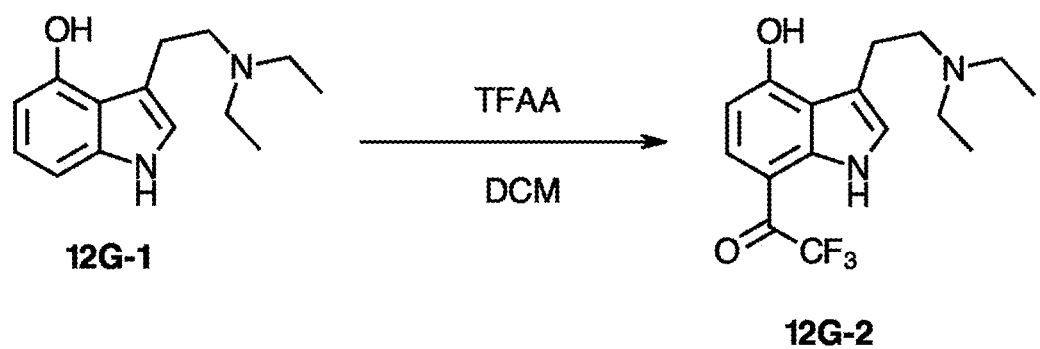

Preparation of a ketone psilocybin derivative was performed according to the scheme shown in FIG. 12G. Thus, referring to FIG. 12G, the first step was carried out as follows: a solution of compound 12G-1 (see: FIG. 12G) (120 mg) in anhydrous DCM (5.0 mL) was cooled with an ice-water bath, and trifluoroacetic anhydride (0.45 mL) was added. After stirring reaction mixture for 7 hours at room temperature, the reaction was quenched with water (10 mL), and the mixture was extracted with ethyl acetate (3×10 mL). The combined organic solutions were dried over anhydrous $Na_2SO_4$ and concentrated in vacuo. The crude product was purified by flash chromatography on silica gel column using hexanes/EtOAc as eluent to afford a crude compound 12G-2 (see: FIG. 12G) as a yellow solid. 1H NMR showed it was still crude mixture, but HRMS did observe the desired product: HRMS (ESI, positive) m/z for $C_{16}H_{20}F_3N_2O_2$ $[M+H]^+$ calcd. 329.1471, found 329.1466. It is noted that compound 12G-2 corresponds with the chemical compound having formula (XIV):

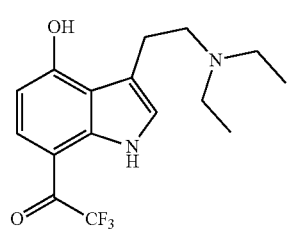

(XIV)

set forth herein.

The invention claimed is:
1. A chemical compound having the chemical formula (I):

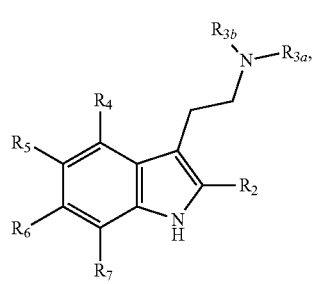

(I)

wherein, $R_7$ is an aldehyde or a ketone group wherein $R_4$ is an O-alkyl group, an O-alkaryl group, or a hydroxy group, wherein $R_2$, $R_5$ and $R_6$ are a hydrogen atom, and wherein $R_{3a}$ and $R_{3b}$ each independently are a hydrogen atom, an alkyl group, wherein at least one of the alkyl groups is a $C_2$-$C_6$ alkyl group, acyl group, or an aryl group.

2. A chemical compound according to claim 1, wherein the ketone group has the chemical formula (II):

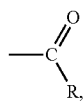
(II)

wherein R is an alkyl group, a halogenated alkyl group or an aryl group.

3. A chemical compound according to claim 1, wherein the aldehyde group has the chemical formula (IV):

(IV)

4. A chemical compound according to claim 1, wherein $R_4$ is a hydroxy group or an O-alkyl group.

5. A chemical compound according to claim 4, wherein the O-alkyl group is a $(C_1-C_6)$-O-alkyl group.

6. A chemical compound according to claim 4, wherein the O-alkyl group is a $(C_1-C_3)$-O-alkyl group.

7. A chemical compound according to claim 4, wherein the O-alkyl group is a methoxy group (—$OCH_3$).

8. A chemical compound according to claim 4, wherein the O-alkaryl group is a O-$(C_1-C_6)$-alkyl-phenyl group.

9. A chemical compound according to claim 4, wherein $R_{3a}$ and $R_{3b}$ are each an independently selected $(C_1-C_6)$-alkyl group or a hydrogen atom.

10. A chemical compound according to claim 4, wherein $R_{3a}$ and $R_{3b}$ are each an independently selected $(C_1-C_4)$-alkyl group.

11. A chemical compound according to claim 4, wherein $R_{3a}$ and $R_{3b}$ are each an independently selected $(C_1-C_2)$-alkyl group.

12. A chemical compound according to claim 1, wherein the chemical compound is selected from the group consisting of compounds having formulas (VIII), (IX), (X), (XI), (XIII), (XIV), and (XV):

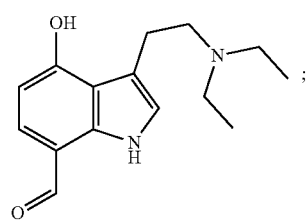
(VIII)

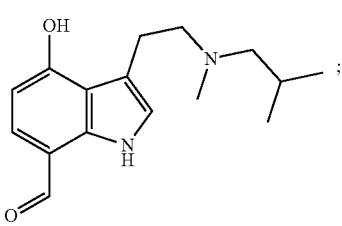
(IX)

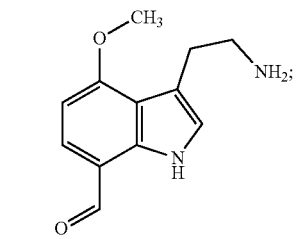
(X)

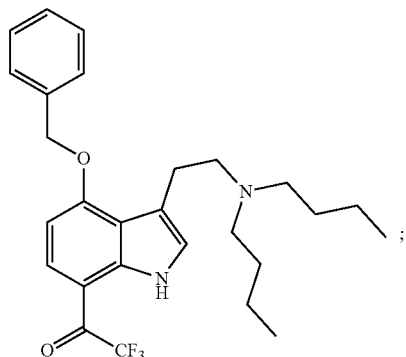
(XI)

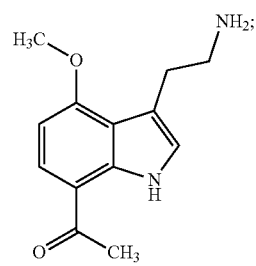
(XIII)

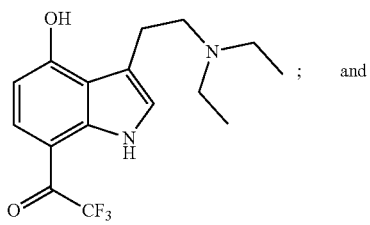
(XIV)

and

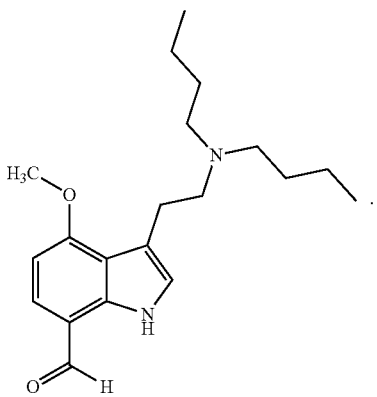
(XV)

13. A chemical compound according to claim 1, wherein the compound is at least about 95% (w/w) pure.

14. A pharmaceutical or recreational drug formulation comprising an effective amount of a chemical compound according to claim 1, together with a pharmaceutically acceptable excipient, diluent, or carrier.

15. A method for treating a psychiatric disorder, the method comprising administering to a subject in need thereof a pharmaceutical formulation comprising a chemical compound according to claim 1, wherein the pharmaceutical formulation is administered in an effective amount to treat the psychiatric disorder in the subject.

16. A chemical compound according to claim 12, wherein the compound is at least about 95% (w/w) pure.

17. A pharmaceutical or recreational drug formulation comprising an effective amount of a chemical compound according to claim 12, together with a pharmaceutically acceptable excipient, diluent, or carrier.

18. A method for treating a psychiatric disorder, the method comprising administering to a subject in need thereof a pharmaceutical formulation comprising a chemical compound according to claim 12, wherein the pharmaceutical formulation is administered in an effective amount to treat the psychiatric disorder in the subject.

* * * * *